US007285242B2

(12) United States Patent
Ogura

(10) Patent No.: US 7,285,242 B2
(45) Date of Patent: Oct. 23, 2007

(54) BIOCHEMICAL ANALYSIS UNIT AND BIOCHEMICAL ANALYZING METHOD USING THE SAME

(75) Inventor: Nobuhiko Ogura, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 09/918,500

(22) Filed: Aug. 1, 2001

(65) Prior Publication Data

US 2002/0016009 A1    Feb. 7, 2002

(30) Foreign Application Priority Data

Aug. 2, 2000   (JP)   ............... 2000-234776
Mar. 30, 2001  (JP)   ............... 2001-100942
Jun. 29, 2001  (JP)   ............... 2001-199183

(51) Int. Cl.
*G01N 21/76*    (2006.01)
*G01N 33/566*   (2006.01)
*G01N 33/567*   (2006.01)
*G01N 33/557*   (2006.01)
*C12M 1/42*     (2006.01)
*C12M 1/34*     (2006.01)
*C12Q 1/68*     (2006.01)
*G01N 33/53*    (2006.01)
*C12P 19/34*    (2006.01)
*C07H 19/00*    (2006.01)
*C07H 21/00*    (2006.01)
*C07H 21/04*    (2006.01)

(52) U.S. Cl. ............... 422/52; 435/6; 435/7.1; 435/91.1; 435/91.2; 435/285.2; 435/287.2; 536/22.1; 536/23.1; 536/24.3; 536/24.33; 436/501; 436/506; 436/507

(58) Field of Classification Search ............... 435/6, 435/7.1, 91.1, 91.2, 285.2, 287.2; 536/22.1, 536/23.1, 24.3–24.33; 422/52; 436/501, 436/506, 517

See application file for complete search history.

(56) References Cited

U.S. PATENT DOCUMENTS 4,728,792 A * 3/1988 Warner et al. ............... 250/328

(Continued)

FOREIGN PATENT DOCUMENTS

WO    WO94 26413 A1    11/1994
WO    WO99 09415 A1    2/1999

OTHER PUBLICATIONS

European Search Report, K 53 218/7 as, 01118133.6-2204-, Fuji Photo Film Co., Ltd., dated Dec. 12, 2003.

*Primary Examiner*—Jezia Riley
(74) *Attorney, Agent, or Firm*—Sughrue Mion Pllc.

(57) ABSTRACT

A biochemical analysis unit includes a substrate made of a material capable of attenuating radiation energy and/or light energy and formed with a plurality of holes, and a plurality of absorptive regions formed by forming an absorptive region in every hole. According to the thus constituted biochemical analysis unit, even in the case where the absorptive regions are formed at a high density, when a stimulable phosphor layer formed on a stimulable phosphor sheet is exposed to a radioactive labeling substance contained in the plurality of absorptive regions, electron beams ($\beta$ rays) released from the radioactive labeling substance contained in the individual absorptive regions are reliably prevented from being scattered in the substrate and advancing to regions of the stimulable phosphor layer that should be exposed to electron beams released from absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy.

38 Claims, 20 Drawing Sheets

U.S. PATENT DOCUMENTS

| | | |
|---|---|---|
| 4,752,557 A | 6/1988 | Tsuchino et al. |
| 5,260,190 A | 11/1993 | Shiraishi et al. |
| 5,837,194 A * | 11/1998 | Potter et al. .................. 422/52 |
| 6,130,440 A * | 10/2000 | Ogura ........................ 250/586 |
| 6,207,369 B1 * | 3/2001 | Wohlstadter et al. .......... 435/6 |
| 6,238,909 B1 * | 5/2001 | Choong et al. .......... 435/287.2 |
| 6,426,050 B1 * | 7/2002 | Pham et al. ................. 422/104 |
| 6,448,089 B1 * | 9/2002 | Vuong ........................ 436/164 |

* cited by examiner

BIOCHEMICAL ANALYSIS UNIT AND BIOCHEMICAL ANALYZING METHOD USING THE SAME

BACKGROUND OF THE INVENTION

The present invention relates to a biochemical analysis unit and a biochemical analyzing method using the same and, particularly, to a biochemical analysis unit and a biochemical analyzing method which can prevent noise caused by the scattering of electron beams released from a radioactive labeling substance from being generated in biochemical analysis data even in the case of forming spots of specific binding substances on the surface of a carrier at a high density, which can specifically bind with a substance derived from a living organism and whose sequence, base length, composition and the like are known, specifically binding the spot-like specific binding substances with a substance derived from a living organism labeled with a radioactive substance to selectively label the spot-like specific binding substances with the radioactive substance, thereby obtaining a biochemical analysis unit, superposing the thus obtained biochemical analysis unit and a stimulable phosphor layer, exposing the stimulable phosphor layer to the radioactive labeling substance, irradiating the stimulable phosphor layer with a stimulating ray to excite the stimulable phosphor, photoelectrically detecting the stimulated emission released from the stimulable phosphor layer to produce biochemical analysis data, and analyzing the substance derived from a living organism; and can prevent noise caused by the scattering of chemiluminescent emission and/or fluorescence released from a labeling substance which generates chemiluminescent emission when it contacts a chemiluminescent substrate and/or a fluorescent substance from being generated in biochemical analysis data even in the case of forming spots of specific binding substances on the surface of a carrier at high density, which can specifically bind with a substance derived from a living organism and whose sequence, base length, composition and the like are known, specifically binding the spot-like specific binding substance with a substance derived from a living organism labeled with, in addition to a radioactive labeling substance or instead of a radioactive labeling substance, a labeling substance which generates chemiluminescent emission when it contacts a chemiluminescent substrate and/or a fluorescent substance to selectively label the spot-like specific binding substances therewith, thereby obtaining a biochemical analysis unit, photoelectrically detecting chemiluminescent emission and/or fluorescence released from the biochemical analysis unit to produce biochemical analysis data, and analyzing the substance derived from a living organism.

DESCRIPTION OF THE PRIOR ART

An autoradiographic analyzing system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactively labeled substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

Unlike the system using a photographic film, according to the autoradiographic analyzing system using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence analyzing system using a fluorescent substance as a labeling substance instead of a radioactive labeling substance in the autoradiographic analyzing system is known. According to this system, it is possible to study a genetic sequence, study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

Similarly, there is known a chemiluminescence detecting system comprising the steps of fixing a substance derived from a living organism such as a protein or a nucleic acid sequence on a support, selectively labeling the substance derived from a living organism with a labeling substance which generates chemiluminescent emission when it contacts a chemiluminescent substrate, contacting the substance derived from a living organism and selectively labeled with the labeling substance and the chemiluminescent substrate, photoelectrically detecting the chemiluminescent emission in the wavelength of visible light generated by the contact of the chemiluminescent substrate and the labeling substance to produce digital image signals, effecting image processing thereon, and reproducing a chemiluminescent image on a display means such as a CRT or a recording material such as a photographic film, thereby obtaining information relating to the high molecular substance such as genetic information.

Further, a micro-array analyzing system has been recently developed, which comprises the steps of using a spotting device to drop at different positions on the surface of a carrier such as a slide glass plate, a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as a fluorescence emitted from a labeling substance such as a fluorescent substance, dye or the like, and analyzing the substance derived from a living organism. This micro-array analyzing system is advantageous in that a substance derived from a living organism can be analyzed in a short time period by forming a number of spots of specific binding substances at different positions of the surface of a carrier such as a slide glass plate at high density and hybridizing them with a substance derived from a living organism and labeled with a labeling substance.

In addition, a macro-array analyzing system using a radioactive labeling substance as a labeling substance has been further developed, which comprises the steps of using a spotting device to drop at different positions on the surface of a carrier such as a membrane filter or the like specific binding substances, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a hormone, tumor marker, enzyme, antibody, antigen, abzyme, other protein, a nuclear acid, cDNA, DNA or mRNA, which is gathered from a living organism by extraction, isolation or the like or is further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

However, in the macro-array analyzing system using a radioactive labeling substance as a labeling substance, when the stimulable phosphor layer is exposed to a radioactive labeling substance, since radiation energy of the radioactive labeling substance contained in spots formed on the surface of a carrier such as a membrane filter is very large, electron beams released from the radioactive labeling substance contained in the individual spots are scattered in the carrier such as a membrane filter, thereby impinging on regions of the stimulable phosphor layer that should be exposed to the radioactive labeling substance contained in neighboring spots, or electron beams released from the radioactive labeling substance contained in the individual spots are scattered and mixed with the electron beams released from the radioactive labeling substance contained in neighboring spots and then impinge on regions of the stimulable phosphor layer to generate noise in biochemical analysis data produced by photoelectrically detecting stimulated emission and to lower the accuracy of biochemical analysis when a substance derived from a living organism is analyzed by quantifying the radiation amount of each spot. The accuracy of biochemical analysis is markedly degraded when spots are formed closely to each other at high density.

In order to solve these problems by preventing noise caused by the scattering of electron beams released from radioactive labeling substance contained in neighboring spots, it is inevitably required to increase the distance between neighboring spots and this makes the density of the spots lower and the test efficiency lower.

Further, in the field of biochemical analysis, it is often required to analyze a substance derived from a living organism by specifically binding, using a hybridization method or the like, specific binding substances spot-like formed at different positions on the surface of a carrier such as a membrane filter or the like, which can specifically bind with a substance derived from a living organism such as a hormone, tumor marker, enzyme, antibody, antigen, abzyme, other protein, a nuclear acid, cDNA, DNA, RNA or the like and whose sequence, base length, composition and the like are known, with a substance derived from a living organism labeled with, in addition to a radioactive labeling substance, a labeling substance which generates chemiluminescent emission when it contacts a chemiluminescent substrate and/or a fluorescent substance, and after exposing a stimulable phosphor layer to the radioactive labeling substance or prior to exposing a stimulable phosphor layer to the radioactive labeling substance, causing it to contact a chemiluminescent substrate, thereby photoelectrically detecting the chemiluminescent emission in the wavelength of visible light, and/or irradiating it with a stimulating ray, thereby photoelectrically detecting fluorescence released from a fluorescent substance. In these cases, chemiluminescent emission or fluorescence released from spots is scattered in the carrier such as a membrane filter or chemiluminescent emission or fluorescence released from any particular spot is scattered and mixed with chemiluminescent emission or fluorescence released from neighboring spots, thereby generating noise in biochemical analysis data produced by photoelectrically detecting chemiluminescent emission and/or fluorescence.

SUMMARY OF THE INVENTION

It is therefore an object of the present invention to provide a biochemical analysis unit which can prevent noise caused by the scattering of electron beams released from a radioactive labeling substance from being generated in biochemical analysis data even in the case of forming spots of specific binding substances on the surface of a carrier at high density, which can specifically bind with a substance derived from a living organism and whose sequence, base length, composition and the like are known, specifically binding the spot-like specific binding substance with a substance derived from a living organism and labeled with a radioactive substance to selectively label the spot-like specific binding substances with a radioactive substance, thereby obtaining a biochemical analysis unit, superposing the thus obtained biochemical analysis unit and a stimulable phosphor layer, exposing the stimulable phosphor layer to the radioactive labeling substance, irradiating the stimulable phosphor layer with a stimulating ray to excite the stimulable phosphor, photoelectrically detecting the stimulated emission released from the stimulable phosphor layer to produce biochemical analysis data, and analyzing the substance derived from a living organism.

It is another object of the present invention to provide a biochemical analysis unit which can prevent noise caused by the scattering of chemiluminescent emission and/or fluorescence released from a labeling substance which generates chemiluminescent emission when it contacts a chemiluminescent substrate and/or a fluorescent substance from being generated in biochemical analysis data even in the case of forming spots of specific binding substances on the surface of a carrier at high density, which can specifically bind with a substance derived from a living organism and whose sequence, base length, composition and the like are known, specifically binding the spot-like specific binding substance with a substance derived from a living organism and labeled with, in addition to a radioactive labeling substance or instead of a radioactive labeling substance, a labeling substance which generates chemiluminescent emission when it contacts a chemiluminescent substrate and/or a fluorescent substance to selectively label the spot-like specific binding substances therewith, thereby obtaining a biochemical analysis unit, photoelectrically detecting chemiluminescent emission and/or fluorescence released from the biochemical analysis unit to produce biochemical analysis data, and analyzing the substance derived from a living organism.

It is a further object of the present invention to provide a biochemical analyzing method which can effect quantitative biochemical analysis with high accuracy by producing biochemical analysis data based on a biochemical analysis unit obtained by forming spots of specific binding substances on the surface of a carrier at high density, which can specifically blind with a substance derived from a living organism and whose sequence, base length, composition and the like are known, specifically binding the spot-like specific binding substances with a substance derived from a living organism and labeled with a radioactive labeling substance, a labeling substance which generates chemiluminescent emission when it contacts a chemiluminescent substrate and/or a fluorescent substance, thereby selectively labeling the spot-like specific binding substances therewith.

The above other objects of the present invention can be accomplished by a biochemical analysis unit comprising a substrate made of a material capable of attenuating radiation energy and/or light energy and formed with a plurality of holes, and a plurality of absorptive regions formed by forming an absorptive region in every hole.

In one mode of use of the biochemical analysis unit according to this aspect of the present invention, specific binding substances, which can specifically bind with a substance derived from a living organism and whose sequence, base length, composition and the like are known, are spotted in the absorption regions in a number of the holes formed in the biochemical analysis unit at a high density and a substance derived from a living organism and labeled with a radioactive substance is specifically bound with the specific binding substances, thereby selectively labeling the plurality of absorptive regions therewith. The biochemical analysis unit is then disposed so as to face a stimulable phosphor layer, thereby exposing the stimulable phosphor layer to the radioactive labeling substance contained in the plurality of absorptive regions. Since the substrate of the biochemical analysis unit is made of a material capable of attenuating radiation energy, electron beams (β rays) released from the radioactive labeling substance contained in the individual absorptive regions are reliably prevented from being scattered in the substrate and advancing to regions of the stimulable phosphor layer that should be exposed to electron beams released from absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy.

In another mode of use of the biochemical analysis unit according to this aspect of the present invention, specific binding substances, which can specifically bind with a substance derived from a living organism and whose sequence, base length, composition and the like are known, are spotted in absorption regions in a number of holes formed in a biochemical analysis unit at a high density and a substance derived from a living organism and labeled with a labeling substance which generates chemiluminescent emission when it contacts a chemiluminescent substrate and/or a fluorescent substance, instead of with a radioactive labeling substance, thereby selectively labeling the plurality of absorptive regions therewith. Biochemical data are then produced by photoelectrically detecting chemiluminescent emission generated by the contact of a chemiluminescent substrate and the labeling substance and/or fluorescence released from the fluorescent substance in response to irradiation by a stimulating ray. Since the substrate of the biochemical analysis unit is made of a material capable of attenuating radiation energy, it is possible to reliably prevent chemiluminescent emission and/or fluorescence from being scattered in the substrate and, therefore, it is possible to efficiently prevent noise caused by the scattering of chemiluminescent emission and/or fluorescence from being generated in biochemical analysis data produced by photoelectrically detecting chemiluminescent emission and/or fluorescence.

In another mode of use of the biochemical analysis unit according to this aspect the present invention, specific binding substances, which can specifically bind with a substance derived from a living organism and whose sequence, base length, composition and the like are known, are spotted in absorption regions in a number of holes formed in a biochemical analysis unit at a high density and a substance derived from a living organism and labeled with, in addition to a radioactive labeling substance, a labeling substance which generates chemiluminescent emission when it contacts a chemiluminescent substrate and/or a fluorescent substance, thereby selectively labeling the plurality of absorptive regions therewith. The biochemical analysis unit is then disposed so as to face a stimulable phosphor layer, thereby exposing the stimulable phosphor layer to a radioactive labeling substance contained in the plurality of absorptive regions. Since the substrate of the biochemical analysis unit is made of a material capable of attenuating radiation energy, electron beams (β rays) released from the radioactive labeling substance contained in the individual absorptive regions are reliably prevented from being scattered in the substrate and advancing to regions of the stimulable phosphor layer that should be exposed to electron beams released from absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy. On the other hand, when biochemical data are produced by photoelectrically detecting chemiluminescent emission generated by the contact of a chemiluminescent substrate and the labeling substance and/or fluorescence released from the fluorescent substance in response to irradiation by a stimulating ray, the fact that the substrate is made of a material capable of attenuating radiation energy and light energy makes it possible to reliably prevent chemiluminescent emission and/or fluorescence from being scattered in the substrate and, therefore, it is possible to efficiently prevent noise caused by the scattering of chemiluminescent emission and/or fluorescence from being generated in biochemical analysis data produced by photoelectrically detecting chemiluminescent emission and/or fluorescence.

The above and other objects of the present invention can also be accomplished by a biochemical analysis unit comprising a substrate made of a material capable of attenuating radiation energy and/or light energy and formed with a plurality of holes, and a plurality of absorptive regions formed by forming an absorptive region in every hole, the plurality of absorptive regions being selectively labeled with at least one kind of labeling substance selected from a group consisting of a radioactive labeling substance, a labeling substance which generates chemiluminescent emission when it contacts a chemiluminescent substrate and a fluorescent substance by spotting specific binding substances whose sequence, base length, composition and the like are known therein and specifically binding a substance derived from a living organism and labeled with at least one kind of said labeling substance with the specific binding substances.

In the present invention, the case where a substance derived from a living organism is labeled with a fluorescent substance as termed herein includes the case where a substance derived from a living organism is labeled with a fluorescent dye and the case where a substance derived from a living organism is labeled with a fluorescent substance obtained by combining an enzyme with a labeled specimen, contacting the enzyme and a fluorescent substrate, thereby changing the fluorescent substrate to a fluorescent substance capable of emitting fluorescent light.

According to this aspect of the present invention, the plurality of absorptive regions are selectively labeled with at least one kind of labeling substance selected from a group consisting of a radioactive labeling substance, a labeling substance which generates chemiluminescent emission when it contacts a chemiluminescent substrate and a fluorescent substance by spotting therein specific binding substances, which can specifically bind with a substance derived from a living organism and whose sequence, base length, composition and the like are known and specifically binding a substance derived from a living organism and labeled with at least one kind of said labeling substance with the specific binding substances. In this case, since the substrate is made of a material capable of attenuating radiation energy, when the biochemical analysis unit is disposed so as to face a stimulable phosphor layer, thereby exposing the stimulable phosphor layer to a radioactive labeling substance contained in the plurality of absorptive regions, electron beams (β rays) released from the radioactive labeling substance contained in the individual absorptive regions are reliably prevented from being scattered in the substrate and advancing to regions of the stimulable phosphor layer that should be exposed to electron beams released from absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy.

Further, according to this aspect of the present invention, since the substrate is made of a material capable of attenuating light energy, when biochemical data are produced by photoelectrically detecting chemiluminescent emission generated by the contact of a chemiluminescent substrate and the labeling substance and/or fluorescence released from the fluorescent substance in response to the irradiation of a stimulating ray, it is possible to reliably prevent chemiluminescent emission and/or fluorescence from being scattered in the substrate and, therefore, it is possible to efficiently prevent noise caused by the scattering of chemiluminescent emission and/or fluorescence from being generated in biochemical analysis data produced by photoelectrically detecting chemiluminescent emission and/or fluorescence.

Furthermore, according to this aspect of the present invention, the substrate is made of a material capable of attenuating radiation energy and light energy and the plurality of absorptive regions are selectively labeled with at least one kind of labeling substances selected from a group consisting of a radioactive labeling substance, a labeling substance which generates chemiluminescent emission when it contacts a chemiluminescent substrate and a fluorescent substance by spotting therein specific binding substances which can specifically bind with a substance derived from a living organism and whose sequence, base length, composition and the like are known, and specifically binding a substance derived from a living organism and labeled with at least one kind of said labeling substances with the specific binding substances. Therefore, when the biochemical analysis unit is disposed so as to face a stimulable phosphor layer, thereby exposing the stimulable phosphor layer to the radioactive labeling substance contained in the plurality of absorptive regions, electron beams (β rays) released from the radioactive labeling substance contained in the individual absorptive regions are reliably prevented from being scattered in the substrate and advancing to regions of the stimulable phosphor layer that should be exposed to electron beams released from absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy. On the other hand, when biochemical data are produced by photoelectrically detecting chemiluminescent emission generated by the contact of a chemiluminescent substrate and the labeling substance and/or fluorescence released from the fluorescent substance in response to the irradiation of a stimulating ray, the fact that the substrate is made of a material capable of attenuating radiation energy and light energy makes it possible to reliably prevent chemiluminescent emission and/or fluorescence from being scattered in the substrate and, therefore, it is possible to efficiently prevent noise caused by the scattering of chemiluminescent emission and/or fluorescence from being generated in biochemical analysis data produced by photoelectrically detecting chemiluminescent emission and/or fluorescence. Furthermore, when biochemical data are produced by photoelectrically detecting chemiluminescent emission generated by the contact of a chemiluminescent substrate and the labeling substance and/or fluorescence released from the fluorescent substance in response to the irradiation of a stimulating ray, the fact that the substrate is made of a material capable of attenuating radiation energy and light energy makes it possible to reliably prevent chemiluminescent emission and/or fluorescence from being scattered in the substrate and, therefore, it is possible to efficiently prevent noise caused by the scattering of chemiluminescent emission and/or fluorescence from being generated in biochemical analysis data produced by photoelectrically detecting chemiluminescent emission and/or fluorescence.

In a preferred aspect of the present invention, the plurality of absorptive regions are formed by charging an absorptive material in the plurality of holes formed in the substrate.

In a preferred aspect of the present invention, each of the plurality of holes is formed as a through-hole.

In another preferred aspect of the present invention, each of the plurality of holes is formed as a recess.

In a preferred aspect of the present invention, the substrate is formed with a gripping portion by which the substrate can be gripped.

According to this preferred aspect of the present invention, since the substrate is formed with a gripping portion by which the substrate can be gripped, the biochemical analysis unit can be very easily handled when specific binding substances are spotted, during hybridization or during exposure operation.

The above and other objects of the present invention can also be accomplished by a biochemical analysis unit comprising an absorptive substrate formed of an absorptive material and a perforated plate formed with a plurality of through-holes and made of a material capable of attenuating radiation energy and light energy, the perforated plate being closely contacted with at least one surface of the absorptive substrate to form a plurality of absorptive regions of the absorptive substrate in the plurality of through-holes formed in the perforated plate.

In one mode of use of the biochemical analysis unit according to this aspect of the present invention, specific binding substances, which can specifically bind with a substance derived from a living organism and whose sequence, base length, composition and the like are known, are spotted in the plurality of absorption regions formed in the absorptive substrate in the plurality of through-holes of the perforated plate at a high density and a substance derived from a living organism and labeled with a radioactive substance is specifically bound with the specific binding substances, thereby selectively labeling the specific binding substances therewith. The absorptive substrate is the disposed so as to face a stimulable phosphor layer via the perforated plate, thereby exposing the stimulable phosphor layer to the radioactive labeling substance contained in the plurality of absorptive regions. Since the perforated plate is made of a material capable of attenuating radiation energy, electron beams (β rays) released from the radioactive labeling substance contained in the individual absorptive regions and electron beams released from neighboring absorptive regions can be reliably separated by the perforated plate, thereby reliably preventing electron beams released from the radioactive labeling substance contained in the individual absorptive regions from advancing to regions of the stimulable phosphor layer that should be exposed to electron beams released from neighboring absorptive regions. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy.

In another mode of use of the biochemical analysis unit according to this aspect of the present invention, specific binding substances, which can specifically bind with a substance derived from a living organism and whose sequence, base length, composition and the like are known, are spotted in the plurality of absorption regions formed in the absorptive substrate in the plurality of through-holes of the perforated plate at a high density and a substance derived from a living organism and labeled with a labeling substance capable of generating chemiluminescent emission when it contacts a chemiluminescent substrate and/or a fluorescent substance, thereby selectively labeling the specific binding substances therewith. Biochemical analysis data are then produced by photoelectrically detecting chemiluminescent emission generated by bringing a chemiluminescent substrate into contact with the absorptive substrate via the perforated plate and/or fluorescence released from the fluorescent substance in response to irradiation by a stimulating ray via the perforated plate. Since the perforated plate is made of a material capable of attenuating light energy, chemiluminescent emission and/or fluorescence released from the individual absorptive regions and chemiluminescent emission and/or fluorescence released from neighboring absorptive regions can be reliably separated by the perforated plate, thereby reliably preventing chemiluminescent emission and/or fluorescence released from the individual absorptive regions from being scattered. Therefore, it is possible to efficiently prevent noise caused by the scattering of chemiluminescent emission and/or fluorescence from being generated in biochemical analysis data produced by photoelectrically detecting chemiluminescence emission and/or fluorescence.

In another mode of use of the biochemical analysis unit according to this aspect of the invention, specific binding substances, which can specifically bind with a substance derived from a living organism and whose sequence, base length, composition and the like are known, are spotted in the absorption regions formed in the plurality of absorptive substrate in the plurality of through-holes of the perforated plate at a high density and a substance derived from a living organism and labeled with at least one kind of labeling substance selected from a group consisting of a radioactive labeling substance, a labeling substance capable of generating chemiluminescent emission when it contacts a chemiluminescent substrate and/or a fluorescent substance, thereby selectively labeling the specific binding substances therewith. The absorptive substrate is then disposed so as to face a stimulable phosphor layer via the perforated plate, thereby exposing the stimulable phosphor layer to a radioactive labeling substance contained in the plurality of absorptive regions. Since the perforated plate is made of a material capable of attenuating radiation energy and light energy, electron beams ($\beta$ rays) released from the radioactive labeling substance contained in the individual absorptive regions and electron beams released from neighboring absorptive regions can be reliably separated by the perforated plate, thereby reliably preventing electron beams released from the radioactive labeling substance contained in the individual absorptive regions from advancing to regions of the stimulable phosphor layer that should be exposed to electron beams released from neighboring absorptive regions. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to produce biochemical analysis data having a high quantitative accuracy. On the other hand, when biochemical analysis data are produced by photoelectrically detecting chemiluminescent emission generated by bringing a chemiluminescent substrate into contact with the absorptive substrate via the perforated plate and/or fluorescence released from the fluorescent substance in response to irradiation by a stimulating ray via the perforated plate, since the perforated plate is made of a material capable of attenuating radiation energy and light energy, chemiluminescent emission and/or fluorescence released from the individual absorptive regions and chemiluminescent emission and/or fluorescence released from neighboring absorptive regions can be reliably separated by the perforated plate, thereby reliably preventing chemiluminescent emission and/or fluorescence released from the individual absorptive regions from being scattered. Therefore, it is possible to efficiently prevent noise caused by the scattering of chemiluminescent emission and/or fluorescence from being generated in biochemical analysis data produced by photoelectrically detecting chemiluminescence emission and/or fluorescence.

In a preferred aspect of the present invention, perforated plates are in close contact with the both surfaces of the absorptive substrate.

According to this preferred aspect of the present invention, since perforated plates are in close contact with the both surfaces of the absorptive substrate, the strength of the biochemical analysis unit can be improved.

In a preferred aspect of the present invention, the perforated plate is formed with a gripping portion by which the perforated plate can be gripped.

According to this preferred aspect of the present invention, since the perforated plate is formed with a gripping portion by which the perforated plate can be gripped, the biochemical analysis unit can be very easily handled when specific binding substances are spotted, during hybridization or during exposure operation.

In a preferred aspect of the present invention, the specific binding substances are spotted through the plurality of through-holes in the plurality of absorptive regions formed on the absorptive substrate.

In a preferred aspect of the present invention, the plurality of absorptive regions are selectively labeled with at least one kind of labeling substances selected from a group consisting of a radioactive labeling substance, a labeling substance capable of generating chemiluminescent emission when it contacts a chemiluminescent substrate and/or a fluorescent substance by spotting specific binding substances whose sequence, base length, composition and the like are known therein and hybridizing a substance derived from a living organism and labeled with at least one kind of labeling substance with the specific binding substances.

The above and other objects of the present invention can also be accomplished by a biochemical analyzing method comprising the steps of preparing a biochemical analysis unit by spotting specific binding substances, which can specifically bind with a substance derived from a living organism and whose sequence, base length, composition and the like are known, in a plurality of absorptive regions, each of which is formed in a plurality of holes formed in a substrate made of a material capable of attenuating radiation energy and specifically binding a substance derived from a living organism and labeled with a radioactive labeling substance with the specific binding substances, superposing the biochemical analysis unit on a stimulable phosphor sheet in which a stimulable phosphor layer is formed so that the stimulable phosphor layer faces the plurality of absorptive regions, thereby exposing the stimulable phosphor layer to the radioactive labeling substance contained in the plurality of absorptive regions, irradiating the stimulable phosphor layer exposed to the radioactive labeling substance with a stimulating ray, thereby exciting stimulable phosphor contained in the stimulable phosphor layer, photoelectrically detecting stimulated emission released from the stimulable phosphor contained in the stimulable phosphor layer, thereby producing biochemical analysis data, and effecting biochemical analysis based on the biochemical analysis data.

According to this aspect of the present invention, the biochemical analysis unit is prepared by spotting specific binding substances, which can specifically bind with a substance derived from a living organism and whose sequence, base length, composition and the like are known, in a plurality of absorptive regions formed in a plurality of holes formed in a substrate made of a material capable of attenuating radiation energy and specifically binding a substance derived from a living organism and labeled with a radioactive labeling substance with the specific binding substances, thereby selectively labeling the plurality of absorptive regions. The biochemical analysis unit is then superposed on a stimulable phosphor sheet in which a stimulable phosphor layer is formed so that the stimulable phosphor layer faces the plurality of absorptive regions, thereby exposing the stimulable phosphor layer to the radioactive labeling substance contained in the plurality of absorptive regions. Since the substrate of the biochemical analysis unit is made of a material capable of attenuating radiation energy, electron beams (β rays) released from the radioactive labeling substance contained in the individual absorptive regions are reliably prevented from being scattered in the substrate and scattered electron beams are prevented from advancing to regions of the stimulable phosphor layer that should be exposed to electron beams released from the radioactive labeling substance contained absorptive regions formed in neighboring holes. Therefore, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and to effect biochemical analysis with high quantitative accuracy.

In a preferred aspect of the present invention, the plurality of absorptive regions are formed by charging an absorptive material in the plurality of holes formed in the substrate of the biochemical analysis unit.

In a preferred aspect of the present invention, the plurality of holes formed in the substrate of the biochemical analysis unit are constituted as through-holes.

In another preferred aspect of the present invention, the plurality of holes formed in the substrate of the biochemical analysis unit are constituted as recesses.

In a preferred aspect of the present invention, a plurality of dot-like stimulable phosphor layer regions are formed spaced-apart from each other in the stimulable phosphor sheet in the same pattern as that of the plurality of holes formed in the substrate of the biochemical analysis unit and the biochemical analysis unit and the stimulable phosphor sheet are superposed on each other so that each of the plurality of dot-like stimulable phosphor layer regions faces one of the plurality of absorptive regions in the plurality of holes formed in the substrate of the biochemical analysis unit, thereby exposing the plurality of dot-like stimulable phosphor layer regions of the stimulable phosphor sheet to the radioactive labeling substance contained in the plurality of absorptive regions.

According to this preferred aspect of the present invention, the plurality of dot-like stimulable phosphor layer regions are formed spaced-apart in the stimulable phosphor sheet in the same pattern as that of the plurality of holes formed in the substrate of the biochemical analysis unit and the biochemical analysis unit and the stimulable phosphor sheet are superposed on each other so that each of the plurality of dot-like stimulable phosphor layer regions faces one of the absorptive regions in the plurality of holes formed in the substrate of the biochemical analysis unit, thereby exposing the plurality of dot-like stimulable phosphor layer regions of the stimulable phosphor sheet to the radioactive labeling substance contained in the plurality of absorptive regions. It is therefore possible to reliably prevent electron beams released from the radioactive labeling substance contained in the individual absorptive regions from being scattered and advancing to the dot-like stimulable phosphor layer regions facing neighboring absorptive regions. Therefore, the plurality of dot-like stimulable phosphor layer regions formed in the stimulable phosphor sheet can be reliably exposed to the radioactive labeling substance contained in corresponding absorptive regions, thereby improving the quantitative accuracy of biochemical analysis.

In a preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with a fluorescent substance, in addition to a radioactive labeling substance, with the specific binding substances, thereby selectively labeling the plurality of absorptive regions, irradiating the biochemical analysis unit with a stimulating ray, thereby stimulating the fluorescent substance, and photoelectrically detecting fluorescence released from the fluorescent substance.

According to this preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with a fluorescent substance, in addition to a radioactive labeling substance, with the specific binding substances, thereby selectively labeling the plurality of absorptive regions, irradiating the biochemical analysis unit with a stimulating ray, thereby stimulating the fluorescent substance, and photoelectrically detecting fluorescence released from the fluorescent substance. A specimen can therefore be labeled with a fluorescent substance in addition to a radioactive labeling substance and, therefore, the utility of biochemical analysis can be improved.

In a preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with a labeling substance which generates chemiluminescent emission when it contacts a chemiluminescent substrate, in addition to a radioactive labeling substance, with the specific binding substances, thereby selectively labeling the plurality of absorptive regions, bringing the biochemical analysis unit into contact with a chemiluminescent substrate, and photoelectrically detecting chemiluminescent emission released from the labeling substance.

According to this preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with a labeling substance which generates chemiluminescent emission when it contacts a chemiluminescent substrate, in addition to a radioactive labeling substance, with the specific binding substances, thereby selectively labeling the plurality of absorptive regions, bringing the biochemical analysis unit into contact with a chemiluminescent substrate, and photoelectrically detecting chemiluminescent emission released from the labeling substance. A specimen can therefore be labeled with a labeling substance capable of generating chemiluminescent emission when it contacts a chemiluminescent substrate in addition to a radioactive labeling substance and, therefore, the utility of biochemical analysis can be improved.

In a preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a fluorescent substance and a labeling substance which generates chemiluminescent emission when it contacts a chemiluminescent substrate with the specific binding substances, thereby selectively labeling the plurality of absorptive regions, irradiating the biochemical analysis unit with a stimulating ray to stimulate the fluorescent substance, and photoelectrically detecting fluorescence released from the fluorescent substance, while bringing the biochemical analysis unit into contact with a chemiluminescent substrate, and photoelectrically detecting chemiluminescent emission released from the labeling substance.

According to this preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a fluorescent substance and a labeling substance which generates chemiluminescent emission when it contacts a chemiluminescent substrate with the specific binding substances, thereby selectively labeling the plurality of absorptive regions, irradiating the biochemical analysis unit with a stimulating ray to stimulate the fluorescent substance, and photoelectrically detecting fluorescence released from the fluorescent substance, while bringing the biochemical analysis unit into contact with a chemiluminescent substrate, and photoelectrically detecting chemiluminescent emission released from the labeling substance. A specimen can therefore be labeled with a fluorescent substance and a labeling substance capable of generating chemiluminescent emission when it contacts a chemiluminescent substrate, in addition to a radioactive labeling substance, and, therefore, the utility of biochemical analysis can be improved.

The above and other objects of the present invention can be also accomplished by a biochemical analyzing method comprising the steps of preparing a biochemical analysis unit comprising an absorptive substrate formed of an absorptive material and a perforated plate made of a material capable of attenuating radiation energy and light energy and formed with a plurality of through-holes, the perforated plate being closely contacted with at least one surface of the absorptive substrate to form a plurality of absorptive regions of the absorptive substrate in the plurality of through-holes formed in the perforated plate, the plurality of absorptive regions being selectively labeled with a radioactive labeling substance by spotting specific binding substances, which can specifically bind with a substance derived from a living organism and whose sequence, base length, composition and the like are known, in the plurality of absorptive regions and specifically binding a substance derived from a living organism and labeled with a radioactive labeling substance, superposing the biochemical analysis unit and a stimulable phosphor sheet in which a stimulable phosphor layer is formed via the perforated plate so that the stimulable phosphor layer faces the plurality of absorptive regions, thereby exposing the stimulable phosphor layer to the radioactive labeling substance contained in the plurality of absorptive regions, irradiating the stimulable phosphor layer exposed to the radioactive labeling substance with a stimulating ray to excite stimulable phosphor contained in the stimulable phosphor layer, photoelectrically detecting stimulated emission released from the stimulable phosphor contained in the stimulable phosphor layer to produce biochemical analysis data, and effecting biochemical analysis based on the biochemical analysis data.

According to this aspect of the present invention, a biochemical analyzing method comprises the steps of preparing a biochemical analysis unit comprising an absorptive substrate formed of an absorptive material and a perforated plate made of a material capable of attenuating radiation energy and light energy and formed with a plurality of through-holes, the perforated plate being closely contacted with at least one surface of the absorptive substrate so that a plurality of absorptive regions are formed of the absorptive substrate in the plurality of the through-holes formed in the perforated plate, the plurality of absorptive regions being selectively labeled with a radioactive labeling substance by spotting specific binding substances, which can specifically bind with a substance derived from a living organism and whose sequence, base length, composition and the like are known, in the plurality of absorptive regions and specifically binding a substance derived from a living organism and labeled with a radioactive labeling substance, superposing the biochemical analysis unit and a stimulable phosphor sheet in which a stimulable phosphor layer is formed via the perforated plate so that the stimulable phosphor layer faces the plurality of absorptive regions, thereby exposing the stimulable phosphor layer to the radioactive labeling substance contained in the plurality of absorptive regions, irradiating the stimulable phosphor layer exposed to the radioactive labeling substance with a stimulating ray to excite stimulable phosphor contained in the stimulable phosphor layer, photoelectrically detecting stimulated emission released from the stimulable phosphor contained in the stimulable phosphor layer to produce biochemical analysis data, and effecting biochemical analysis based on the biochemical analysis data. Therefore, since electron beams ($\beta$ rays) released from the radioactive labeling substance contained in the individual absorptive regions and electron beams released from neighboring absorptive regions can be reliably separated by the perforated plate, thereby reliably preventing electron beams released from the radioactive labeling substance contained in the individual absorptive regions from advancing to regions of the stimulable phosphor layer that should be exposed to electron beams released from neighboring absorptive regions, it is possible to efficiently prevent noise caused by the scattering of electron beams released from the radioactive labeling substance from being generated in biochemical analysis data produced by irradiating the stimulable phosphor layer exposed to the radioactive labeling substance with a stimulating ray and photoelectrically detecting stimulated emission released from the stimulable phosphor layer and produce biochemical analysis data having high quantitative accuracy.

In a preferred aspect of the present invention, perforated plates are closely contacted with both surfaces of the absorptive substrate, thereby forming the biochemical analysis unit, and biochemical analysis data are produced by superposing the biochemical analysis unit and the stimulable phosphor sheet via one of the perforated plates so that the stimulable phosphor layer faces the plurality of absorptive regions and exposing the stimulable phosphor layer to a radioactive labeling substance contained in the plurality of absorptive regions.

In a preferred aspect of the present invention, the specific binding substances are spotted through the plurality of through-holes in the plurality of absorptive regions formed on the absorptive substrate.

In a preferred aspect of the present invention, a plurality of dot-like stimulable phosphor layer regions are formed spaced-apart in the stimulable phosphor sheet in the same pattern as that of the plurality of through-holes formed in the perforated plate, and the biochemical analysis unit and the stimulable phosphor sheet are superposed on each other so that each of the plurality of dot-like stimulable phosphor layer regions faces one of the plurality of absorptive regions via one of the through-holes formed in the perforated plate, thereby exposing the plurality of dot-like stimulable phosphor layer regions to a radioactive labeling substance contained in the plurality of absorptive regions.

According to this preferred aspect of the present invention, a plurality of dot-like stimulable phosphor layer regions are formed spaced-apart in the stimulable phosphor sheet in the same pattern as that of the plurality of through-holes formed in the perforated plate, and the biochemical analysis unit and the stimulable phosphor sheet are superposed on each other so that each of the plurality of dot-like stimulable phosphor layer regions faces one of the plurality of absorptive regions via one of the through-holes formed in the perforated plate, thereby exposing the plurality of dot-like stimulable phosphor layer regions to a radioactive labeling substance contained in the plurality of absorptive regions. Electron beams ($\beta$ rays) released from a radioactive labeling substance contained in the individual absorptive regions are therefore prevented from being scattered in the substrate and scattered electron beams are prevented from advancing to the dot-like stimulable phosphor layer regions facing neighboring absorptive regions. Therefore, the plurality of dot-like stimulable phosphor layer regions formed in the stimulable phosphor sheet can be reliably exposed to the radioactive labeling substance contained in corresponding absorptive regions, thereby improving the quantitative accuracy of biochemical analysis.

In a preferred aspect of the present invention, the perforated plate is made of a material capable of attenuating radiation energy and light energy, and the biochemical analysis is effected based on biochemical analysis data produced by the steps of preparing the biochemical analysis unit by specifically binding a substance derived from a living organism and labeled with a fluorescent substance, in addition to a radioactive labeling substance, with the specific binding substances, thereby selectively labeling the plurality of absorptive regions, irradiating the biochemical analysis unit with a stimulating ray through the plurality of the through-holes formed in the perforated plate, thereby stimulating the fluorescent substance, and photoelectrically detecting fluorescence released from the fluorescent substance.

According to this preferred aspect of the present invention, the perforated plate is made of a material capable of attenuating radiation energy and light energy, and the biochemical analysis is effected based on biochemical analysis data produced by the steps of preparing the biochemical analysis unit by specifically binding a substance derived from a living organism and labeled with a fluorescent substance, in addition to a radioactive labeling substance, with the specific binding substances, thereby selectively labeling the plurality of absorptive regions, irradiating the biochemical analysis unit with a stimulating ray through the plurality of the through-holes formed in the perforated plate, thereby stimulating the fluorescent substance, and photoelectrically detecting fluorescence released from the fluorescent substance. A specimen can therefore be labeled with a fluorescent substance in addition to a radioactive labeling substance and, therefore, the utility of biochemical analysis can be improved.

In a preferred aspect of the present invention, the perforated plate is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a labeling substance which generates chemiluminescent emission when it contacts a chemiluminescent substrate with the specific binding substances, thereby selectively labeling the plurality of absorptive regions, bringing the biochemical analysis unit into close contact with a chemiluminescent substrate through the plurality of the through-holes formed in the perforated plate, and photoelectrically detecting chemiluminescent emission released from the labeling substance.

According to this preferred aspect of the present invention, the substrate of the biochemical analysis unit is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a labeling substance which generates chemiluminescent emission when it contacts a chemiluminescent substrate with the specific binding substances, thereby selectively labeling the plurality of absorptive regions, bringing the biochemical analysis unit into close contact with a chemiluminescent substrate through the plurality of the through-holes formed in the perforated plate, and photoelectrically detecting chemiluminescent emission released from the labeling substance. A specimen can therefore be labeled with a labeling substance capable of generating chemiluminescent emission when it contacts a chemiluminescent substrate, in addition to a radioactive labeling substance, and, therefore, the utility of biochemical analysis can be improved.

In a preferred aspect of the present invention, the perforated plate is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a fluorescent substance and a labeling substance which generates chemiluminescent emission when it contacts a chemiluminescent substrate with the specific binding substances, thereby selectively labeling the plurality of absorptive regions, irradiating the biochemical analysis unit with a stimulating ray through the plurality of the through-holes formed in the perforated plate to stimulate the fluorescent substance, and photoelectrically detecting fluorescence released from the fluorescent substance, while bringing the biochemical analysis unit into close contact with a chemiluminescent substrate through the plurality of the through-holes formed in the perforated plate, and photoelectrically detecting chemiluminescent emission released from the labeling substance.

According to this preferred aspect of the present invention, the perforated plate is made of a material capable of attenuating radiation energy and light energy, and the biochemical analysis is effected based on biochemical analysis data produced by the steps of preparing the biochemical analysis unit by specifically binding a substance derived from a living organism and labeled with, in addition to a radioactive labeling substance, a fluorescent substance and a labeling substance which generates chemiluminescent emission when it contacts a chemiluminescent substrate with the specific binding substances, thereby selectively labeling the plurality of absorptive regions, irradiating the biochemical analysis unit with a stimulating ray through the plurality of the through-holes formed in the perforated plate to stimulate the fluorescent substance, and photoelectrically detecting fluorescence released from the fluorescent substance, while bringing the biochemical analysis unit into close contact with a chemiluminescent substrate through the plurality of the through-holes formed in the perforated plate, and photoelectrically detecting chemiluminescent emission released from the labeling substance. A specimen can therefore be labeled with a fluorescent substance and a labeling substance capable of generating chemiluminescent emission when it contacts a chemiluminescent substrate, in addition to a radioactive labeling substance, and, therefore, the utility of biochemical analysis can be improved.

The above and other objects of the present invention can also be accomplished by a biochemical analyzing method comprising the steps of preparing a biochemical analysis unit by spotting specific binding substances, which can specifically bind with a substance derived from a living organism and whose sequence, base length, composition and the like are known, in a plurality of absorptive regions formed in a plurality of holes formed in a substrate made of a material capable of attenuating light energy and specifically binding a substance derived from a living organism and labeled with a fluorescent substance with the specific binding substances, thereby selectively labeling a plurality of absorptive regions, irradiating the biochemical analysis unit with a stimulating ray, thereby exciting the fluorescent substance, photoelectrically detecting fluorescence released from the fluorescent substance, thereby producing biochemical analysis data, and effecting biochemical analysis based on the biochemical analysis data.

According to this aspect of the present invention, the biochemical analysis unit is prepared by spotting specific binding substances, which can specifically bind with a substance derived from a living organism and whose sequence, base length, composition and the like are known, in a plurality of absorptive regions formed in a plurality of holes formed in a substrate made of a material capable of attenuating radiation energy and specifically binding a substance derived from a living organism and labeled with a fluorescent substance with the specific binding substances, thereby selectively labeling a plurality of absorptive regions. Biochemical analysis data are then produced by irradiating the biochemical analysis unit with a stimulating ray to stimulate the fluorescent substance and photoelectrically detecting fluorescence released from the fluorescent substance and biochemical analysis is effected based on the biochemical analysis data. Therefore, when the biochemical data are produced by irradiating the biochemical analysis unit with a stimulating ray and photoelectrically detecting fluorescence released from the fluorescent substance, since fluorescence is reliably prevented from being scattered in the substrate of the biochemical analysis unit, it is possible to efficiently prevent noise caused by the scattering of fluorescence from being generated in biochemical analysis data produced by photoelectrically detecting fluorescence and to effect biochemical analysis with high quantitative accuracy.

In a preferred aspect of the present invention, the plurality of absorptive regions are formed by charging an absorptive material in the plurality of holes formed in the substrate of the biochemical analysis unit.

In a preferred aspect of the present invention, the plurality of holes formed in the substrate of the biochemical analysis unit are constituted as through-holes.

In another preferred aspect of the present invention, the plurality of holes formed in the substrate of the biochemical analysis unit are constituted as recesses.

The above and other objects of the present invention can also be accomplished by a biochemical analyzing method comprising the steps of preparing a biochemical analysis unit by spotting specific binding substances, which can specifically bind with a substance derived from a living organism and whose sequence, base length, composition and the like are known, in a plurality of absorptive regions formed in a plurality of holes formed in a substrate made of a material capable of attenuating light energy and specifically binding a substance derived from a living organism and labeled with a labeling substance capable of generating chemiluminescent emission when it contacts a chemiluminescent substrate with the specific binding substances, thereby selectively labeling the plurality of absorptive regions, bringing the biochemical analysis unit into close contact with a chemiluminescent substrate, photoelectrically detecting chemiluminescent emission released from the labeling substance, thereby producing biochemical analysis data, and effecting biochemical analysis based on the biochemical analysis data.

According to this aspect of the present invention, the biochemical analysis unit is prepared by spotting specific binding substances, which can specifically bind with a substance derived from a living organism and whose sequence, base length, composition and the like are known, in a plurality of absorptive regions formed in a plurality of holes formed in a substrate made of a material capable of attenuating radiation energy and specifically binding a substance derived from a living organism and labeled with a labeling substance capable of generating chemiluminescent emission when it contacts a chemiluminescent substrate with the specific binding substances, thereby selectively labeling the plurality of absorptive regions. Biochemical analysis data are the produced by bringing the biochemical analysis unit into close contact with a chemiluminescent substrate and photoelectrically detecting chemiluminescent emission released from the labeling substance and biochemical analysis is effected based on the biochemical analysis data. Therefore, when the biochemical data are produced by bringing the biochemical analysis unit into close contact with a chemiluminescent substrate and photoelectrically detecting chemiluminescent emission released from the labeling substance, since chemiluminescent emission is reliably prevented from being scattered in the substrate of the biochemical analysis unit, it is possible to efficiently prevent noise caused by the scattering of chemiluminescent emission from being generated in biochemical analysis data produced by photoelectrically detecting chemiluminescent emission and effect biochemical analysis with high quantitative accuracy.

In a preferred aspect of the present invention, the plurality of absorptive regions are formed by charging an absorptive material in the plurality of holes formed in the substrate of the biochemical analysis unit.

In a preferred aspect of the present invention, the plurality of holes formed in the substrate of the biochemical analysis unit are constituted as through-holes.

In another preferred aspect of the present invention, the plurality of holes formed in the substrate of the biochemical analysis unit are constituted as recesses.

The above and other objects of the present invention can also be accomplished by a biochemical analyzing method comprising the steps of preparing a biochemical analysis unit by spotting specific binding substances, which can specifically bind with a substance derived from a living organism and whose sequence, base length, composition and the like are known, in a plurality of absorptive regions formed in a plurality of holes formed in a substrate made of a material capable of attenuating light energy and specifically binding a substance derived from a living organism and labeled with a fluorescent substance and a labeling substance capable of generating chemiluminescent emission when it contacts a chemiluminescent substrate with the specific binding substances, thereby selectively labeling the plurality of absorptive regions, irradiating the biochemical analysis unit with a stimulating ray to excite the fluorescent substance, and photoelectrically detecting fluorescence released from the fluorescent substance, thereby producing biochemical analysis data, while bringing the biochemical analysis unit into close contact with a chemiluminescent substrate, photoelectrically detecting chemiluminescent emission released from the labeling substance, thereby producing biochemical analysis data, and effecting biochemical analysis based on the biochemical analysis data.

According to this aspect of the present invention, the biochemical analysis unit is prepared by spotting specific binding substances, which can specifically bind with a substance derived from a living organism and whose sequence, base length, composition and the like are known, in a plurality of absorptive regions formed in a plurality of holes formed in a substrate made of a material capable of attenuating radiation energy and specifically binding a substance derived from a living organism and labeled with a fluorescent substance and a labeling substance capable of generating chemiluminescent emission when it contacts a chemiluminescent substrate with the specific binding substances, thereby selectively labeling the plurality of absorptive regions. Biochemical analysis data are then produced by irradiating the biochemical analysis unit with a stimulating ray to stimulate the fluorescent substance and photoelectrically detecting fluorescence released from the fluorescent substance and are also produced by bringing the biochemical analysis unit into close contact with a chemiluminescent substrate and photoelectrically detecting chemiluminescent emission released from the labeling substance, and biochemical analysis is effected based on the biochemical analysis data. Therefore, when the biochemical data are produced by reading fluorescent data, since fluorescence is reliably prevented from being scattered in the substrate of the biochemical analysis unit, it is possible to efficiently prevent noise caused by the scattering of fluorescence from being generated in biochemical analysis data produced by photoelectrically detecting fluorescence. On the other hand, when the biochemical data are produced by reading chemiluminescent data, since chemiluminescent emission is reliably prevented from being scattered in the substrate of the biochemical analysis unit, it is possible to efficiently prevent noise caused by the scattering of chemiluminescent emission from being generated in biochemical analysis data produced by photoelectrically detecting chemiluminescent emission. Therefore, biochemical analysis can be effected with high quantitative accuracy.

In a preferred aspect of the present invention, the plurality of absorptive regions are formed by charging an absorptive material in the plurality of holes formed in the substrate of the biochemical analysis unit.

In a preferred aspect of the present invention, the plurality of holes formed in the substrate of the biochemical analysis unit are constituted as through-holes.

In another preferred aspect of the present invention, the plurality of holes formed in the substrate of the biochemical analysis unit are constituted as recesses.

The above and other objects of the present invention can also be accomplished by a biochemical analyzing method comprising the steps of bringing an absorptive substrate made of an absorptive material and formed with a plurality of absorptive regions by spotting thereon specific binding substances, which can specifically bind with a substance derived from a living organism and whose sequence, base length, composition and the like are known, the plurality of the absorptive regions being selectively labeled by specifically binding a substance derived from a living organism and labeled with a fluorescent substance with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, irradiating the plurality of absorptive regions formed in the absorptive substrate through the plurality of through-holes formed in the perforated plate to stimulate the fluorescent substance, photoelectrically detecting fluorescence released from the fluorescent substance, thereby producing biochemical analysis data, and effecting biochemical analysis based on the biochemical analysis data.

According to this aspect of the present invention, a biochemical analyzing method comprises the steps of bringing an absorptive substrate made of an absorptive material and formed with a plurality of absorptive regions by spotting thereon specific binding substances, which can specifically bind with a substance derived from a living organism and whose sequence, base length, composition and the like are known, onto the absorptive substrate, the plurality of the absorptive regions being selectively labeled by specifically binding a substance derived from a living organism and labeled with a fluorescent substance with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, irradiating the plurality of absorptive regions formed in the absorptive substrate through the plurality of through-holes formed in the perforated plate to stimulate the fluorescent substance, photoelectrically detecting fluorescence released from the fluorescent substance, thereby producing biochemical analysis data, and effecting biochemical analysis based on the biochemical analysis data. Therefore, when biochemical analysis data are produced by irradiating the plurality of absorptive regions formed in the absorptive substrate with a stimulating ray through the plurality of through-holes formed in the perforated plate and photoelectrically detecting fluorescence released from the fluorescent substance, since fluorescence released from each of the plurality of absorptive regions can be reliably separated by the perforated plate from fluorescence released from neighboring absorptive regions, it is possible to efficiently prevent noise caused by the scattering of fluorescence from being generated in biochemical analysis data produced by photoelectrically detecting fluorescence and effect biochemical analysis with high quantitative accuracy.

In a preferred aspect of the present invention, the biochemical analysis unit is prepared by bringing perforated plates into close contact with both surfaces of the absorptive substrate and biochemical data are produced by irradiating the plurality of absorptive regions formed in the absorptive substrate with a stimulating ray through the plurality of through-holes formed in one of the perforated plates to stimulate a fluorescent substance and photoelectrically detecting fluorescence released from the fluorescent substance.

In a preferred aspect of the present invention, the specific binding substances are spotted through the plurality of through-holes formed in the perforated plate in the plurality of absorptive regions formed in the absorptive substrate.

The above and other objects of the present invention can also be accomplished by a biochemical analyzing method comprising the steps of bringing an absorptive substrate made of an absorptive material and formed with a plurality of absorptive regions by spotting thereon specific binding substances, which can specifically bind with a substance derived from a living organism and whose sequence, base length, composition and the like are known, the plurality of the absorptive regions being selectively labeled by specifically binding a substance derived from a living organism and labeled with a labeling substance capable of generating chemiluminescent emission when it contacts a chemiluminescent substrate with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, bringing a chemiluminescent substrate into close contact with the plurality of absorptive regions formed in the absorptive substrate through the plurality of through-holes formed in the perforated plate, photoelectrically detecting chemiluminescent emission released from the labeling substance, thereby producing biochemical analysis data, and effecting biochemical analysis based on the biochemical analysis data.

According to this aspect of the present invention, a biochemical analyzing method comprises the steps of bringing an absorptive substrate made of an absorptive material and formed with a plurality of absorptive regions by spotting thereon specific binding substances, which can specifically bind with a substance derived from a living organism and whose sequence, base length, composition and the like are known, onto the absorptive substrate, the plurality of the absorptive regions being selectively labeled by specifically binding a substance derived from a living organism and labeled with a labeling substance capable of generating chemiluminescent emission when it contacts a chemiluminescent substrate with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, bringing a chemiluminescent substrate into close contact with the plurality of absorptive regions formed in the absorptive substrate through the plurality of through-holes formed in the perforated plate, photoelectrically detecting chemiluminescent emission released from the labeling substance, thereby producing biochemical analysis data, and effecting biochemical analysis based on the biochemical analysis data. Therefore, when biochemical analysis data are produced by bringing a chemiluminescent substrate into close contact with the plurality of absorptive regions formed in the absorptive substrate through the plurality of through-holes formed in the perforated plate and photoelectrically detecting chemiluminescent emission released from the labeling substance, since chemiluminescent emission released from each of the plurality of absorptive regions can be reliably separated by the perforated plate from chemiluminescent emission released from neighboring absorptive regions, it is possible to efficiently prevent noise caused by the scattering of chemiluminescent emission from being generated in biochemical analysis data produced by photoelectrically detecting chemiluminescent emission and effect biochemical analysis with high quantitative accuracy.

In a preferred aspect of the present invention, the biochemical analysis unit is prepared by bringing perforated plates into close contact with the both surfaces of the absorptive substrate and biochemical data are produced by bringing a chemiluminescent substrate into close contact with the plurality of absorptive regions formed in the absorptive substrate through the plurality of through-holes formed in one of the perforated plates and photoelectrically detecting chemiluminescent emission released from the labeling substance.

In a preferred aspect of the present invention, the specific binding substances are spotted through the plurality of through-holes formed in the perforated plate in the plurality of absorptive regions formed in the absorptive substrate.

The above and other objects of the present invention can also be accomplished by a biochemical analyzing method comprising the steps of bringing an absorptive substrate made of an absorptive material and formed with a plurality of absorptive regions by spotting thereon specific binding substances, which can specifically bind with a substance derived from a living organism and whose sequence, base length, composition and the like are known, the plurality of the absorptive regions being selectively labeled by specifically binding a substance derived from a living organism and labeled with a fluorescent substance and a labeling substance capable of generating chemiluminescent emission when it contacts a chemiluminescent substrate with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, irradiating the plurality of absorptive regions formed in the absorptive substrate through the plurality of through-holes formed in the perforated plate to stimulate the fluorescent substance, and photoelectrically detecting fluorescence released from the fluorescent substance, thereby producing biochemical analysis data, while bringing a chemiluminescent substrate into close contact with the plurality of absorptive regions formed in the absorptive substrate through the plurality of through-holes formed in the perforated plate, and photoelectrically detecting chemiluminescent emission released from the labeling substance, thereby producing biochemical analysis data, and effecting biochemical analysis based on the biochemical analysis data.

According to this aspect the present invention, a biochemical analyzing method comprises the steps of bringing an absorptive substrate made of an absorptive material and formed with a plurality of absorptive regions by spotting thereon specific binding substances, which can specifically bind with a substance derived from a living organism and whose sequence, base length, composition and the like are known, the plurality of the absorptive regions being selectively labeled by specifically binding a substance derived from a living organism and labeled with a fluorescent substance and a labeling substance capable of generating chemiluminescent emission when it contacts a chemiluminescent substrate with the specific binding substances contained in the plurality of absorptive regions, into close contact with a perforated plate made of a material capable of attenuating light energy and formed with a plurality of through-holes at positions corresponding to the plurality of absorptive regions formed in the absorptive substrate, irradiating the plurality of absorptive regions formed in the absorptive substrate through the plurality of through-holes formed in the perforated plate to stimulate the fluorescent substance, and photoelectrically detecting fluorescence released from the fluorescent substance, thereby producing biochemical analysis data, while bringing a chemiluminescent substrate into close contact with the plurality of absorptive regions formed in the absorptive substrate through the plurality of through-holes formed in the perforated plate, and photoelectrically detecting chemiluminescent emission released from the labeling substance, thereby producing biochemical analysis data, and effecting biochemical analysis based on the biochemical analysis data. Therefore, when biochemical analysis data are produced by irradiating the plurality of absorptive regions formed in the absorptive substrate with a stimulating ray through the plurality of through-holes formed in the perforated plate and photoelectrically detecting fluorescence released from the fluorescent substance, since fluorescence released from each of the plurality of absorptive regions can be reliably separated by the perforated plate from fluorescence released from neighboring absorptive regions, it is possible to efficiently prevent noise caused by the scattering of fluorescence from being generated in biochemical analysis data produced by photoelectrically detecting fluorescence. On the other hand, when biochemical analysis data are produced by bringing a chemiluminescent substrate into close contact with the plurality of absorptive regions formed in the absorptive substrate through the plurality of through-holes formed in the perforated plate and photoelectrically detecting chemiluminescent emission released from the labeling substance, since chemiluminescent emission released from each of the plurality of absorptive regions can be reliably separated by the perforated plate from chemiluminescent emission released from neighboring absorptive regions, it is possible to efficiently prevent noise caused by the scattering of chemiluminescent emission from being generated in biochemical analysis data produced by photoelectrically detecting chemiluminescent emission. Therefore, biochemical analysis can be effected with high quantitative accuracy.

In a preferred aspect of the present invention, the biochemical analysis unit is prepared by bringing perforated plates into close contact with the both surfaces of the absorptive substrate and biochemical data are produced by irradiating the plurality of absorptive regions formed in the absorptive substrate with a stimulating ray through the plurality of through-holes formed in one of the perforated plates to stimulate a fluorescent substance and photoelectrically detecting fluorescence released from the fluorescent substance and are also produced by bringing a chemiluminescent substrate into close contact with the plurality of absorptive regions formed in the absorptive substrate through the plurality of through-holes formed in one of the perforated plates and photoelectrically detecting chemiluminescent emission released from the labeling substance.

In a preferred aspect of the present invention, the specific binding substances are spotted through the plurality of through-holes formed in the perforated plate in the plurality of absorptive regions formed in the absorptive substrate.

In a preferred aspect of the present invention, the substance derived from a living organism is specifically bound with specific binding substances by a reaction selected from a group consisting of hybridization, antigen-antibody reaction and receptor-ligand reaction.

In a preferred aspect of the present invention, the material capable of attenuating radiation energy has a property of reducing the energy of radiation to $1/5$ or less when the radiation travels in the material by a distance equal to that between neighboring absorptive regions.

In a further preferred aspect of the present invention, a material capable of attenuating radiation energy has a property of reducing the energy of radiation to $1/10$ or less when the radiation travels in the material by a distance equal to that between neighboring absorptive regions.

In a further preferred aspect of the present invention, a material capable of attenuating radiation energy has a property of reducing the energy of radiation to $1/50$ or less when the radiation travels in the material by a distance equal to that between neighboring absorptive regions.

In a further preferred aspect of the present invention, a material capable of attenuating radiation energy has a property of reducing the energy of radiation to $1/100$ or less when the radiation travels in the material by a distance equal to that between neighboring absorptive regions.

In a further preferred aspect of the present invention, a material capable of attenuating radiation energy has property of reducing the energy of radiation to $1/500$ or less when the radiation travels in the material by a distance equal to that between neighboring absorptive regions.

In a further preferred aspect of the present invention, a material capable of attenuating radiation energy has a property of reducing the energy of radiation to $1/1000$ or less when the radiation travels in the material by a distance equal to that between neighboring absorptive regions.

In a preferred aspect of the present invention, a material capable of attenuating light energy has a property of reducing the energy of light to $1/5$ or less when the light travels in the material by a distance equal to that between neighboring absorptive regions.

In a further preferred aspect of the present invention, a material capable of attenuating light energy has a property of reducing the energy of light to $1/10$ or less when the light travels in the material by a distance equal to that between neighboring absorptive regions.

In a further preferred aspect of the present invention, a material capable of attenuating light energy has a property of reducing the energy of light to $1/50$ or less when the light travels in the material by a distance equal to that between neighboring absorptive regions.

In a further preferred aspect of the present invention, a material capable of attenuating light energy has a property of reducing the energy of light to $1/100$ or less when the light travels in the material by a distance equal to that between neighboring absorptive regions.

In a further preferred aspect of the present invention, a material capable of attenuating light energy has a property of reducing the energy of light to 1/500 or less when the light travels in the material by a distance equal to that between neighboring absorptive regions.

In a further preferred aspect of the present invention, a material capable of attenuating light energy has a property of reducing the energy of light to 1/1000 or less when the light travels in the material by a distance equal to that between neighboring absorptive regions.

In the present invention, the material for forming the substrate or the perforated plate of the biochemical analysis unit is not particularly limited but may be of any type of inorganic compound material or organic compound material insofar as it can attenuate radiation energy and/or light energy. It is preferably formed of metal material, ceramic material or plastic material.

In the present invention, illustrative examples of inorganic compound materials capable of attenuating radiation energy and preferably usable for forming a substrate or a perforated plate of a biochemical analysis unit in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound is preferably used as an organic compound material capable of attenuating radiation energy. Illustrative examples of high molecular compounds preferably usable for forming the substrate or the perforated plate of the biochemical analysis unit in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4, 10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, in the case where the substrate or the perforated plate of the biochemical analysis unit is made of a material capable of attenuating radiation energy in accordance with the present invention, the substrate or the perforated plate of the biochemical analysis unit is preferably formed of a compound material or a composite material having specific gravity of 1.0 g/cm$^3$ or more and more preferably formed of a compound material or a composite material having specific gravity of 1.5 g/cm$^3$ to 23 g/cm$^3$.

In the present invention, illustrative examples of inorganic compound material capable of attenuating light energy and preferably usable for forming the substrate or the perforated plate of the biochemical analysis unit in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound is preferably used as an organic compound material capable of attenuating light energy. Illustrative examples of high molecular compounds preferably usable for forming a substrate or a perforated plate of a biochemical analysis unit in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4, 10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating light energy generally increases as scattering and/or absorption of light increases, in the case where the substrate or the perforated plate of the biochemical analysis unit is made of a material capable of attenuating light energy, in the present invention, the substrate or the perforated plate of the biochemical analysis unit preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T.

In the present invention, a light scattering substance or a light absorbing substance may be added to the substrate or the perforated plate of the biochemical analysis unit in order to improve the capability of attenuating light energy. Particles of a material different from a material forming the substrate or the perforated plate of the biochemical analysis unit may be preferably used as a light scattering substance and a pigment or dye may be preferably used as a light absorbing substance.

In a preferred aspect of the present invention, the substrate of the biochemical analysis unit is formed of a flexible material.

According to this preferred aspect of the present invention, since the substrate of the biochemical analysis unit is formed of a flexible material, the biochemical analysis unit can be bent and be brought into contact with a hybridization solution, thereby hybridizing specific binding substances with a substance derived from a living organism. Therefore, specific binding substances and a substance derived from a living organism can be hybridized with each other in a desired manner using a small amount of a hybridization solution.

In a preferred aspect of the present invention, the plurality of holes are regularly formed in the substrate of the biochemical analysis unit.

In a preferred aspect of the present invention, a plurality of holes having a substantially circular shape are formed in the substrate of the biochemical analysis unit.

In another preferred aspect of the present invention, a plurality of holes having a substantially rectangular shape are formed in the substrate of the biochemical analysis unit.

In a preferred aspect of the present invention, the substrate of the biochemical analysis unit is formed with 10 or more holes.

In a further preferred aspect of the present invention, the substrate of the biochemical analysis unit is formed with 50 or more holes.

In a further preferred aspect of the present invention, the substrate of the biochemical analysis unit is formed with 100 or more holes.

In a further preferred aspect of the present invention, the substrate of the biochemical analysis unit is formed with 1,000 or more holes.

In a further preferred aspect of the present invention, the substrate of the biochemical analysis unit is formed with 10,000 or more holes.

In a further preferred aspect of the present invention, the substrate of the biochemical analysis unit is formed with 100,000 or more holes.

In a preferred aspect of the present invention, each of the plurality of holes formed in the substrate of the biochemical analysis unit has a size of less than 5 $mm^2$.

In a further preferred aspect of the present invention, each of the plurality of holes formed in the substrate of the biochemical analysis unit has a size of less than 1 $mm^2$.

In a further preferred aspect of the present invention, each of the plurality of holes formed in the substrate of the biochemical analysis unit has a size of less than 0.5 $mm^2$.

In a further preferred aspect of the present invention, each of the plurality of holes formed in the substrate of the biochemical analysis unit has a size of less than 0.1 $mm^2$.

In a further preferred aspect of the present invention, each of the plurality of holes formed in the substrate of the biochemical analysis unit has a size of less than 0.05 $mm^2$.

In a further preferred aspect of the present invention, each of the plurality of holes formed in the substrate of the biochemical analysis unit has a size of less than 0.01 $mm^2$.

In the present invention, the density of the holes formed in the substrate of the biochemical analysis unit is determined depending upon the material of the substrate, the thickness of the substrate, the kind of electron beam released from a radioactive substance, the wavelength of fluorescence released from a fluorescent substance or the like.

In a preferred aspect of the present invention, the plurality of holes are formed in the substrate of the biochemical analysis unit at a density of 10 or more per $cm^2$.

In a further preferred aspect of the present invention, the plurality of holes are formed in the substrate of the biochemical analysis unit at a density of 50 or more per $cm^2$.

In a further preferred aspect of the present invention, the plurality of holes are formed in the substrate of the biochemical analysis unit at a density of 100 or more per $cm^2$.

In a further preferred aspect of the present invention, the plurality of holes are formed in the substrate of the biochemical analysis unit at a density of 500 or more per $cm^2$.

In a further preferred aspect of the present invention, the plurality of holes are formed in the substrate of the biochemical analysis unit at a density of 1,000 or more per $cm^2$.

In a further preferred aspect of the present invention, the plurality of holes are formed in the substrate of the biochemical analysis unit at a density of 5,000 or more per $cm^2$.

In a further preferred aspect of the present invention, the plurality of holes are formed in the substrate of the biochemical analysis unit at a density of 10,000 or more per $cm^2$.

In a preferred aspect of the present invention, a plurality of through-holes are regularly formed in the perforated plate of the biochemical analysis unit.

In a preferred aspect of the present invention, a plurality of through-holes having a substantially circular shape are formed in the perforated plate of the biochemical analysis unit.

In another preferred aspect of the present invention, a plurality of through-holes having a substantially rectangular shape are formed in the perforated plate of the biochemical analysis unit.

In a preferred aspect of the present invention, the perforated plate of the biochemical analysis unit is formed with 10 or more through-holes.

In a further preferred aspect of the present invention, the perforated plate of the biochemical analysis unit is formed with 50 or more through-holes.

In a further preferred aspect of the present invention, the perforated plate of the biochemical analysis unit is formed with 100 or more through-holes.

In a further preferred aspect of the present invention, the perforated plate of the biochemical analysis unit is formed with 1,000 or more through-holes.

In a further preferred aspect of the present invention, the perforated plate of the biochemical analysis unit is formed with 10,000 or more through-holes.

In a further preferred aspect of the present invention, the perforated plate of the biochemical analysis unit is formed with 100,000 or more through-holes.

In a preferred aspect of the present invention, each of the plurality of through-holes formed in the perforated plate of the biochemical analysis unit has a size of less than 5 $mm^2$.

In a further preferred aspect of the present invention, each of the plurality of through-holes formed in the perforated plate of the biochemical analysis unit has a size of less than 1 $mm^2$.

In a further preferred aspect of the present invention, each of the plurality of through-holes formed in the perforated plate of the biochemical analysis unit has a size of less than 0.5 $mm^2$.

In a further preferred aspect of the present invention, each of the plurality of through-holes formed in the perforated plate of the biochemical analysis unit has a size of less than 0.1 $mm^2$.

In a further preferred aspect of the present invention, each of the plurality of through-holes formed in the perforated plate of the biochemical analysis unit has a size of less than 0.05 mm$^2$.

In a further preferred aspect of the present invention, each of the plurality of through-holes formed in the perforated plate of the biochemical analysis unit has a size of less than 0.01 mm$^2$.

In the present invention, the density of the through-holes formed in the perforated plate of the biochemical analysis unit can be arbitrarily determined depending upon the material of the perforated plate, the thickness of the perforated plate and the kind of electron beam released from the radioactive labeling substance or the wavelength of fluorescence released from the fluorescent substance and the like.

In a preferred aspect of the present invention, the plurality of through-holes are formed in the perforated plate of the biochemical analysis unit at a density of 10 or more per cm$^2$.

In a further preferred aspect of the present invention, the plurality of through-holes are formed in the perforated plate of the biochemical analysis unit at a density of 50 or more per cm$^2$.

In a further preferred aspect of the present invention, the plurality of through-holes are formed in the perforated plate of the biochemical analysis unit at a density of 100 or more per cm$^2$.

In a further preferred aspect of the present invention, the plurality of through-holes are formed in the perforated plate of the biochemical analysis unit at a density of 500 or more per cm$^2$.

In a further preferred aspect of the present invention, the plurality of through-holes are formed in the perforated plate of the biochemical analysis unit at a density of 1,000 or more per cm$^2$.

In a further preferred aspect of the present invention, the plurality of through-holes are formed in the perforated plate of the biochemical analysis unit at a density of 5,000 or more per cm$^2$.

In a further preferred aspect of the present invention, the plurality of through-holes are formed in the perforated plate of the biochemical analysis unit at a density of 10,000 or more per cm$^2$.

In the present invention, a porous material or a fiber material may be preferably used as the absorptive material for forming the absorptive region. The absorptive region may be formed by combining a porous material and a fiber material.

In the present invention, a porous material for forming the absorptive region may be any type of an organic material or an inorganic material and may be an organic/inorganic composite material.

In the present invention, an organic porous material used for forming the absorptive region is not particularly limited but a carbon porous material such as an activated carbon or a porous material capable of forming a membrane filter is preferably used. Illustrative examples of porous materials capable of forming a membrane filter include nylons such as nylon-6, nylon-6,6, nylon-4, 10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof.

In the present invention, an inorganic porous material used for forming the absorptive region is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof.

In the present invention, a fiber material used for forming the absorptive region is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

In the present invention, the absorptive region may be formed using an oxidization process such as an electrolytic process, a plasma process an arc discharge process and the like; a primer process using a silane coupling agent, titanium coupling agent and the like; and a surface-active agent process and the like.

In the present invention, in the case where a plurality of dot-like stimulable phosphor layer regions are formed in the support of the stimulable phosphor sheet, the plurality of dot-like stimulable phosphor layer regions may be formed on the surface of the support or the plurality of dot-like stimulable phosphor layer regions may be formed in a plurality of holes formed dot-like in the support.

In the present invention, in the case where a plurality of dot-like stimulable phosphor layer regions are formed in the support of the stimulable phosphor sheet, the plurality of dot-like stimulable phosphor layer regions are formed in the same pattern as that of the absorptive regions formed in the biochemical analysis unit.

In a preferred aspect of the present invention, a plurality of through-holes are formed dot-like in the support of the stimulable phosphor sheet and stimulable phosphor layer regions are formed in the plurality of through-holes.

In a further preferred aspect of the present invention, stimulable phosphor layer regions are formed by charging stimulable phosphor in the plurality of through-holes.

In another preferred aspect of the present invention, a plurality of recesses are dot-like formed in the support of the stimulable phosphor sheet and stimulable phosphor layer regions are formed in the plurality of recesses.

In a further preferred aspect of the present invention, stimulable phosphor layer regions are formed by charging stimulable phosphor in the plurality of recesses.

In a preferred aspect of the present invention, a plurality of dot-like stimulable phosphor layer regions are regularly formed in the stimulable phosphor sheet.

In the present invention, in the case where a plurality of dot-like stimulable phosphor layer regions are formed in the support of the stimulable phosphor sheet, the material for forming the support of the stimulable phosphor sheet preferably has a property of attenuating radiation energy. The material capable of attenuating radiation energy and usable for forming the support of the stimulable phosphor sheet is not particularly limited but may be of any type of inorganic compound material or organic compound material insofar as it can attenuate radiation energy. It is preferably formed of metal material, ceramic material or plastic material.

In the present invention, illustrative examples of inorganic compound materials capable of attenuating radiation energy and preferably usable for forming the support of the stimulable phosphor sheet in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound is preferably used as an organic compound material capable of attenuating radiation energy. Illustrative examples of high molecular compounds and preferably usable for forming a support of the stimulable phosphor sheet in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, the support of the stimulable phosphor sheet is preferably formed of a compound material or a composite material having specific gravity of 1.0 g/cm$^3$ or more and more preferably formed of a compound material or a composite material having specific gravity of 1.5 g/cm$^3$ to 23 g/cm$^3$.

In a preferred aspect of the present invention, a material capable of attenuating radiation energy has property of reducing the energy of radiation to $1/5$ or less when the radiation travels in the material by the distance between neighboring dot-like stimulable phosphor layer regions.

In a further preferred aspect of the present invention, the support of the stimulable phosphor sheet is made of a material capable of reducing the energy of radiation to $1/10$ or less when the radiation travels in the material by the distance between neighboring dot-like stimulable phosphor layer regions.

In a further preferred aspect of the present invention, the support of the stimulable phosphor sheet is made of a material capable of reducing the energy of radiation to $1/50$ or less when the radiation travels in the material by the distance between neighboring dot-like stimulable phosphor layer regions.

In a further preferred aspect of the present invention, the support of the stimulable phosphor sheet is made of a material capable of reducing the energy of radiation to $1/100$ or less when the radiation travels in the material by the distance between neighboring dot-like stimulable phosphor layer regions.

In a further preferred aspect of the present invention, the support of the stimulable phosphor sheet is made of a material capable of reducing the energy of radiation to $1/500$ or less when the radiation travels in the material by the distance between neighboring dot-like stimulable phosphor layer regions.

In a further preferred aspect of the present invention, the support of the stimulable phosphor sheet is made of a material capable of reducing the energy of radiation to $1/1000$ or less when the radiation travels in the material by the distance between neighboring dot-like stimulable phosphor layer regions.

The above and other objects of the present invention can also be accomplished by a biochemical analyzing method comprising the steps of preparing a stimulable phosphor sheet including a support, selectively storing radiation energy in a plurality of stimulable phosphor layer regions formed at least one-dimensionally and spaced-apart from each other in the support, moving the stimulable phosphor sheet and a stimulating ray relative to each other in at least a main scanning direction, sequentially irradiating the plurality of stimulable phosphor layer regions with the stimulating ray, thereby exciting stimulable phosphor contained in the plurality of stimulable phosphor layer regions, photoelectrically detecting stimulated emission released from the stimulable phosphor, thereby producing analog data, converting the analog data to digital data and producing biochemical analysis data.

According to this aspect of the present invention, since biochemical analysis data are produced by selectively storing radiation energy in a plurality of stimulable phosphor layer regions formed at least one-dimensionally and spaced-apart from each other in the support, moving the stimulable phosphor sheet and a stimulating ray relative to each other in at least a main scanning direction, sequentially irradiating the plurality of stimulable phosphor layer regions with the stimulating ray, thereby exciting stimulable phosphor contained in the plurality of stimulable phosphor layer regions, photoelectrically detecting stimulated emission released from the stimulable phosphor, thereby producing analog data, and converting the analog data to digital data, it is possible to produce biochemical analysis data with high resolving power and high quantitative accuracy.

In a preferred aspect of the present invention, the plurality of stumulable phosphor layer regions are formed two-dimensionally and spaced-apart from each other in the support and biochemical analysis data are produced by moving the stimulable phosphor sheet and the stimulating ray relative to each other in the main scanning direction and a sub-scanning direction perpendicular to the main scanning direction, sequentially irradiating the plurality of stimulable phosphor layer regions with the stimulating ray, thereby exciting stimulable phosphor contained in the plurality of stimulable phosphor layer regions, photoelectrically detecting stimulated emission released from the stimulable phosphor, thereby producing analog data, and converting the analog data to digital data.

According to this preferred aspect of the present invention, since the stimulable phosphor layer regions can be formed at a high density, biochemical analysis data can be efficiently produced.

In a preferred aspect of the present invention, a laser beam is used as a stimulating ray and stimulable phosphor contained in the plurality of stimulable phosphor layer regions is excited by moving the stimulable phosphor sheet and the laser beam relative to each other in the main scanning direction and a sub-scanning direction perpendicular to the main scanning direction, and sequentially irradiating the plurality of stimulable phosphor layer regions with the laser beam.

In a preferred aspect of the present invention, the stimulable phosphor sheet is moved in the main scanning direction.

In another preferred aspect of the present invention, the stimulating ray is moved in the main scanning direction.

In the present invention, the stimulable phosphor usable in the present invention may be of any type insofar as it can store radiation energy or electron beam energy and can be stimulated by an electromagnetic wave to release the radiation energy or the electron beam energy stored therein in the form of light. More specifically, preferably employed stimulable phosphors include alkaline earth metal fluorohalide phosphors $(Ba_{1-x}, M^{2+}_x)FX:yA$ (where $M^{2+}$ is at least one alkaline earth metal selected from the group consisting of Mg, Ca, Sr, Zn and Cd; X is at least one element selected from the group consisting of Cl, Br and I, A is at least one element selected from the group consisting of Eu, Tb, Ce, Tm, Dy, Pr, Ho, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; Z is at least one Eu and Ce) disclosed in Japanese Patent Application Laid Open No. 2-276997, europium activated complex halide phosphors $BaFXxNaX':aEu^{2+}$ (where each of X or X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br and I; and x is greater than 0 and equal to or less than 0.1) disclosed in U.S. Pat. No. 4,539,137, and europium activated complex halide phosphors $M^{II}FxaM^{I}X'bM^{II}X''_2 cM^{III}X'''_3 xA:yEu^{2+}$ (where $M^{II}$ is at least one alkaline earth metal selected from the group consisting of Ba, Sr and Ca; $M^{I}$ is at least one alkaline metal selected from the group consisting of Li, Na, K, Rb and Cs; $M^{II}$ is at least one divalent metal selected from the group consisting of Be and Mg; $M^{III}$ is at least one trivalent metal selected from the group consisting of Al, Ga, In and Ti; A is at least one metal oxide; X is at least one halogen selected from the group consisting of Cl, Br and I; each of X', X" and X''' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

In a preferred aspect of the present invention, specific binding substances may be spotted onto the absorptive regions of a biochemical analysis unit using a spotting device.

In a preferred aspect of the present invention, a spotting device includes a base plate onto which a biochemical analysis unit, on which specific binding substances are to be spotted, is to be placed, a spotting head capable of spotting specific binding substances, and sensor means for detecting a reference position of the absorptive region to which specific binding substances are to be spotted.

In a preferred aspect of the present invention, a spotting device further includes a drive mechanism for at least one-dimensionally and intermittently moving the spotting head and the base plate relative to each other.

According to this preferred aspect of the present invention, since a spotting device further includes a drive mechanism for at least one-dimensionally and intermittently moving the spotting head and the base plate relative to each other, specific binding substances can be reliably spotted onto the absorptive regions formed in a biochemical analysis unit in at least one-dimension by using the sensor means to detect the absorptive regions of the biochemical analysis unit placed on the base plate for spotting with specific binding substances, thereby determining the relative positional relationship between the spotting head of the spotting device and the base plate on which the biochemical analysis unit is placed, and spotting specific binding substances from the spotting head, while operating the driving mechanism for at least one dimensionally and intermittently moving the spotting head and the base plate relative to each other.

In a further preferred aspect of the present invention, the drive mechanism is adapted for at least one-dimensionally moving the spotting head and the base plate relative to each other at a constant pitch.

According to this preferred aspect of the present invention, since the drive mechanism is adapted for at least one-dimensionally moving the spotting head and the base plate relative to each other at a constant pitch, specific binding substances can be reliably spotted onto the absorptive regions formed in a biochemical analysis unit in at least one-dimension by using the sensor means to detect the absorptive regions of the biochemical analysis unit placed on the base plate for spotting with specific binding substances, thereby determining the relative positional relationship between the spotting head of the spotting device and the base plate on which the biochemical analysis unit is placed, and spotting specific binding substances from the spotting head, while operating the driving mechanism for at least one dimensionally moving the spotting head and the base plate relative to each other at a constant pitch.

In a further preferred aspect of the present invention, the drive mechanism is adapted for relatively and intermittently moving the spotting head and the base in two dimensions.

According to this preferred aspect of the present invention, since the drive mechanism is adapted for relatively and intermittently moving the spotting head and the base in two dimensions, specific binding substances can be reliably spotted onto the absorptive regions two-dimensionally formed in a biochemical analysis unit by using the sensor means to detect the absorptive regions of the biochemical analysis unit placed on the base plate for spotting with specific binding substances, thereby determining the relative positional relationship between the spotting head of the spotting device and the base plate on which the biochemical analysis unit is placed, and spotting specific binding substances from the spotting head, while operating the driving mechanism for relatively and intermittently moving the spotting head and the base plate in two dimensions.

In a further preferred aspect of the present invention, the drive mechanism is adapted for relatively and intermittently moving the spotting head and the base at a constant pitch in two dimensions.

According to this preferred aspect of the present invention, since the drive mechanism is adapted for relatively and intermittently moving the spotting head and the base at a constant pitch in two dimensions, specific binding substances can be reliably spotted onto the absorptive regions two-dimensionally formed in a biochemical analysis unit by using the sensor means to detect the absorptive regions of the biochemical analysis unit placed on the base plate for spotting with specific binding substances, thereby determining the relative positional relationship between the spotting head of the spotting device and the base plate on which the biochemical analysis unit is placed, and spotting specific binding substances from the spotting head, while operating the driving mechanism for relatively and intermittently moving the spotting head and the base plate at a constant pitch in two dimensions.

In a preferred aspect of the present invention, at least two positioning members are formed in the base plate for positioning a biochemical analysis unit.

According to this preferred aspect of the present invention, since at least two positioning members are formed in the base plate for positioning a biochemical analysis unit, it is possible to position the biochemical analysis unit onto which specific binding substances are to be spotted at a predetermined position of the base plate and set it on the base plate.

In a further preferred aspect of the present invention, each of the positioning members is constituted as a pin uprightly formed on the base plate.

According to this preferred aspect of the present invention, since each of the positioning members is constituted as a pin uprightly formed on the base plate, it is possible to easily position the biochemical analysis unit onto which specific binding substances are to be spotted at a predetermined position of the base plate and set it on the base plate by forming the biochemical analysis unit with positioning through-holes corresponding to the pins.

In a preferred aspect of the present invention, the spotting device further includes positional data calculating means for calculating positional data of the absorptive regions of the biochemical analysis unit onto which specific binding substances are to be spotted based on at least two reference positions of the biochemical analysis unit detected by the sensor means, a memory for storing the positional data of the absorptive regions of the biochemical analysis unit onto which specific binding substances are to be spotted calculated by the positional data calculating means, and position control means for controlling the drive mechanism in accordance with the positional data of the absorptive regions of the biochemical analysis unit onto which specific binding substances are to be spotted stored in the memory.

According to this preferred aspect of the present invention, since the spotting device further includes positional data calculating means for calculating positional data of the absorptive regions of the biochemical analysis unit onto which specific binding substances are to be spotted based on at least two references positions of the biochemical analysis unit detected by the sensor means, a memory for storing the positional data of the absorptive regions of the biochemical analysis unit onto which specific binding substances are to be spotted calculated by the positional data calculating means, and position control means for controlling the drive mechanism in accordance with the positional data of the absorptive regions of the biochemical analysis unit onto which specific binding substances are to be spotted stored in the memory, it is possible to automatically spot specific binding substances onto a plurality of absorptive regions spaced-apart and dot-like formed in the substrate.

The above and other objects and features of the present invention will become apparent from the following description made with reference to the accompanying drawings.

DESCRIPTION OF THE PREFERRED EMBODIMENT

Figure 1:
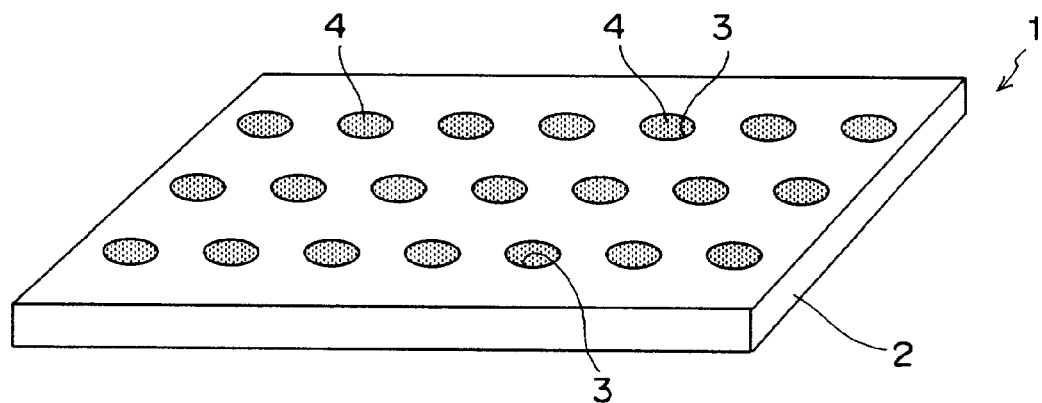
FIG. 1 is a schematic perspective view showing a biochemical analysis unit which is a preferred embodiment of the present invention.

FIG. 1 is a schematic perspective view showing a biochemical analysis unit which is a preferred embodiment of the present invention.

As shown in FIG. 1, a biochemical analysis unit 1 includes a substrate 2 formed of metal such as aluminum capable of attenuating radiation energy and light energy and having flexibility and formed with a number of substantially circular through-holes 3, and absorptive material 4 such as nylon-6 is charged in the through-holes 3.

Although not accurately shown in FIG. 1, in this embodiment, about 10,000 through-holes 3 having a size of about 0.01 cm$^2$ are regularly formed at a density of about 10,000 per cm$^2$ in the substrate 2.

Figure 2:
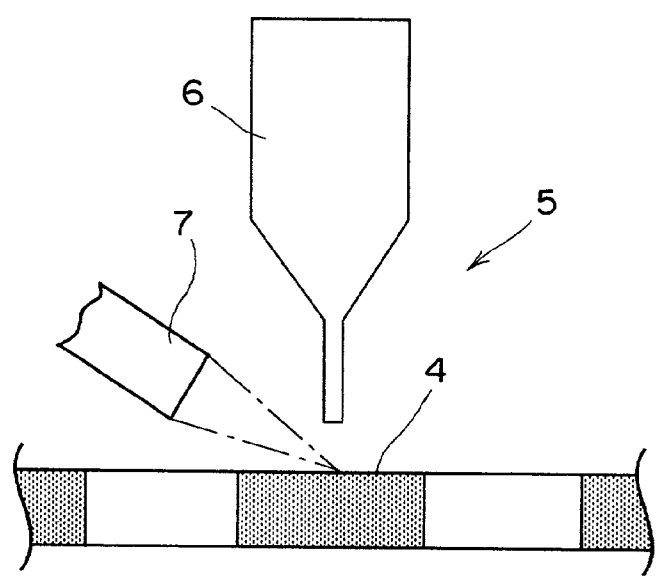
FIG. 2 is a schematic front view showing a spotting device.

FIG. 2 is a schematic front view showing a spotting device.

When biochemical analysis is performed, as shown in FIG. 2, specific binding substances such as a plurality of cDNAs whose sequences are known but are different from each other are spotted using a spotting device onto the porous material 4 charged in a number of the through-holes 3 of the biochemical analysis unit 1.

As shown in FIG. 2, the spotting head 5 of the spotting device includes an injector 6 for ejecting a solution of specific binding substances toward the biochemical analysis unit 1 and a CCD camera 7 and is constituted so that cDNAs are spotted from the injector 6 when the tip end portion of the injector 6 and the center of the through-hole 3 into which a specific binding substance is to be spotted are determined to coincide with each other as a result of viewing them using the CCD camera, thereby ensuring that cDNAs can be accurately spotted into the through-hole 3 in which porous material is charged.

Figure 3:
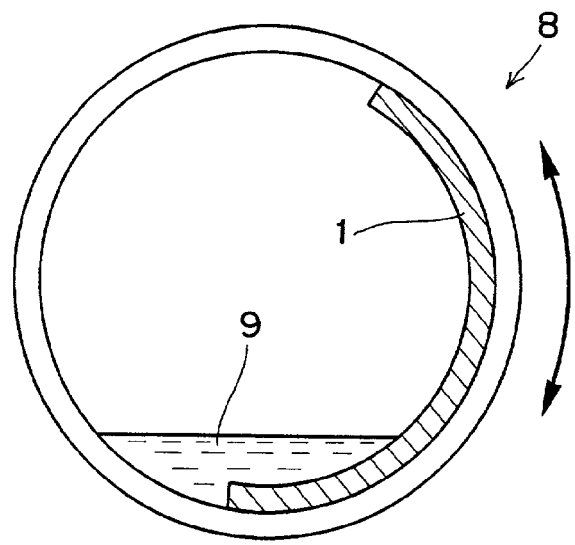
FIG. 3 is a schematic front view showing a hybridization vessel.

FIG. 3 is a schematic front view showing a hybridization vessel.

As shown in FIG. 3, a hybridization vessel 8 is formed cylindrically and accommodates a hybridization solution 9 containing a substance derived from a living organism labeled with a labeling substance therein.

In the case where a specific binding substance such as cDNA is to be labeled with a radioactive labeling substance, a hybridization solution 9 containing a substance derived from a living organism labeled with a radioactive labeling substance is prepared and is accommodated in the hybridization vessel 8.

On the other hand, in the case where a specific binding substance such as cDNA is to be labeled with a labeling substance which generates chemiluminescent emission when it contacts a chemiluminescent substrate, a hybridization solution 9 containing a substance derived from a living organism labeled with a labeling substance which generates chemiluminescent emission when it contacts a chemiluminescent substrate is prepared and is accommodated in the hybridization vessel 8.

Further, in the case where a specific binding substance such as cDNA is to be labeled with a fluorescent substance such as a fluorescent dye, a hybridization solution 9 containing a substance derived from a living organism labeled with a fluorescent substance such as a fluorescent dye is prepared and is accommodated in the hybridization vessel 8.

It is possible to prepare a hybridization solution 9 containing two or more substances derived from a living organism among a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye and accommodate it in the hybridization vessel 8. In this embodiment, a hybridization solution 9 containing a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye is prepared and accommodated in the hybridization vessel 8.

When hybridization is to be performed, the biochemical analysis unit 1 containing specific binding substances such as a plurality of cDNAs spotted into a number of through-holes 3 in which porous material is charged is accommodated in the hybridization vessel 8. In this embodiment, since the substrate 2 is formed of a metal having flexibility, as shown in FIG. 3, the biochemical analysis unit 1 can be bent and accommodated in the hybridization vessel 8 along the inner wall surface thereof.

As shown in FIG. 3, the hybridization vessel 8 is constituted so as to be rotatable about a shaft by a drive means (not shown) and since the biochemical analysis unit 1 is bent and accommodated in the hybridization vessel 8 along the inner wall surface thereof, even when the hybridization vessel 8 accommodates only a small amount of hybridization solution 9, specific binding substances spotted in a number of the through-holes 3 charged with porous material can be selectively hybridized with a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye by rotating the hybridization vessel 8.

As a result of the hybridization, fluorescence data of a fluorescent substance such as a fluorescent dye and chemiluminescence data of a substance derived from a living organism labeled with a labeling substance which generates chemiluminescent emission when it contacts a chemiluminescent substrate are recorded in the porous material 4 charged in a number of the through-holes 3 of the biochemical analysis unit 1. Fluorescence data recorded in the porous material 4 are read by a scanner described later, thereby producing biochemical analysis data and chemiluminescence data recorded in the porous material 4 are read by a data producing system described later, thereby producing biochemical analysis data.

Figure 4:
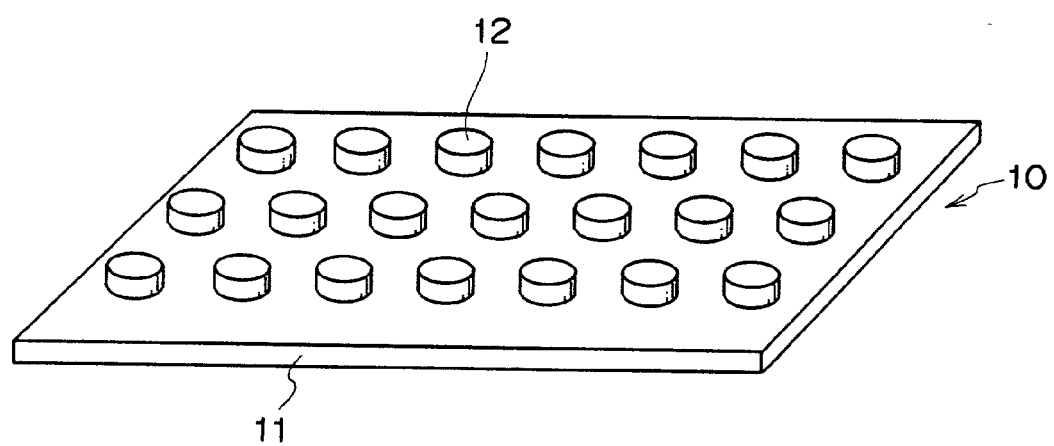
FIG. 4 is a schematic perspective view showing a stimulable phosphor sheet.

FIG. 4 is a schematic perspective view showing a stimulable phosphor sheet.

As shown in FIG. 4, a stimulable phosphor sheet 10 includes a support 11 and one surface of the support 11 is formed with a number of dot-like substantially circular stimulable phosphor layer regions 12 in the same regular pattern as that of a number of through-holes 3 formed in the biochemical analysis unit 1.

In this embodiment, the support 11 is formed of stainless capable of attenuating radiation energy.

Figure 5:
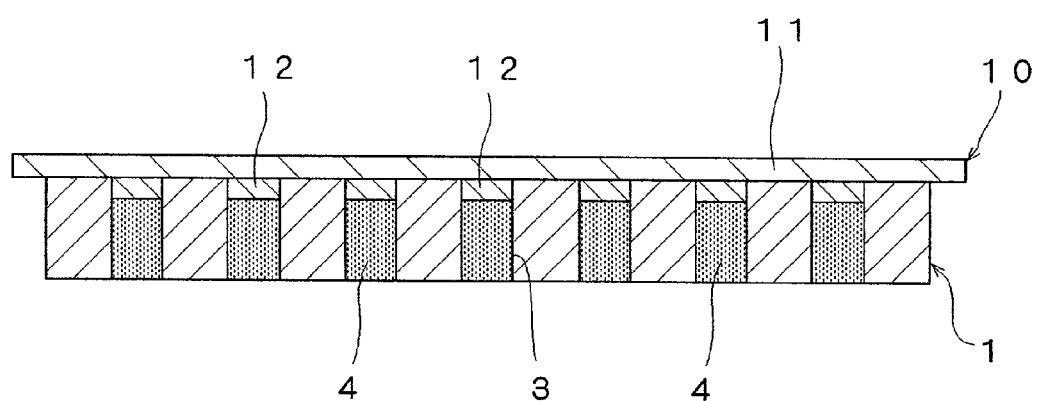
FIG. 5 is a schematic cross-sectional view showing a method for exposing a number of dot-like stimulable phosphor layer regions formed on a stimulable phosphor sheet by a radioactive labeling substance contained in absorptive regions formed in a number of through-holes.

FIG. 5 is a schematic cross-sectional view showing a method for exposing a number of dot-like stimulable phosphor layer regions 12 formed on the stimulable phosphor sheet 10 to a radioactive labeling substance contained in the absorptive regions 4 formed in a number of through-holes 3.

As shown in FIG. 5, when the stimulable phosphor sheet 10 is to be exposed, the stimulable phosphor sheet 10 is superposed on the biochemical analysis unit 1 in such a manner that each of the dot-like stimulable phosphor layer regions 12 formed in the stimulable phosphor sheet 10 is located in one of the many through-holes 3 formed in the biochemical analysis unit 1 and that the surface of each of the dot-like stimulable phosphor layer regions 12 comes into close contact with the surface of the porous material 4 charged in one of the through-holes 3.

In this embodiment, since the substrate 2 of the biochemical analysis unit 1 is formed of a metal, it is hardly stretched and shrunk even when it is subjected to liquid processing such as hybridization and, therefore, it is possible to easily and accurately superpose the stimulable phosphor sheet 10 on the biochemical analysis unit 1 so that each of the dot-like stimulable phosphor layer regions 12 formed in the stimulable phosphor sheet 10 is located in one of the many through-holes 3 formed in the biochemical analysis unit 1 and that the surface of each of the dot-like stimulable phosphor layer regions 12 comes into close contact with the surface of the porous material 4 charged in one of the through-holes 3, thereby exposing the dot-like stimulable phosphor layer regions 12.

In this manner, the surface of each of the dot-like stimulable phosphor layer regions 12 is kept in close contact with the surface of the porous material 4 charged in one of the through-holes 3 for a predetermined time period, whereby a number of the dot-like stimulable phosphor layer regions 12 formed in the stimulable phosphor sheet 10 are exposed to the radioactive labeling substance contained in the porous material 4.

During the exposure operation, electron beams are released from the radioactive labeling substance. However, since the substrate 2 is formed of a metal capable of attenuating radiation energy and light energy, electron beams released from the radioactive labeling substance are prevented from being scattered in the substrate 2. Further, since each of a number of dot-like stimulable phosphor layer regions 12 formed in the stimulable phosphor sheet 10 is located in one of the many through-holes 3 formed in the biochemical analysis unit 1, the electron beams released from the radioactive labeling substance is prevented from being scattered in the dot-like stimulable phosphor layer region 12 and advancing to the dot-like stimulable phosphor layer region 12 located in neighboring through-holes.

Moreover, since the support 11 of the stimulable phosphor sheet 10 is formed of stainless capable of attenuating radiation energy in this embodiment, the electron beams can be also prevented from being scattered in the support 11 of the stimulable phosphor sheet 10 to enter neighboring dot-like stimulable phosphor layers region 12.

Therefore, it is possible to reliably expose a number of the dot-like stimulable phosphor layer regions 12 formed in the stimulable phosphor sheet 10 to only the radioactive labeling substance contained in the porous material 4 charged in the corresponding through-holes 3.

In this manner, radiation data of a radioactive labeling substance are recorded in a number of the dot-like stimulable phosphor layer regions 12 formed in the stimulable phosphor sheet 10.

Figure 6:
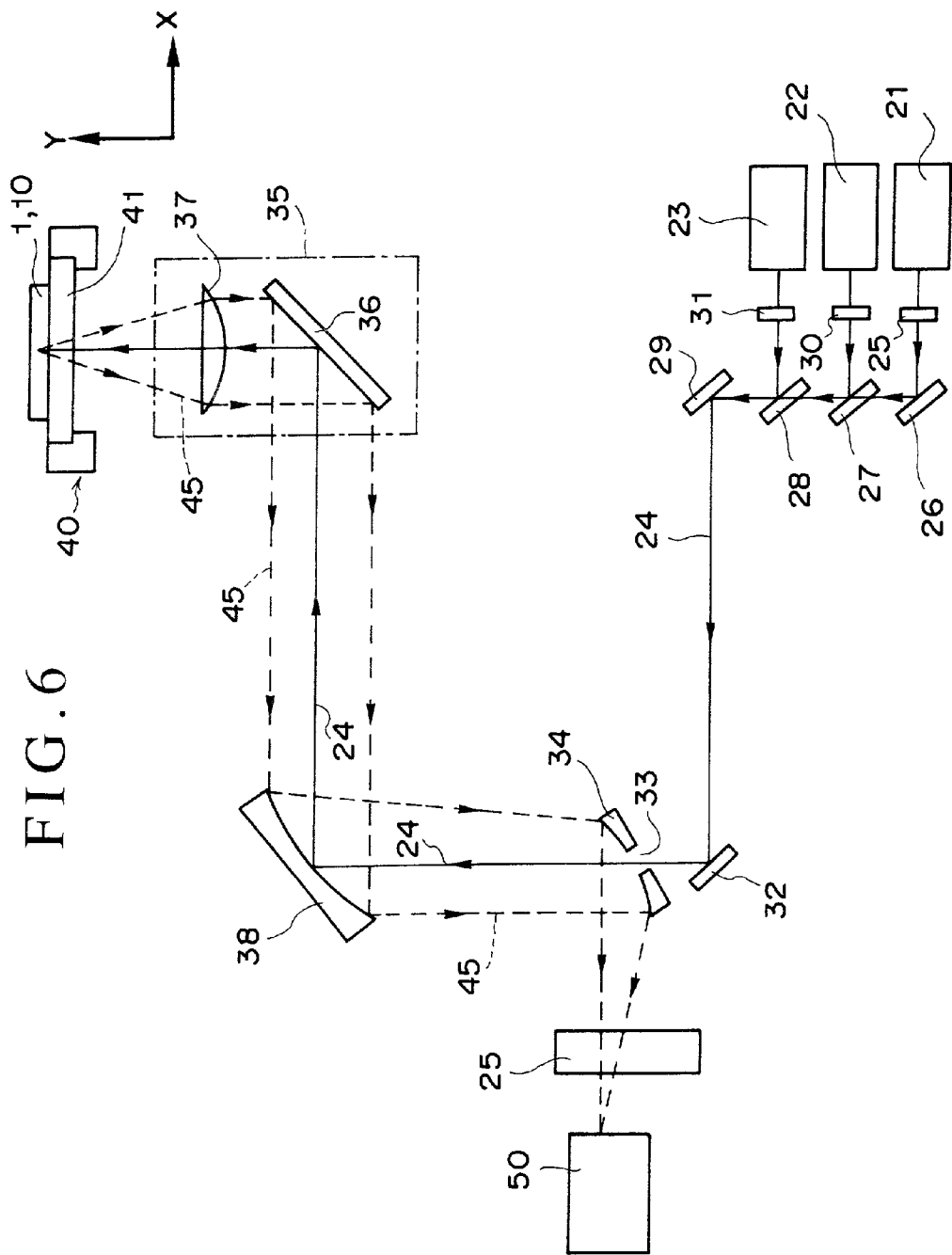
FIG. 6 is a schematic perspective view showing one example of a scanner for reading radiation data of a radioactive labeling substance recorded in a number of stimulable phosphor layer regions formed on a stimulable phosphor sheet and fluorescence data recorded in absorptive regions formed in a number of holes of a biochemical analysis unit and producing biochemical analysis data.
Figure 7:
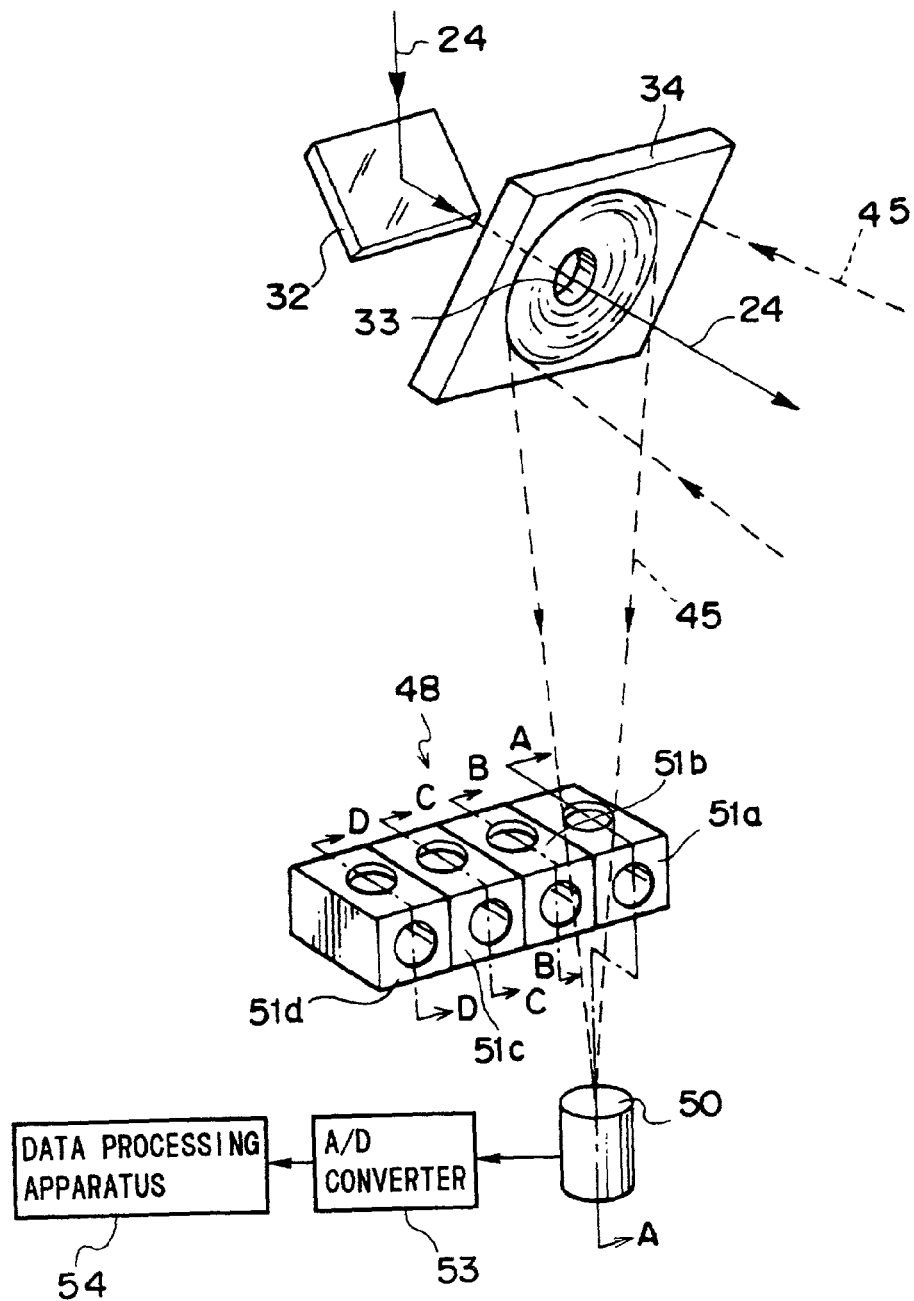
FIG. 7 is a schematic perspective view showing details in the vicinity of a photomultiplier.

FIG. 6 is a schematic perspective view showing one example of a scanner for reading radiation data of a radioactive labeling substance recorded in a number of the dot-like stimulable phosphor layer regions 12 formed on the stimulable phosphor sheet 10 and fluorescence data recorded in the absorptive regions 4 formed in a number of through-holes 3 of the biochemical analysis unit 1 and producing biochemical analysis data, and FIG. 7 is a schematic perspective view showing details in the vicinity of a photomultiplier.

The scanner shown in FIG. 6 is constituted so as to read radiation data of a radioactive labeling substance recorded in a number of the dot-like stimulable phosphor layer regions 12 formed on the stimulable phosphor sheet 10 and fluorescence data recorded in the porous material 4 charged in a number of through-holes 3 formed in the biochemical analysis unit 1 and includes a first laser stimulating ray source 21 for emitting a laser beam having a wavelength of 640 nm, a second laser stimulating ray source 22 for emitting a laser beam having a wavelength of 532 nm and a third laser stimulating ray source 23 for emitting a laser beam having a wavelength of 473 nm. In this embodiment, the first laser stimulating ray source 21 constituted by a semiconductor laser beam source and the second laser stimulating ray source 22 and the third laser stimulating ray source 23 are constituted by a second harmonic generation element.

A laser beam 24 emitted from the first laser stimulating source 21 passes through a collimator lens 25, thereby being made a parallel beam, and is reflected by a mirror 26. A first dichroic mirror 27 for transmitting light having a wavelength of 640 nm but reflecting light having a wavelength of 532 nm and a second dichroic mirror 28 for transmitting light having a wavelength equal to and longer than 532 nm but reflecting light having a wavelength of 473 nm are provided in the optical path of the laser beam 24 emitted from the first laser stimulating ray source 21. The laser beam 24 emitted from the first laser stimulating ray source 21 and reflected by the mirror 26 passes through the first dichroic mirror 27 and the second dichroic mirror 28 and advances to a mirror 29.

On the other hand, the laser beam 24 emitted from the second laser stimulating ray source 22 passes through a collimator lens 30, thereby being made a parallel beam, and is reflected by the first dichroic mirror 27, thereby changing its direction by 90 degrees. The laser beam 24 then passes through the second dichroic mirror 28 and advances to the mirror 29.

Further, the laser beam 24 emitted from the third laser stimulating ray source 23 passes through a collimator lens 31, thereby being made a parallel beam, and is reflected by the second dichroic mirror 28, thereby changing its direction by 90 degrees. The laser beam 24 then advances to the mirror 29.

The laser beam 24 advancing to the mirror 29 is reflected by the mirror 29 and advances to a mirror 32 to be reflected thereby.

A perforated mirror 34 formed with a hole 33 at the center portion thereof is provided in the optical path of the laser beam 24 reflected by the mirror 32. The laser beam 4 reflected by the mirror 32 passes through the hole 33 of the perforated mirror 34 and advances to a concave mirror 38.

The laser beam 24 advancing to the concave mirror 38 is reflected by the concave mirror 38 and enters an optical head 35.

The optical head 35 includes a mirror 36 and an aspherical lens 37. The laser beam 24 entering the optical head 35 is reflected by the mirror 36 and condensed by the aspherical lens 37 onto the stimulable phosphor sheet 10 or the biochemical analysis unit 1 placed on the glass plate 41 of the stage 40. In FIG. 6, the biochemical analysis unit 1 is placed on the glass plate 41 of the stage 40 in such a manner that the side of the porous material 4 into which a specific binding substance is dropped is directed downward.

When the laser beam 24 impinges on the dot-like stimulable phosphor layer region 12 of the stimulable phosphor 10, stimulable phosphor contained in the dot-like stimulable phosphor layer region 12 formed on the stimulable phosphor 10 is excited, thereby releasing stimulated emission 45. On the other hand, when the laser beam 24 impinges on the biochemical analysis unit 1, a fluorescent dye or the like contained in the porous material 4 in a number of the through-holes 3 is excited, thereby releasing fluorescence 45.

The stimulated emission 45 released from the dot-like stimulable phosphor layer region 12 of the stimulable phosphor 10 or the fluorescence 45 released from the porous material 4 in a number of the through-holes 3 of the biochemical analysis unit 1 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 or the fluorescence 45 advancing to the concave mirror 38 is reflected by the concave mirror 38 and advances to the perforated mirror 34.

As shown in FIG. 7, the stimulated emission 45 or the fluorescence 45 advancing to the perforated mirror 34 is reflected downward by the perforated mirror 34 formed as a concave mirror and advances to a filter unit 48, whereby light having a predetermined wavelength is cut. The stimulated emission 45 or the fluorescence 45 then impinges on a photomultiplier 50, thereby being photoelectrically detected.

As shown in FIG. 7, the filter unit 48 is provided with four filter members 51a, 51b, 51c and 51d and is constituted to be laterally movable in FIG. 7 by a motor (not shown).

Figure 8:
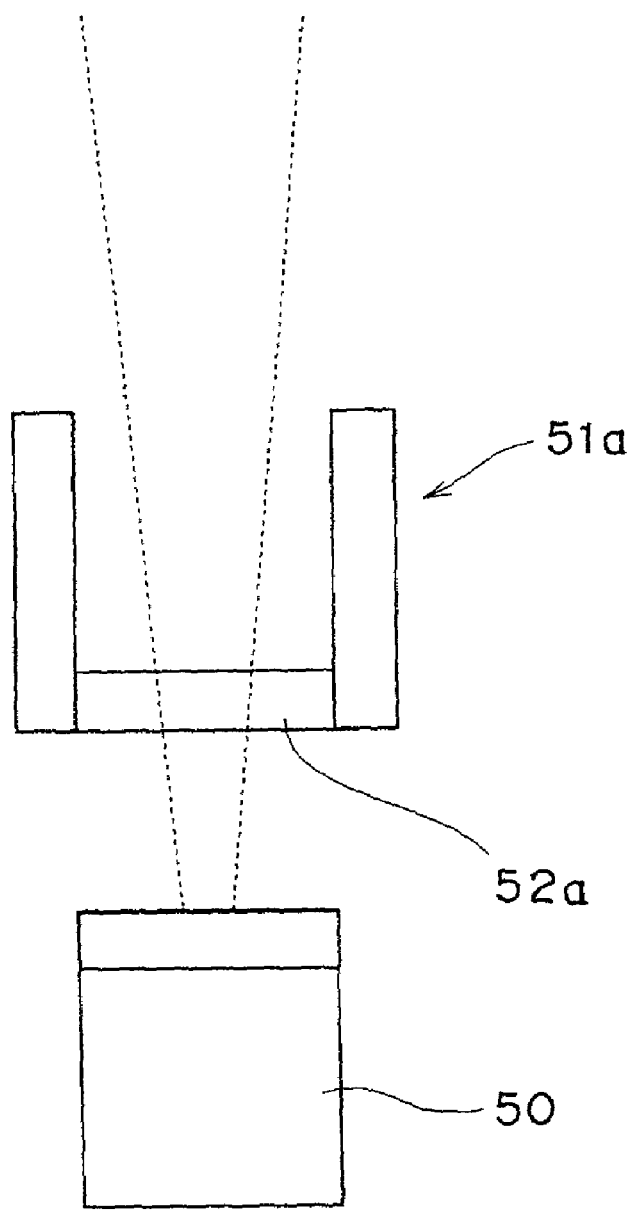
FIG. 8 is a schematic cross-sectional view taken along a line A-A in FIG. 7.

FIG. 8 is a schematic cross-sectional view taken along a line A-A in FIG. 7.

As shown in FIG. 8, the filter member 51a includes a filter 52a and the filter 52a is used for reading fluorescence 45 by stimulating a fluorescent substance such as a fluorescent dye contained in the porous material 4 in a number of through-holes 3 of the biochemical analysis unit 1 using the first laser stimulating ray source 21 and has a property of cutting off light having a wavelength of 640 nm but transmitting light having a wavelength longer than 640 nm.

Figure 9:
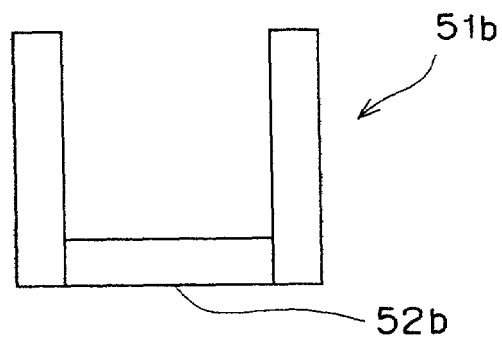
FIG. 9 is a schematic cross-sectional view taken along a line B-B in FIG. 7.

FIG. 9 is a schematic cross-sectional view taken along a line B-B in FIG. 7.

As shown in FIG. 9, the filter member 51b includes a filter 52b and the filter 52b is used for reading fluorescence 45 by stimulating a fluorescent substance such as a fluorescent dye contained in the porous material 4 in a number of through-holes 3 of the biochemical analysis unit 1 using the second laser stimulating ray source 22 and has a property of cutting off light having a wavelength of 532 nm but transmitting light having a wavelength longer than 532 nm.

Figure 10:
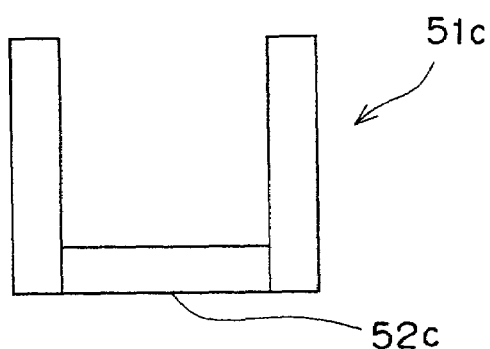
FIG. 10 is a schematic cross-sectional view taken along a line C-C in FIG. 7.

FIG. 10 is a schematic cross-sectional view taken along a line C-C in FIG. 7.

As shown in FIG. 10, the filter member 51a includes a filter 52c and the filter 52c is used for reading fluorescence 45 by stimulating a fluorescent substance such as a fluorescent dye contained in the porous material 4 in a number of through-holes 3 of the biochemical analysis unit 1 using the third laser stimulating ray source 23 and has a property of cutting off light having a wavelength of 473 nm but transmitting light having a wavelength longer than 473 nm.

Figure 11:
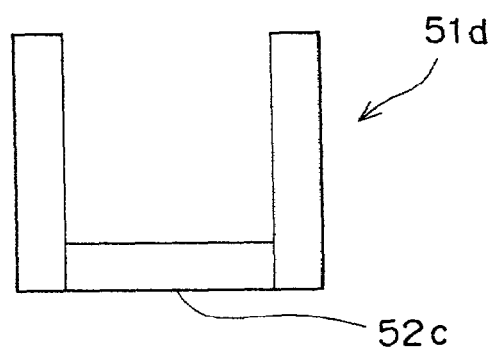
FIG. 11 is a schematic cross-sectional view taken along a line D-D in FIG. 7.

FIG. 11 is a schematic cross-sectional view taken along a line D-D in FIG. 7.

As shown in FIG. 11, the filter member 51d includes a filter 52d and the filter 52d is used for reading stimulated emission released from stimulable phosphor contained in the dot-like stimulable phosphor layer regions 12 formed on the stimulable phosphor sheet 10 upon being stimulated using the first laser stimulating ray source 1 and has a property of transmitting only light having a wavelength corresponding to that of stimulated emission emitted from stimulable phosphor but cutting off light having a wavelength of 640 nm.

Therefore, in accordance with the kind of a stimulating ray source to be used, one of these filter members 51a, 51b, 51c, 51d is selectively positioned in front of the photomultiplier 50, thereby enabling the photomultiplier 50 to photoelectrically detect only light to be detected.

The analog data produced by photoelectrically detecting light with the photomultiplier 50 are converted by an A/D converter 53 into digital data and the digital data are fed to a data processing apparatus 54.

Although not shown in FIG. 6, the optical head 35 is constituted to be movable by a scanning mechanism in the X direction and the Y direction in FIG. 6 so that all of the dot-like stimulable phosphor layer regions 12 formed on the stimulable phosphor sheet 10 or the whole surface of the biochemical analysis unit 1 can be scanned by the laser beam 24.

Figure 12:
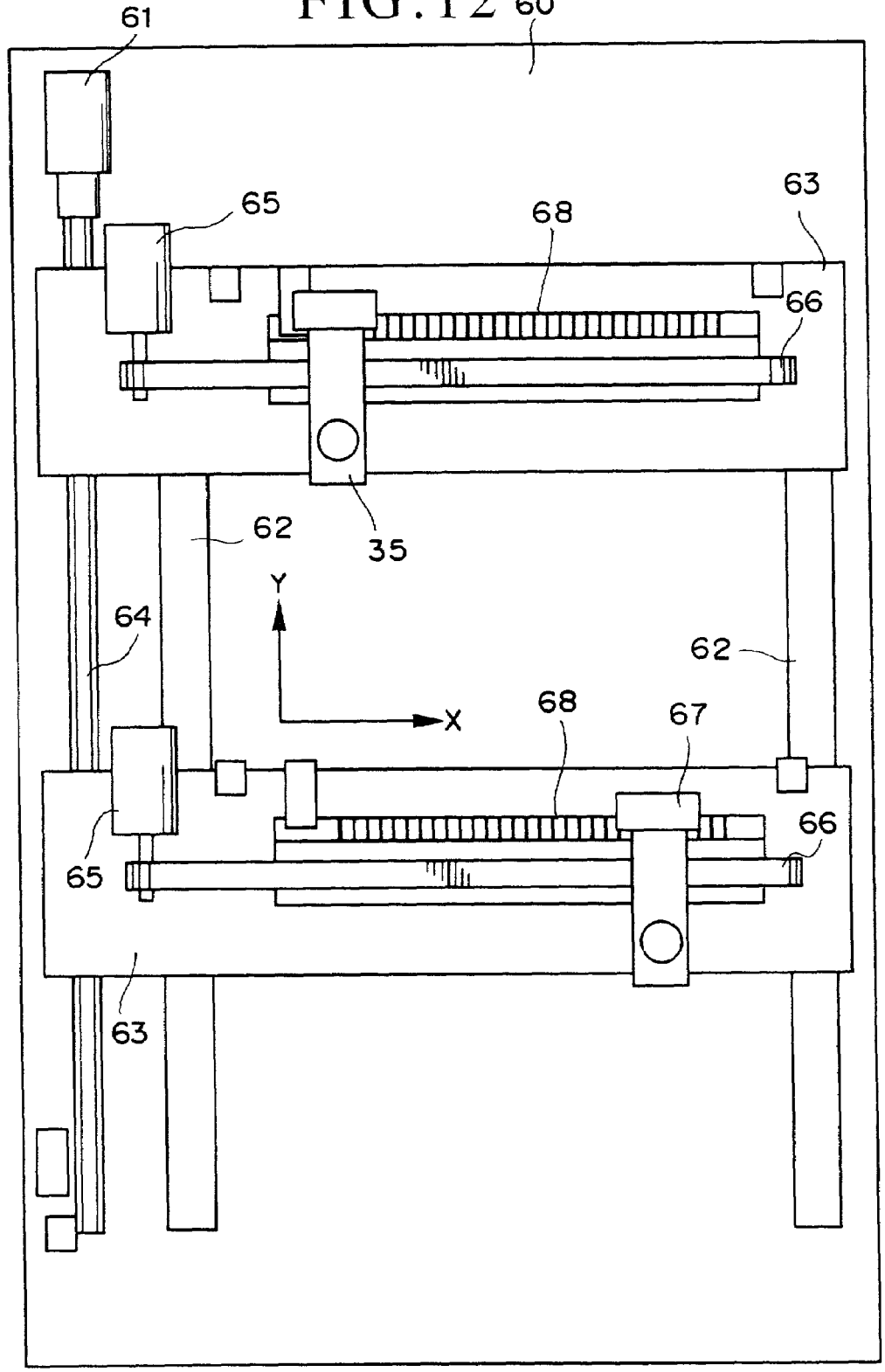
FIG. 12 is a schematic plan view of a scanning mechanism of an optical head.

FIG. 12 is a schematic plan view showing the scanning mechanism of the optical head 35. In FIG. 12, optical systems other than the optical head 35 and the paths of the laser beam 24 and stimulated emission 45 or fluorescence 45 are omitted for simplification.

As shown in FIG. 12, the scanning mechanism of the optical head 35 includes a base plate 60, and a sub-scanning pulse motor 61 and a pair of rails 62, 62 are fixed on the base plate 60. A movable base plate 63 is further provided so as to be movable in the sub-scanning direction indicated by an arrow Y in FIG. 12.

The movable base plate 63 is formed with a threaded hole (not shown) and a threaded rod 64 rotated by the sub-scanning pulse motor 61 is engaged with the inside of the hole.

A main scanning pulse motor 65 is provided on the movable base plate 63. The main scanning pulse motor 65 is adapted for driving an endless belt 66. The optical head 35 is fixed to the endless belt 66 and when the endless belt 66 is driven by the main scanning pulse motor 65, the optical head 35 is moved in the main scanning direction indicated by an arrow X in FIG. 12. In FIG. 12, the reference numeral 67 designates a linear encoder for detecting the position of the optical head 35 in the main scanning direction and the reference numeral 68 designates slits of the linear encoder 67.

Therefore, the optical head 35 is moved in the X direction and the Y direction in FIG. 12 by driving the endless belt 66 in the main scanning direction by the main scanning pulse motor 65 and moving the movable base plate 63 in the sub-scanning direction by the sub-scanning pulse motor 61, thereby scanning all of the dot-like stimulable phosphor layer regions 12 formed on the stimulable phosphor sheet 10 or the whole surface of the biochemical analysis unit 1 with the laser beam 24.

Figure 13:
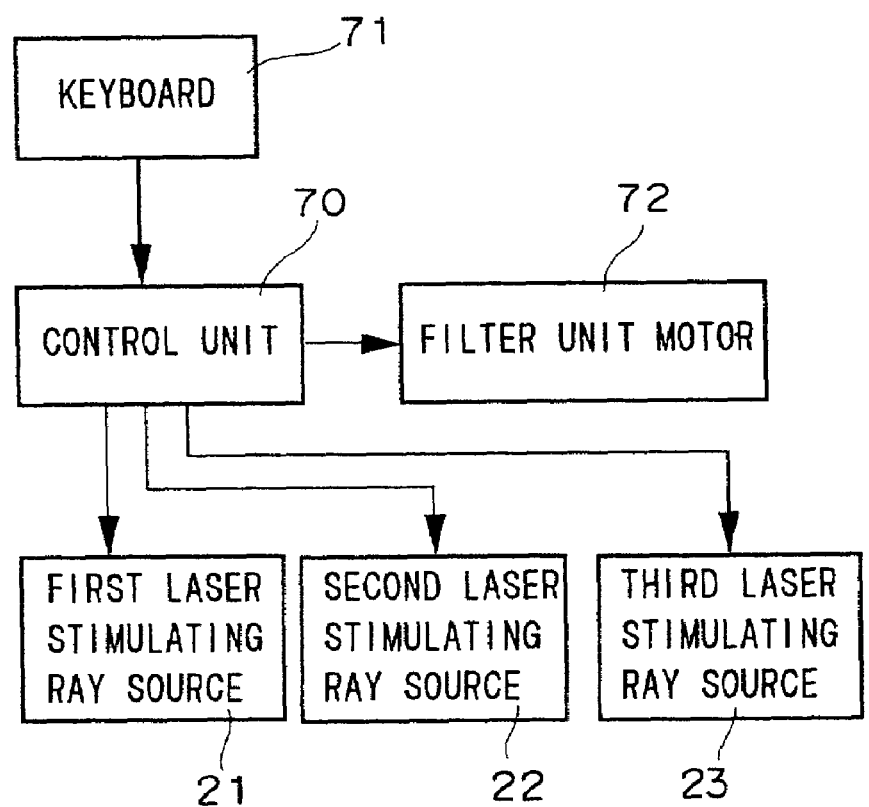
FIG. 13 is a block diagram of a control system, an input system and a drive system of a scanner shown in FIG. 6.

FIG. 13 is a block diagram of a control system, an input system and a drive system of the scanner shown in FIG. 6.

As shown in FIG. 13, the control system of the scanner includes a control unit 70 for controlling the whole operation of the scanner and the input system of the scanner includes a keyboard 71 which can be operated by an operator and through which various instruction signals can be input.

As shown in FIG. 13, the drive system of the scanner includes a filter unit motor 72 for moving the filter unit 48 provided with the four filter members 51a, 51b, 51c and 51d.

The control unit 70 is adapted for selectively outputting a drive signal to the first laser stimulating ray source 21, the second laser stimulating ray source 22 or the third laser stimulating ray source 23 and outputting a drive signal to the filter unit motor 72.

The thus constituted scanner reads fluorescence data of a fluorescent substance such as a fluorescent dye carried in the porous material 4 charged in a number of through-holes 3 formed in the biochemical analysis unit 1 and produces biochemical analysis data in the following manner.

A biochemical analysis unit 1 is first set on the glass plate 41 of the stage 40 by an operator.

The kind of fluorescent substance as a labeling substance is then input through the keyboard 71 by the operator and an instruction signal indicating that fluorescence data are to be read is input through the keyboard 71.

The instruction signal is input to the control unit 70 and when the control unit 70 receives it, it determines the laser stimulating ray source to be used in accordance with a table stored in a memory (not shown) and also determines what filter is to be positioned in the optical path of fluorescence 45 among the filters 52a, 52b and 52c.

For example, when Rhodamine (registered trademark), which can be most efficiently stimulated by a laser beam having a wavelength of 532 nm, is used as a fluorescent substance for labeling a substance derived from a living organism and a signal indicating such a fact is input, the control unit 70 selects the second laser stimulating ray source 22 and the filter 52b and outputs a drive signal to the filter unit motor 72, thereby moving the filter unit 48 so that the filter member 51b inserting the filter 52b having a property of cutting off light having a wavelength of 532 nm but transmitting light having a wavelength longer than 532 nm in the optical path of the fluorescence 45.

The control unit 70 then outputs a drive signal to the second laser stimulating ray source 22 to activate it, thereby causing it to emit a laser beam 24 having a wavelength of 532 nm.

The laser beam 24 emitted from the second laser stimulating ray source 22 is made a parallel beam by the collimator lens 30, advances to the first dichroic mirror 27 and is reflected thereby.

The laser beam 24 reflected by the first dichroic mirror 27 transmits through the second dichroic mirror 28 and enters the mirror 29.

The laser beam 24 entering the mirror 29 is reflected by the mirror 29 and further enters a mirror 32 to be reflected thereby.

The laser beam 24 reflected by the mirror 32 advances to the perforated mirror 34 and passes through the hole 33 of the perforated mirror 34. Then, the laser beam 24 advances to the concave mirror 38.

The laser beam 24 advancing to the concave mirror 38 is reflected thereby and enters the optical head 35.

The laser beam 24 entering the optical head 35 is reflected by the mirror 36 and condensed by the aspherical lens 37 onto the biochemical analysis unit 1 placed on the glass plate 41 of the stage 40.

As a result, a fluorescent substance such as a fluorescent dye, for instance, Rhodamine, contained in the porous material 4 charged in a number of through-holes 3 formed in the biochemical analysis unit 1 is stimulated by the laser beam 24 and fluorescence 45 is released from Rhodamine.

In the biochemical analysis unit 1 according to this embodiment, since the substrate 2 of the biochemical analysis unit 1 is formed of a metal having a property capable of attenuating radiation energy and light energy, it is possible to reliably prevent fluorescence released from a fluorescent substance contained in porous material 4 charged in a through-hole 3 from being scattered in the substrate 2 and mixed with fluorescent released from a fluorescent substance contained in porous material 4 charged in through-holes 3 neighboring the through-hole 3.

The fluorescence 45 released from Rhodamine is condensed by the aspherical lens 37 provided in the optical head 35 and reflected by the mirror 36 on the side of an optical path of the laser beam 24, thereby being made a parallel beam to advance to the concave mirror 38.

The fluorescence 45 advancing to the concave mirror 38 is reflected by the concave mirror 38 and advances to the perforated mirror 34.

As shown in FIG. 7, the fluorescence 45 advancing to the perforated mirror 34 is reflected downward by the perforated mirror 34 formed as a concave mirror and advances to the filter 52b of a filter unit 48.

Since the filter 52b has a property of cutting off light having a wavelength of 532 nm but transmitting light having a wavelength longer than 532 nm, light having the same wavelength of 532 nm as that of the stimulating ray is cut off by the filter 52b and only light in the wavelength of the fluorescence 45 released from Rhodamine passes through the filter 52b to be photoelectrically detected by the photomultiplier 50.

As described above, since the optical head 35 is moved on the base plate 63 in the X direction in FIG. 12 by the main scanning pulse motor 65 mounted on the base plate 63 and the base plate 63 is moved in the Y direction in FIG. 12 by the sub-scanning pulse motor 61, the whole surface of the biochemical analysis unit 1 is scanned by the laser beam 24. Therefore, the photomultiplier 50 can read fluorescent data of Rhodamine recorded in the biochemical analysis unit 1 by photoelectrically detecting the fluorescence 45 released from Rhodamine contained in the porous material in a number of through-holes 3 and produce analog data for biochemical analysis.

The analog data produced by photoelectrically detecting the stimulated emission 45 with the photomultiplier 50 are converted by the A/D converter 53 into digital data and the digital data are fed to the data processing apparatus 54.

On the other hand, when radiation data recorded in a stimulable phosphor sheet 10 by exposing the dot-like stimulable phosphor layer regions 12 to a radioactive labeling substance contained in the porous material in a number of through-holes 3 formed in the biochemical analysis unit 1 are to be read to produce biochemical analysis data, the stimulable phosphor sheet 10 is placed on the glass plate 41 of the stage 40 in such a manner that the dot-like stimulable phosphor layer regions 12 come into contact with the glass plate 41.

An instruction signal indicating that radiation data recorded in the dot-like stimulable phosphor layer regions 12 formed on the stimulable phosphor sheet 10 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51d provided with the filter 52d having a property of transmitting only light having a wavelength corresponding to that of stimulated emission emitted from stimulable phosphor but cutting off light having a wavelength of 640 nm in the optical path of stimulated emission 45.

The control unit 70 then outputs a drive signal to the first laser stimulating ray source 21 to activate it, thereby causing it to emit a laser beam 24 having a wavelength of 640 nm.

The laser beam 24 emitted from the first laser stimulating ray source 21 is made a parallel beam by the collimator lens 25 and advances to the mirror 26 to be reflected thereby.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and further advances to a mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected thereby and enters the optical head 35.

The laser beam 24 entering the optical head 35 is reflected by the mirror 36 and condensed by the aspherical lens 37 onto the dot-like stimulable phosphor layer region 12 of the stimulable phosphor sheet 10 placed on the glass plate 41 of the stage 40.

As a result, a stimulable phosphor contained in the dot-like stimulable phosphor layer region 12 formed on the stimulable phosphor sheet 10 is stimulated by the laser beam 24 and stimulated emission 45 is released from the stimulable phosphor.

The stimulated emission 45 released from the stimulable phosphor contained in the dot-like stimulable phosphor layer region 12 is condensed by the aspherical lens 37 provided in the optical head 35 and reflected by the mirror 36 on the side of an optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of a filter unit 48.

Since the filter 52d has a property of transmitting only light having a wavelength corresponding to that of stimulated emission emitted from stimulable phosphor but cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

As described above, since the optical head 35 is moved on the base plate 63 in the X direction in FIG. 12 by the main scanning pulse motor 65 mounted on the base plate 63 and the base plate 63 is moved in the Y direction in FIG. 12 by the sub-scanning pulse motor 61, all of the dot-like stimulable phosphor layer regions 12 formed on the stimulable phosphor sheet 10 are scanned by the laser beam 24. Therefore, the photomultiplier 50 can read radiation data of a radioactive labeling substance recorded in a number of the dot-like stimulable phosphor layer regions 12 by photoelectrically detecting the stimulated emission 45 released from stimulable phosphor contained in the stimulable phosphor layer regions 12 and produce analog data.

The analog data produced by photoelectrically detecting the stimulated emission 45 with the photomultiplier 50 are converted by the A/D converter 53 into digital data and the digital data are fed to the data processing apparatus 54.

Figure 14:
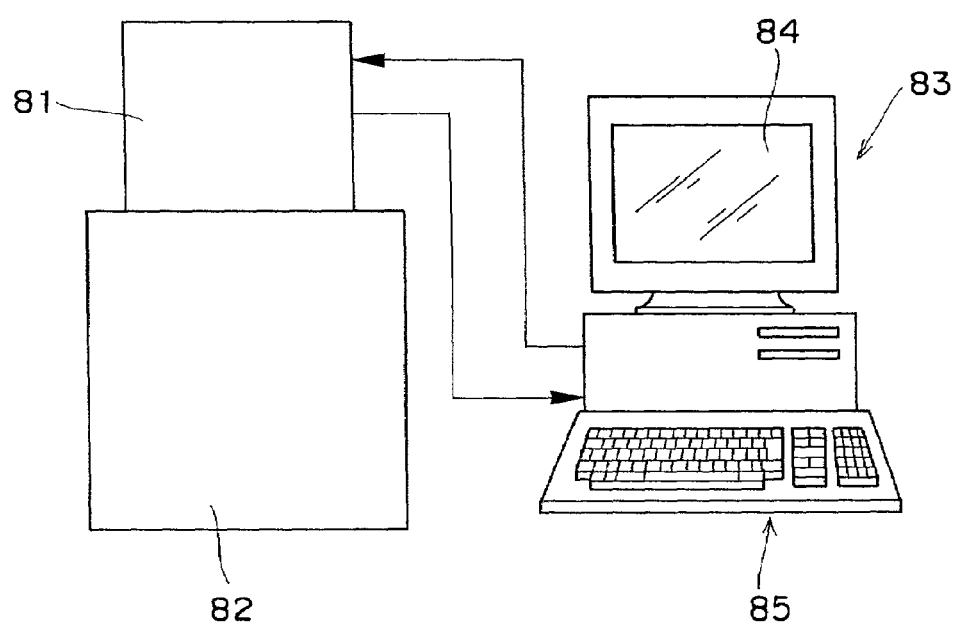
FIG. 14 is a schematic front view showing a data producing system for reading chemiluminescent data of a labeling substance, recorded in absorptive regions formed in a number of through-holes of a biochemical analysis unit, which generates chemiluminescent emission when it contacts a chemiluminescent substrate and producing biochemical analysis data.

FIG. 14 is a schematic front view showing a data producing system for reading chemiluminescent data of a labeling substance recorded in absorptive regions formed in a number of through-holes 3 formed in the biochemical analysis unit 1, which generates chemiluminescent emission when it contacts a chemiluminescent substrate and producing biochemical analysis data. The data producing system shown in FIG. 14 is constituted to be able to also read fluorescence data of a fluorescent substance such as a fluorescent dye recorded in a porous material 4 charged in a number of through-holes 3 formed in the biochemical analysis unit 1.

As shown in FIG. 14, the data producing system includes a cooled CCD camera 81, a dark box 82 and a personal computer 83. As shown in FIG. 14, the personal computer 83 is equipped with a CRT 84 and a keyboard 85.

Figure 15:
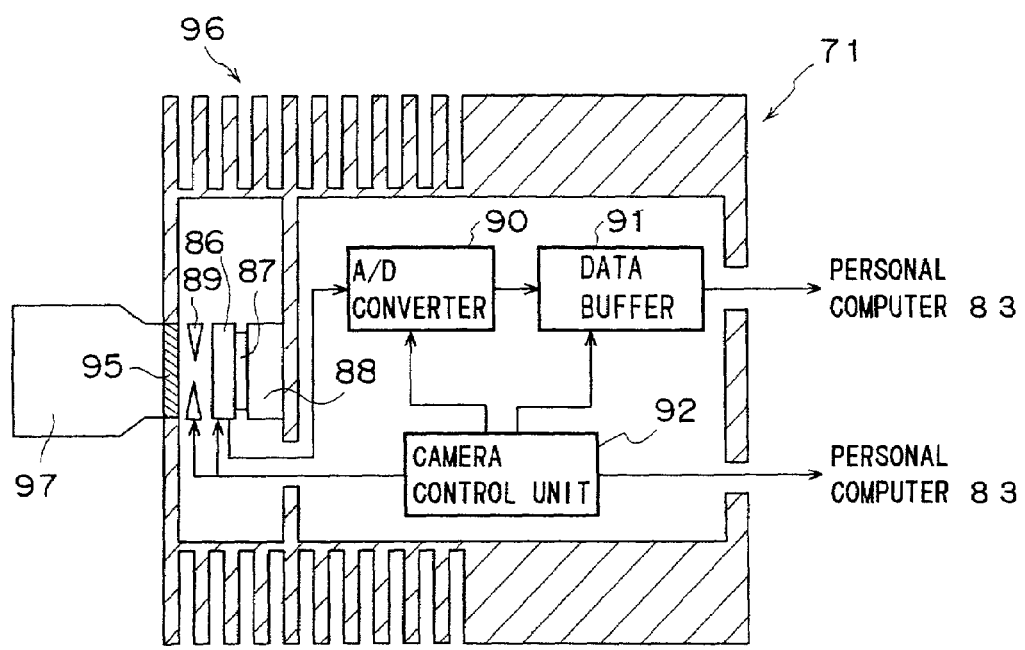
FIG. 15 is a schematic longitudinal cross sectional view showing a cooled CCD camera.

FIG. 15 is a schematic longitudinal cross sectional view showing the cooled CCD camera 81.

As shown in FIG. 15, the cooled CCD camera 81 includes a CCD 86, a heat transfer plate 87 made of metal such as aluminum, a Peltier element 88 for cooling the CCD 86, a shutter 89 disposed in front of the CCD 86, an A/D converter 90 for converting analog data produced by the CCD 86 to digital data, a data buffer 91 for temporarily storing the data digitized by the A/D converter 90, and a camera control circuit 92 for controlling the operation of the cooled CCD camera 81. An opening formed between the dark box 82 and the cooled CCD camera 81 is closed by a glass plate 95 and the periphery of the cooled CCD camera 81 is formed with heat dispersion fins 96 over substantially half its length for dispersing heat.

A camera lens 97 disposed in the dark box 82 is mounted on the front surface of the glass plate 95 disposed in the cooled CCD camera 81.

Figure 16:
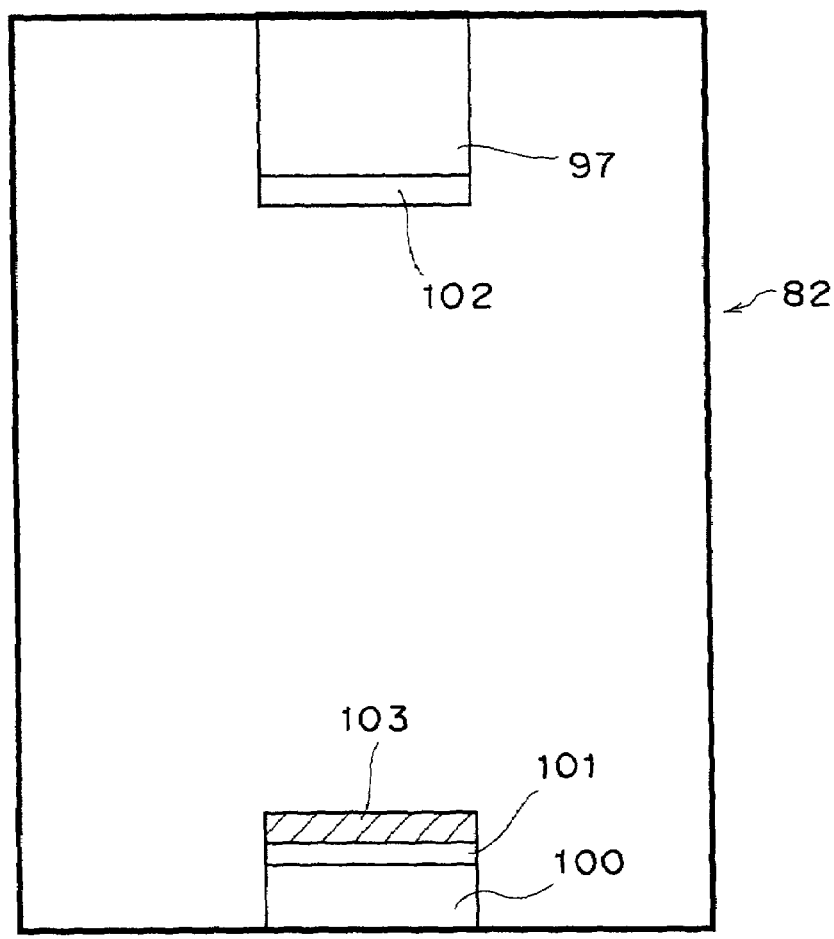
FIG. 16 is a schematic vertical cross sectional view showing a dark box.

FIG. 16 is a schematic vertical cross sectional view showing the dark box 82.

As shown in FIG. 16, the dark box 82 is equipped with a light emitting diode stimulating ray source 100 for emitting a stimulating ray. The light emitting diode stimulating ray source 100 is provided with a filter 101 detachably mounted thereon and a diffusion plate 102 mounted on the upper surface of the filter 101. The stimulating ray is emitted via the diffusion plate 102 toward a biochemical analysis unit (not shown) placed on the diffusion plate 102 so as to ensure that the biochemical analysis unit can be uniformly irradiated with the stimulating ray. The filter 101 has a property of cutting light components having a wavelength not close to that of the stimulating ray and harmful to the stimulation of a fluorescent substance and transmitting through only light components having a wavelength in the vicinity of that of the stimulating ray. A filter 102 for cutting light components having a wavelength in the vicinity of that of the stimulating ray is detachably provided on the front surface of the camera lens 97.

Figure 17:
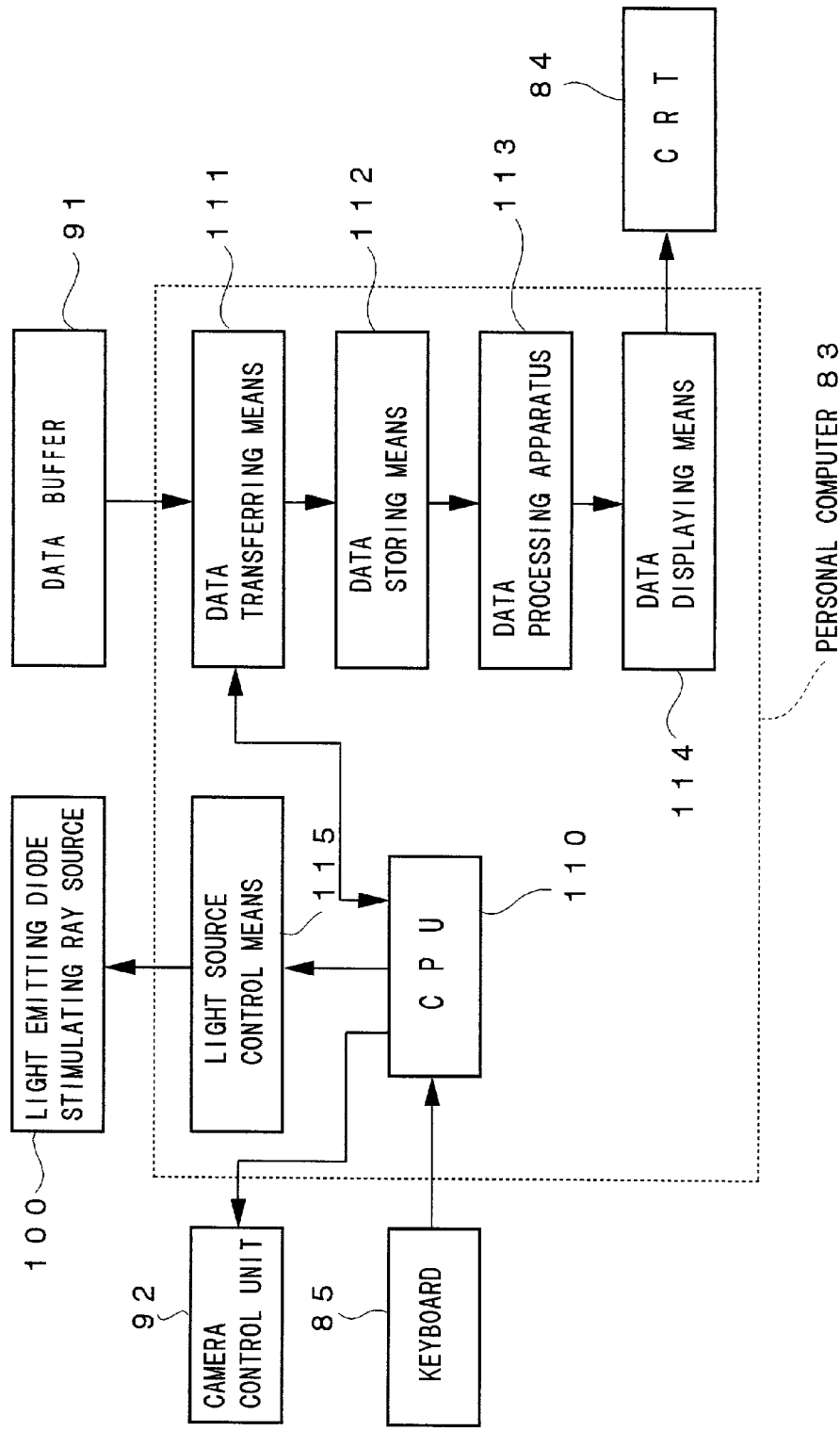
FIG. 17 is a block diagram of a personal computer and peripheral devices thereof.

FIG. 17 is a block diagram of the personal computer 83 and peripheral devices thereof.

As shown in FIG. 17, the personal computer 83 includes a CPU 110 for controlling the exposure of the cooled CCD camera 81, a data transferring means 111 for reading the data produced by the cooled CCD camera 81 from the data buffer 91, a storing means 112 for storing data, a data processing apparatus 113 for effecting data processing on the digital data stored in the data storing means 112, and a data displaying means 114 for displaying visual data on the screen of the CRT 84 based on the digital data stored in the data storing means 112. The light emitting diode stimulating ray source 100 is controlled by a light source control means 115 and an instruction signal can be input via the CPU 110 to the light source control means 115 through the keyboard 85. The CPU 110 is constituted so as to output various signals to the camera controlling circuit 93 of the cooled CCD camera 81.

The data producing system shown in FIGS. 14 to 17 is constituted so as to detect chemiluminescent emission generated by the contact of a labeling substance contained in the porous material 4 charged in a number of through-holes 3 formed in the biochemical analysis unit 1 and a chemiluminescent substrate, with the CCD 86 of the cooled CCD camera 81 through a camera lens 97, thereby producing chemiluminescence data, and irradiate the biochemical analysis unit 1 with a stimulating ray emitted from the light emitting diode stimulating ray source 100 and detect fluorescence released from a fluorescent substance such as a fluorescent dye contained in the porous material 4 charged in a number of through-holes 3 formed in the biochemical analysis unit 1 upon being stimulated, with the CCD 86 of the cooled CCD camera 81 through a camera lens 97, thereby producing fluorescence data.

When chemiluminescence data are to be read out, the filter 102 is removed and while the light emitting diode stimulating ray source 100 is kept off, the biochemical analysis unit 1 is placed on the diffusion plate 103, which is releasing chemiluminescent emission as a result of contact of a labeling substance contained in the porous material 4 charged in a number of through-holes 3 formed in the biochemical analysis unit 1 and a chemiluminescent substrate.

The lens focus is then adjusted by an operator using the camera lens 97 and the dark box 92 is closed.

When an exposure start signal is input by the operator through the keyboard 85, the exposure start signal is input through the CPU 110 to the camera control circuit 92 of the cooled CCD camera 81 so that the shutter 88 is opened by the camera control circuit 92, whereby the exposure of the CCD 86 is started.

Chemiluminescent emission released from the biochemical analysis unit 1 impinges on the light receiving surface of the CCD 86 of the cooled CCD camera 81 via the camera lens 97, thereby forming an image on the light receiving surface. The CCD 86 receives light of the thus formed image and accumulates it in the form of electric charges therein.

In this embodiment, since the substrate 2 of the biochemical analysis unit 1 is formed of a metal capable of attenuating radiation energy and light energy, it is possible to reliably prevent chemiluminescent emission released from the labeling substance from being scattered in the substrate 2 and mixed with chemiluminescent emission released from a labeling substance contained in porous material 4 charged in neighboring through-holes 3.

When a predetermined exposure time has passed, the CPU 110 outputs an exposure completion signal to the camera control circuit 92 of the cooled CCD camera 81.

When the camera controlling circuit 92 receives the exposure completion signal from the CPU 110, it transfers analog data accumulated in the CCD 86 in the form of electric charge to the A/D converter 90 to cause the A/D converter 90 to digitize the data and to temporarily store the thus digitized data in the data buffer 91.

At the same time, the CPU 110 outputs a data transfer signal to the data transferring means 111 to cause it to read out the digital data from the data buffer 91 of the cooled CCD camera 81 and to input them to the data storing means 112.

When the operator inputs a data producing signal through the keyboard 85, the CPU 110 outputs the digital data stored in the data storing means 112 to the data processing apparatus 113 and causes the data processing apparatus 113 to effect data processing on the digital data in accordance with the operator's instructions. The CPU 110 then outputs a data display signal to the displaying means 115 and causes the displaying means 115 to display biochemical analysis data on the screen of the CRT 84 based on the thus processed digital data.

On the other hand, when fluorescence data are to be read out, the biochemical analysis unit 1 is first placed on the diffusion plate 103.

The light emitting diode stimulating ray source 100 is then turned on by the operator and the lens focus is adjusted using the camera lens 97. The dark box 92 is then closed.

When the operator inputs an exposure start signal through the keyboard 85, the light emitting diode stimulating ray source 100 is again turned on by the light source control means 115, thereby emitting a stimulating ray toward the biochemical analysis unit 1. At the same time, the exposure start signal is input via the CPU 110 to the camera control circuit 92 of the cooled CCD camera 81 and the shutter 89 is opened by the camera control circuit 92, whereby the exposure of the CCD 86 is started.

The stimulating ray emitted from the light emitting diode stimulating ray source 100 passes through the filter 101, whereby light components of wavelengths not in the vicinity of that of the stimulating ray are cut. The stimulating ray then passes through the diffusion plate 103 to be made uniform light and the biochemical analysis unit 1 is irradiated with the uniform stimulating ray.

The fluorescence released from the biochemical analysis unit 1 impinges on the light receiving surface of the CCD 86 of the cooled CCD camera 81 through the filter 102 and the camera lens 97 and forms an image thereon. The CCD 86 receives light of the thus formed image and accumulates it in the form of electric charges therein. Since light components of wavelength equal to the stimulating ray wavelength are cut by the filter 102, only fluorescence released from the fluorescent substance contained in the porous material 4 charged in a number of the through-holes 3 formed in the biochemical analysis unit 1 is received by the CCD 86.

In this embodiment, since the substrate 2 of the biochemical analysis unit 1 is formed of a metal capable of attenuating radiation energy and light energy, it is possible to reliably prevent fluorescence released from the fluorescent substance such as a fluorescent dye from being scattered in the substrate 2 and mixed with fluorescence released from a fluorescent substance contained in porous material 4 charged in neighboring through-holes 3.

When a predetermined exposure time has passed, the CPU 110 outputs an exposure completion signal to the camera control circuit 92 of the cooled CCD camera 81.

When the camera controlling circuit 92 receives the exposure completion signal from the CPU 110, it transfers analog data accumulated in the CCD 86 in the form of electric charge to the A/D converter 90 to cause the A/D converter 90 to digitize the data and to temporarily store the thus digitized data in the data buffer 91.

At the same time, the CPU 110 outputs a data transfer signal to the data transferring means 111 to cause it to read out the digital data from the data buffer 91 of the cooled CCD camera 81 and to input them to the data storing means 112.

When the operator inputs a data producing signal through the keyboard 85, the CPU 110 outputs the digital data stored in the data storing means 112 to the data processing apparatus 113 and causes the data processing apparatus 113 to effect data processing on the digital data in accordance with the operator's instructions. The CPU 110 then outputs a data display signal to the displaying means 115 and causes the displaying means 115 to display biochemical analysis data on the screen of the CRT 84 based on the thus processed digital data.

In this embodiment, the biochemical analysis unit 1 includes the substrate 2 made of a metal capable of attenuating radiation energy and light energy and having flexibility formed with a number of the through-holes 3, and the porous material 4 is charged in the through-holes 3. Specific binding substances such as a plurality of cDNAs whose sequences are known but are different from each other are spotted into in a number of the through-holes 3 of the biochemical analysis unit 1 using the spotting device and are held by the porous material 4.

A hybridization solution 9 containing a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye is prepared and the biochemical analysis unit 1 is accommodated in the hybridization vessel 8 containing the thus prepared hybridization solution 9, whereby specific binding substances spotted in a number of the through-holes 3 charged with porous material 4 are hybridized with the substances derived from a living organism contained in the hybridization solution 9 and the specific binding substances are selectively labeled with a radioactive labeling substance, a fluorescent substance such as a fluorescent dye and a labeling substance which generates chemiluminescent emission when it contacts a chemiluminescent substrate.

When the stimulable phosphor sheet 10 is to be exposed to a radioactive labeling substance, the stimulable phosphor sheet 10 including the support 11 on one side of which a number of dot-like stimulable phosphor layer regions 12 are formed in the same pattern as that of a number of through-holes 3 formed in the biochemical analysis unit 1 is superposed on the biochemical analysis unit 1 in such a manner that each of the dot-like stimulable phosphor layer regions 12 formed in the stimulable phosphor sheet 10 is located in one of the many through-holes 3 formed in the biochemical analysis unit 1 and that the surface of each of the dot-like stimulable phosphor layer regions 12 comes into close contact with the surface of the porous material 4 charged in one of the through-holes 3, thereby exposing a number of the dot-like stimulable phosphor layer regions 12.

Therefore, according to this embodiment, since the substrate 2 of the biochemical analysis unit 1 is formed of a metal capable of attenuating radiation energy and light energy, when the stimulable phosphor sheet 10 is to be exposed, electron beams released from the radioactive labeling substance are prevented from being scattered in the substrate 2. Further, since each of a number of dot-like stimulable phosphor layer regions 12 formed in the stimulable phosphor sheet 10 is located in one of the many through-holes 3 formed in the biochemical analysis unit 1, the electron beams released from the radioactive labeling substance are prevented from being scattered in the dot-like stimulable phosphor layer region 12 and advancing to dot-like stimulable phosphor layer regions 12 located in neighboring through-holes. Accordingly, even when the through-holes 3 are formed in the substrate 2 at high density, it is possible to reliably expose a number of the dot-like stimulable phosphor layer regions 12 formed in the stimulable phosphor sheet 10 to only the radioactive labeling substance contained in the porous material 4 charged in the corresponding through-holes 3.

Furthermore, according to this embodiment, since the substrate 2 of the biochemical analysis unit 1 is formed of a metal capable of attenuating radiation energy and light energy, fluorescence released from a fluorescent substance such as a fluorescent dye as a result of being irradiated with a laser beam 24 or a stimulating ray emitted from the light emitting diode stimulating ray source 100, can be reliably prevented from being scattered in the substrate 2 and mixed with fluorescence released from a fluorescent substance such as a fluorescent dye contained in porous material 4 charged in neighboring through-holes 3. Therefore, even when the through-holes 3 are formed in the substrate 2 at high density, it is possible to reliably prevent noise caused by the scattering of fluorescence from being generated in biochemical analysis data produced by photoelectrically detecting fluorescence and improve the quantitative accuracy of biochemical analysis.

Furthermore, according to this embodiment, since the substrate 2 of the biochemical analysis unit 1 is formed of a metal capable of attenuating radiation energy and light energy, chemiluminescent emission released a labeling substance by the contact with a chemiluminescent substrate can be reliably prevented from being scattered in the substrate 2 and mixed with chemiluminescent emission released from a labeling substance contained in porous material 4 charged in neighboring through-holes 3. Therefore, even when the through-holes 3 are formed in the substrate 2 at high density, it is possible to reliably prevent noise caused by the scattering of chemiluminescent emission from being generated in biochemical analysis data produced by photoelectrically detecting chemiluminescent emission and improve the quantitative accuracy of biochemical analysis.

Further, according to this embodiment, since the substrate 2 of the biochemical analysis unit 1 is formed of a metal having flexibility, the biochemical analysis unit 1 can be bent and accommodated in the hybridization vessel 8 so as to be aligned with the inner wall surface thereof, whereby specific binding substances are selectively hybridized with substances derived from a living organism. Therefore, hybridization can be accomplished using a small amount of the hybridization solution 9.

Furthermore, according to this embodiment, since the substrate 2 of the biochemical analysis unit 1 is formed of a metal, it is hardly stretched and shrunk even when it is subjected to liquid processing such as hybridization and, therefore, it is possible to easily and accurately superpose the stimulable phosphor sheet 10 on the biochemical analysis unit 1 so that each of the dot-like stimulable phosphor layer regions 12 formed in the stimulable phosphor sheet 10 is located in one of the many through-holes 3 formed in the biochemical analysis unit 1 and that the surface of each of the dot-like stimulable phosphor layer regions 12 comes into close contact with the surface of the porous material 4 charged in one of the through-holes 3, thereby exposing the dot-like stimulable phosphor layer regions 12.

Figure 18:
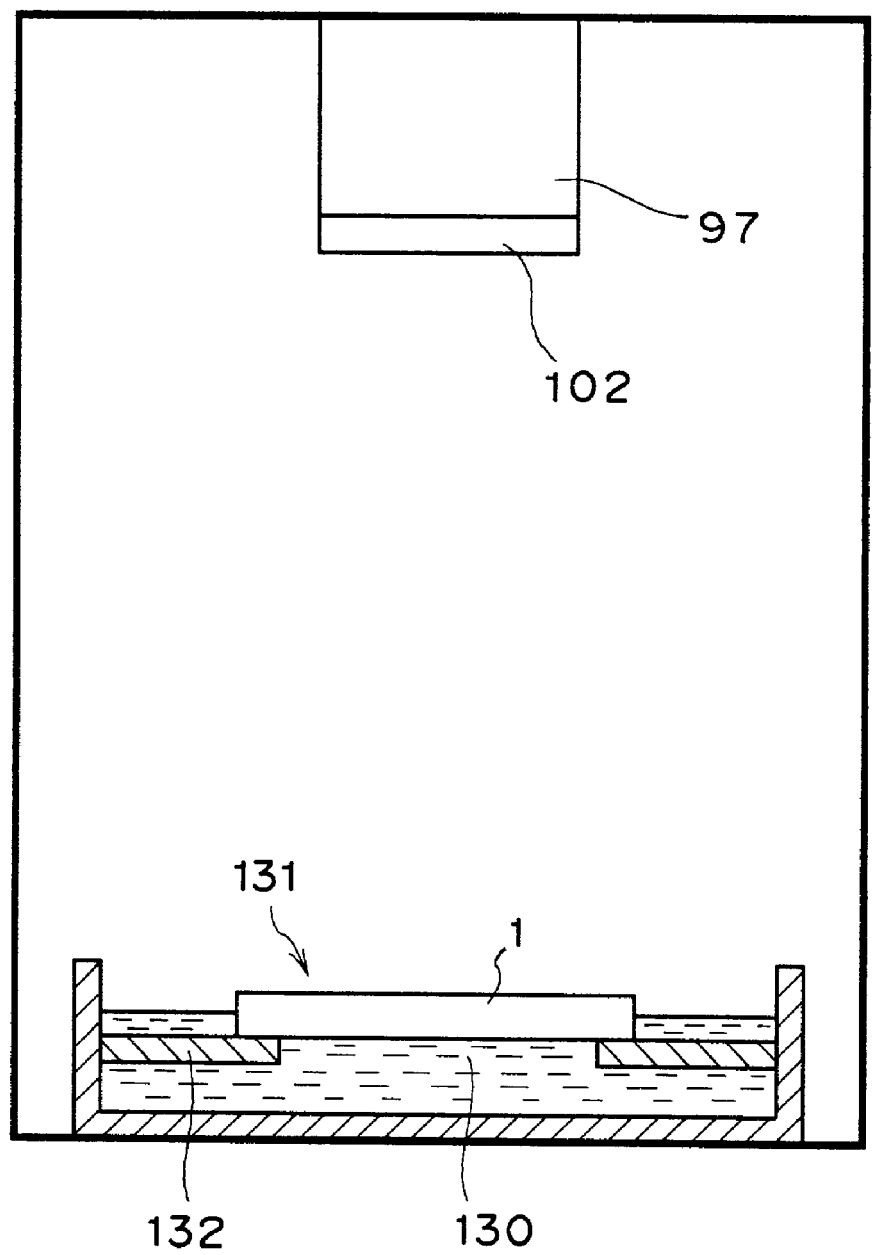
FIG. 18 is a schematic vertical cross sectional view showing another example of a dark box.

FIG. 18 is a schematic vertical cross sectional view showing another example of a dark box.

As shown in FIG. 18, at the bottom of a dark box 82 according to this embodiment, a vessel 131 containing a solution 130 containing a chemiluminescent substrate is provided and the inner wall surface of the vessel 131 is formed with support members 132 for supporting the biochemical analysis unit 1.

When chemiluminescence data are to be read out, it is preferable for improving the quantitative accuracy to keep the labeling substance contained in the porous material 4 charged in a number of the through-holes 3 of the biochemical analysis unit 1 and the chemiluminescent substrate constantly in contact with each other so as to cause release of chemiluminescent emission having a predetermined intensity. Therefore, in the dark box 82 according to this embodiment, since the support members 132 enable the biochemical analysis unit 1 to be kept constantly in contact with the solution 130 containing a chemiluminescent substrate accommodated in the vessel 131 provided at the bottom of the dark box 82 and chemiluminescent emission can be detected by the cooled CCD camera 81, it is possible to markedly improve the quantitative accuracy of biochemical analysis.

Figure 19:
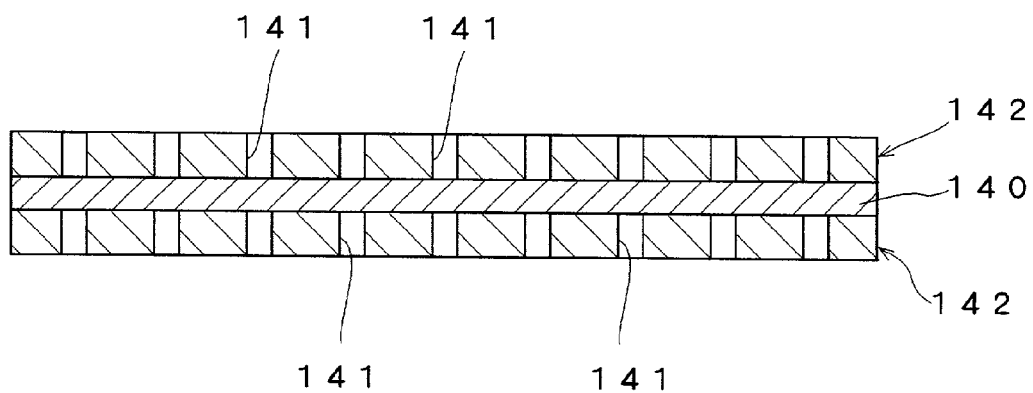
FIG. 19 is a schematic longitudinal cross sectional view showing a biochemical analysis unit which is another embodiment of the present invention.

FIG. 19 is a schematic longitudinal cross sectional view showing a biochemical analysis unit which is another embodiment of the present invention.

As shown in FIG. 19, a biochemical analysis unit 1 includes an absorptive substrate 140 formed of absorptive material such as nylon-6 and is formed by closely contacting perforated plates 142, 142 made of a metal capable of attenuating radiation energy and light energy and having flexibility and formed with a number of through-holes 141.

Although not accurately shown in FIG. 19, in this embodiment, similarly to the substrate 2 according to the previous embodiment, about 10,000 through-holes 141 having a size of about 0.01 cm$^2$ are regularly formed at a density of about 10,000 per cm$^2$ in the perforated plates 142, 142 and a number of absorptive regions 144 are formed by the absorptive substrate 140 located in the through-holes 141.

In this embodiment, when biochemical analysis is to be performed, specific binding substances such as a plurality of cDNAs whose sequences are known but are different from each other are spotted using the spotting device shown in FIG. 2 onto a number of the absorptive regions 144 formed on the absorptive substrate 140 via a number of the through-holes 141 formed in the perforated plates 142, 142.

When hybridization is to be performed, similarly to the previous embodiment, the biochemical analysis unit 1 including a number of the absorptive regions 144 into which specific binding substances have been spotted is inserted into the hybridization vessel 7, whereby the specific binding substances are selectively hybridized with a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye contained in the hybridization solution 9.

As a result of the hybridization, fluorescence data of a fluorescent substance such as a fluorescent dye and chemiluminescence data of a substance derived from a living organism labeled with a labeling substance which generates chemiluminescent emission when it contacts a chemiluminescent substrate are recorded in the absorptive regions 144 formed on the absorptive substrate 140.

When the stimulable phosphor sheet 10 is to be exposed to a radioactive labeling substance, as shown in FIG. 4, the stimulable phosphor sheet 10 formed with a number of dot-like stimulable phosphor layer regions 12 is superposed on the biochemical analysis unit 1. The dot-like stimulable phosphor layer regions 12 are formed in the stimulable phosphor sheet 10 in the same regular pattern as that of a number of the through-holes 141 formed in the perforated plate 142.

Figure 20:
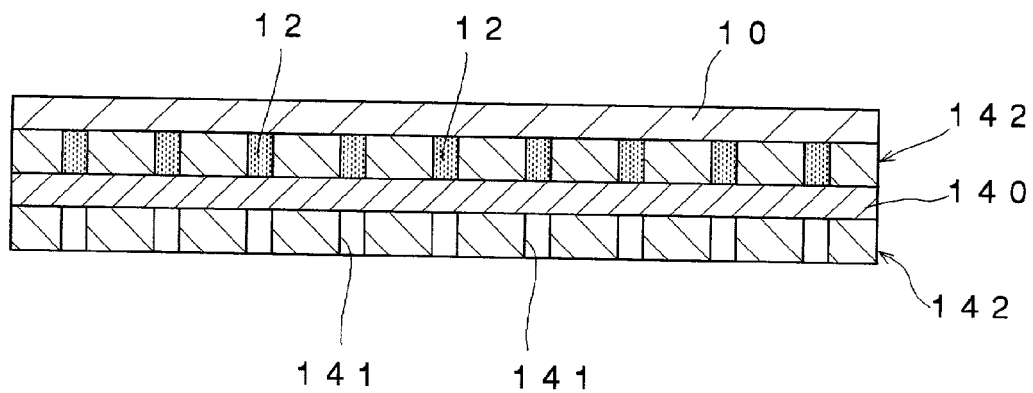
FIG. 20 is a schematic cross-sectional view showing a method for exposing a number of dot-like stimulable phosphor layer regions formed on a stimulable phosphor sheet by a radioactive labeling substance contained in absorptive regions formed on a porous substrate.

FIG. 20 is a schematic cross-sectional view showing a method for exposing a number of the dot-like stimulable phosphor layer regions 12 formed on the stimulable phosphor sheet 10 to a radioactive labeling substance contained in a number of the absorptive regions 144 formed on the absorptive substrate 140.

As shown in FIG. 20, when the stimulable phosphor sheet 10 is to be exposed, the stimulable phosphor sheet 10 is superposed on the biochemical analysis unit 1 in such a manner that each of the dot-like stimulable phosphor layer regions 12 formed in the stimulable phosphor sheet 10 is located in one of the through-holes 3 formed in one of the perforated plates 142 of the biochemical analysis unit 1 and that the surface of each of the dot-like stimulable phosphor layer regions 12 comes into close contact with the surface of the absorptive region 144.

Since specific binding substances are spotted using the spotting device on the absorptive regions 144 formed on the absorptive substrate 140 via the perforated plate 142, the surface of each of the dot-like stimulable phosphor layer regions 12 is accurately located in close contact with the spot-like regions formed on the surface of the absorptive substrate 140 and selectively labeled with a radioactive labeling substance.

In this manner, the surface of each of the dot-like stimulable phosphor layer regions 12 is kept in close contact with the surface of the absorptive regions 144 formed on the absorptive substrate 140 for a predetermined time period, whereby a number of the dot-like stimulable phosphor layer regions 12 formed in the stimulable phosphor sheet 10 are exposed to the radioactive labeling substance contained in a number of the absorptive regions 144.

During the exposure operation, electron beams are released from the radioactive labeling substance. However, since the perforated plate 140 is formed of a metal capable of attenuating radiation energy and light energy, electron beams released from the radioactive labeling substance contained in the individual absorptive regions 144 formed on the absorptive substrate 140 are prevented from being mixed with electron beams released from the radioactive labeling substance contained in neighboring absorptive regions 144 formed on the absorptive substrate 140. Further, since each of a number of dot-like stimulable phosphor layer regions 12 formed in the stimulable phosphor sheet 10 is located in one of the through-holes 141 formed in the perforated plate 142, the electron beams released from the radioactive labeling substance are reliably prevented from being scattered in the dot-like stimulable phosphor layer region 12 and advancing to the dot-like stimulable phosphor layer regions 12 located in neighboring through-holes 141. Therefore, it is possible to reliably expose a number of the dot-like stimulable phosphor layer regions 12 formed in the stimulable phosphor sheet 10 to only the radioactive labeling substance contained in the absorptive regions 144 formed on the absorptive substrate 140 via corresponding through-holes 141 of the perforated plate 142.

In this manner, radiation data of a radioactive labeling substance are recorded in a number of the dot-like stimulable phosphor layer regions 12 formed in the stimulable phosphor sheet 10.

Therefore, in the case where biochemical analysis data are produced by irradiating the dot-like stimulable phosphor layer regions 12 formed in the support 11 of the stimulable phosphor sheet 10 at high density and exposed to a radioactive labeling substance with a stimulating ray and photoelectrically detecting stimulated emission released from the dot-like stimulable phosphor layer regions 12, and substances derived from a living organism are analyzed, it is possible to effectively prevent noise caused by the scattering of electron beams released from the radioactive labeling substance from being generated in biochemical analysis data.

On the other hand, chemiluminescence data of a labeling substance which generates chemiluminescent emission when it contacts a chemiluminescent substrate or fluorescence data of a fluorescent substance such as a fluorescent dye recorded in a number of the absorptive regions 144 formed on the absorptive substrate 140 are read out by the data producing system shown in FIGS. 14 to 17, thereby producing biochemical analysis data.

Since the perforate plate 142 formed with a number of the through-holes 141 is located on the side of the camera lens 97 with respect to the absorptive substrate 140 so as to be in close contact with the absorptive substrate 140, chemiluminescent emission released from a labeling substance which generates chemiluminescent emission when it contacts a chemiluminescent substrate or fluorescence released from a fluorescent substance contained in the individual absorptive regions 144 can be reliably prevented from being mixed with chemiluminescent emission released from the labeling substance which generates chemiluminescent emission when it contacts a chemiluminescent substrate or fluorescence released from the fluorescent substance contained in neighboring absorptive regions 144 formed on the absorptive substrate 140 and, therefore, it is possible to effectively prevent noise caused by the scattering of chemiluminescent emission or fluorescence from being generated in biochemical analysis data produced by photoelectrically detecting chemiluminescent emission or fluorescence.

According to this embodiment, since the perforated plate 142 is made of a metal capable of attenuating radiation energy and light energy, electron beams released from the radioactive labeling substance contained in the individual absorptive regions 144 formed on the absorptive substrate 140 can be reliably prevented from being mixed with electron beams released from the radioactive labeling substance contained in neighboring absorptive regions 144 formed on the absorptive substrate 140 and since each of a number of dot-like stimulable phosphor layer regions 12 formed in the stimulable phosphor sheet 10 is located in one of the through-holes 141 formed in the biochemical analysis unit 1, electron beams released from the radioactive labeling substance are prevented from being scattered in the dot-like stimulable phosphor layer region 12 and advancing to the dot-like stimulable phosphor layer regions 12 located in neighboring through-holes 141. Accordingly, it is possible to reliably expose a number of the dot-like stimulable phosphor layer regions 12 formed in the stimulable phosphor sheet 10 to only the radioactive labeling substance contained in the corresponding absorptive regions 144 formed on the absorptive substrate 140 via the corresponding through-holes 141 of the perforated plate 142. Therefore, in the case where biochemical analysis data are produced by irradiating the dot-like stimulable phosphor layer regions 12 formed in the support 11 of the stimulable phosphor sheet 10 at high density and exposed to a radioactive labeling substance with a stimulating ray and photoelectrically detecting stimulated emission released from the dot-like stimulable phosphor layer regions 12, and substances derived from a living organism are analyzed, it is possible to effectively prevent noise caused by the scattering of electron beams released from the radioactive labeling substance from being generated in biochemical analysis data.

On the other hand, according to this embodiment, since the perforate plate 142 formed with a number of the through-holes 141 is located on the side of the camera lens 97 with respect to the absorptive substrate 140 so as to be in close contact with the absorptive substrate 140, chemiluminescent emission released from a labeling substance which generates chemiluminescent emission when it contacts a chemiluminescent substrate or fluorescence released from a fluorescent substance contained the individual absorptive regions 144 formed on the absorptive substrate 140 can be reliably prevented from being mixed with chemiluminescent emission released from the labeling substance which generates chemiluminescent emission when it contacts a chemiluminescent substrate or fluorescence released from the fluorescent substance contained in neighboring absorptive regions 144 formed on the absorptive substrate 140 and, therefore, it is possible to effectively prevent noise caused by the scattering of chemiluminescent emission or fluorescence from being generated in biochemical analysis data produced by photoelectrically detecting chemiluminescent emission or fluorescence.

Figure 21:
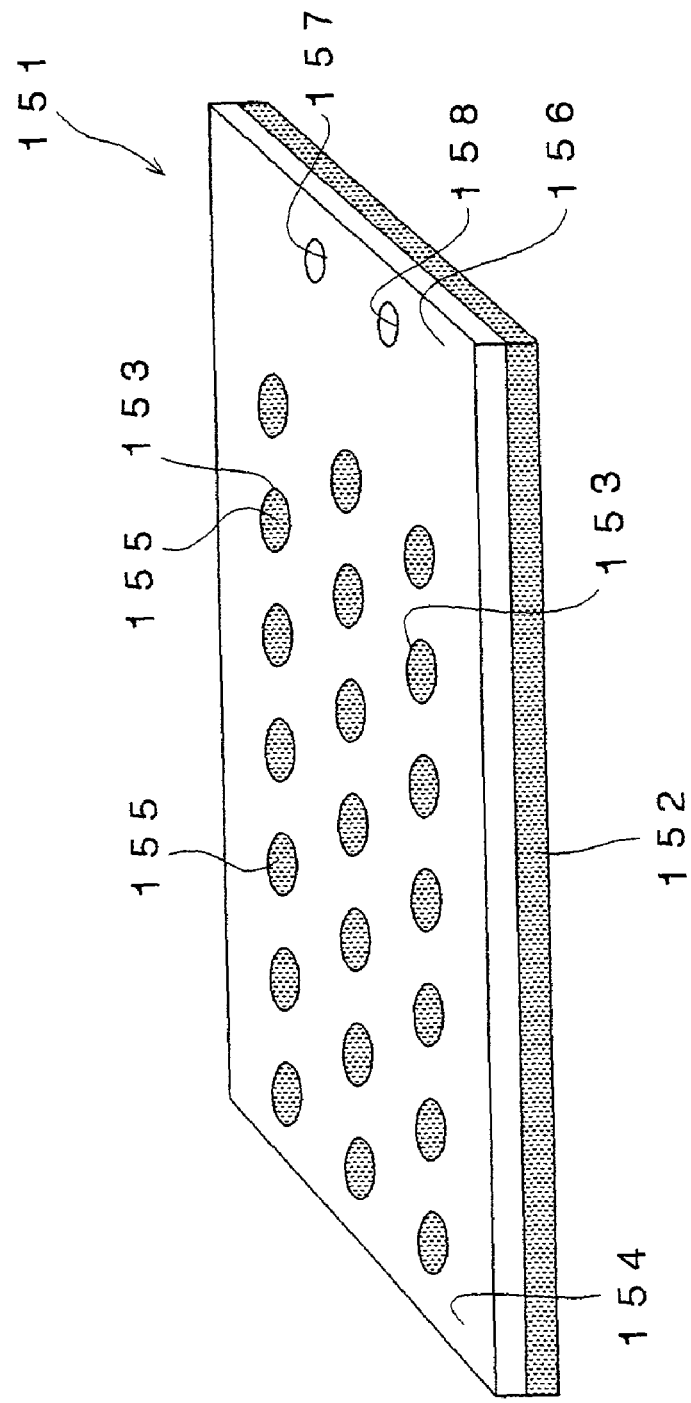
FIG. 21 is a schematic perspective view of a biochemical analysis unit which is a further preferred embodiment of the present invention.

FIG. 21 is a schematic perspective view of a biochemical analysis unit which is a further preferred embodiment of the present invention.

A biochemical analysis unit 151 shown in FIG. 21 includes an absorptive substrate 152 made of absorptive material such as nylon-6 and a perforated plate 154 made of a metal such as aluminum and formed with a number of substantially circular through-holes 153 regularly and at a high density, and the absorptive substrate 152 and the perforated plate 154 are in close contact with each other.

Although not accurately shown in FIG. 21, similarly to the biochemical analysis unit shown in FIG. 19, in this embodiment, about 10,000 through-holes 153 having a size of about 0.01 mm$^2$ are regularly formed at a density of about 5,000 per cm$^2$ in the perforated plate 154 and a number of absorptive regions 155 are regularly formed by the absorptive substrate 152 in every through-holes 153.

As shown in FIG. 21, the perforated plate 154 is formed with a gripping portion 156 in this embodiment.

As shown in FIG. 21, the perforated plate 154 of the biochemical analysis unit 151 according to this embodiment is formed with a pair of positioning through-holes 157, 158 in the vicinity of one side portion.

Figure 22:
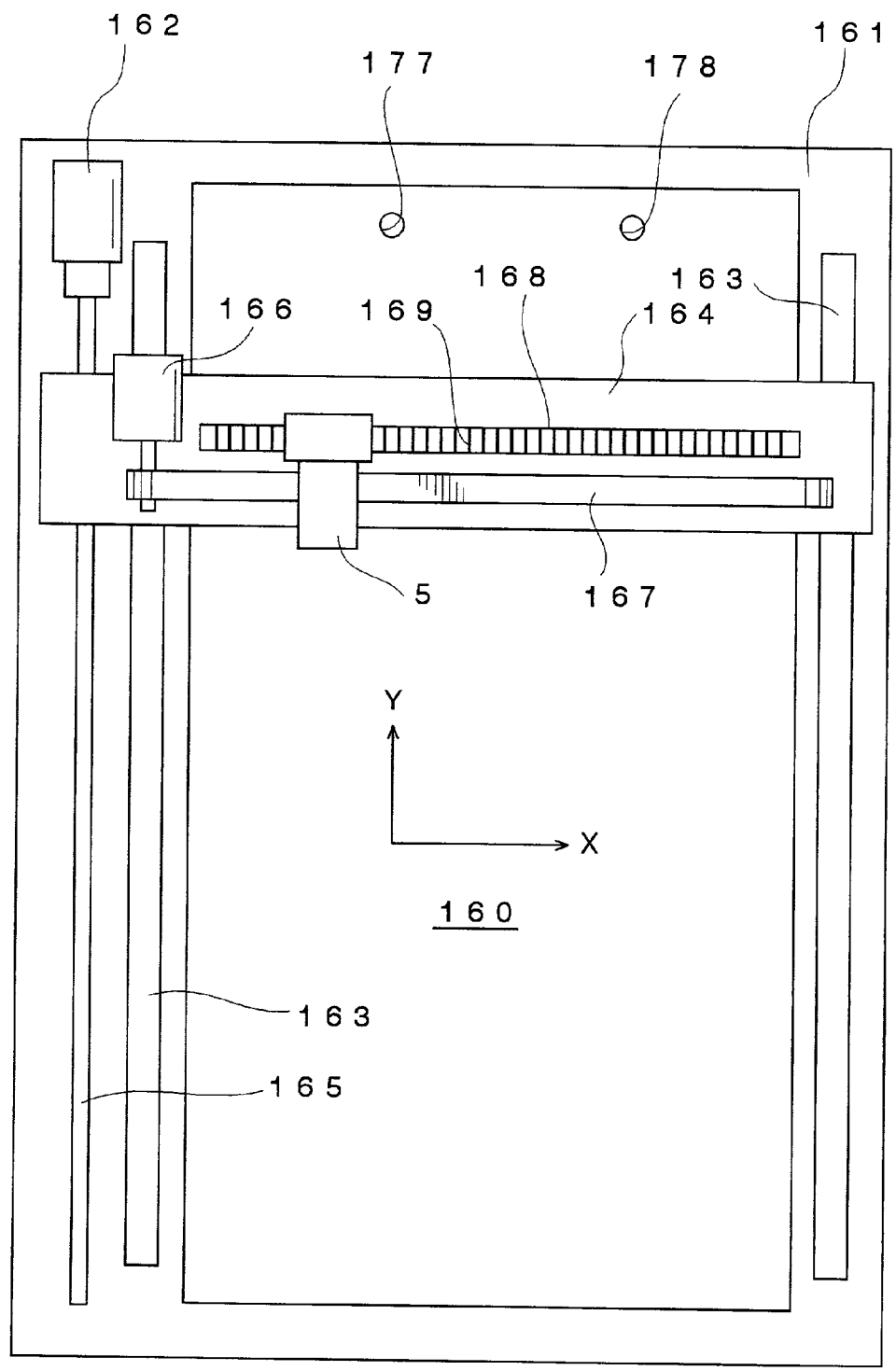
FIG. 22 is a schematic plan view showing another example of a spotting device.

FIG. 22 is a schematic plan view showing another example of a spotting device.

As shown in FIG. 22, a spotting device according to this embodiment is provided with a drive mechanism and the drive mechanism of the spotting device is mounted on a frame 161 fixed to a base plate 160 on which the biochemical analysis unit 151, onto which specific binding substances such as cDNA are to be spotted, is to be set.

As shown in FIG. 22, a sub-scanning pulse motor 162 and a pair of rails 163, 163 are fixed on the frame 161 and a movable base plate 164 is further provided so as to be movable along the pair of rails 163, 163 in the sub-scanning direction indicated by an arrow Y in FIG. 22.

The movable base plate 164 is formed with a threaded hole (not shown) and a threaded rod 165 rotated by the sub-scanning pulse motor 162 is engaged with the inside of the hole.

A main scanning pulse motor 166 is provided on the movable base plate 164. The main scanning pulse motor 165 is adapted for intermittently driving an endless belt 167 at a predetermined pitch.

The spotting head 5 of the spotting device is fixed to the endless belt 167 and when the endless belt 167 is driven by the main scanning pulse motor 166, the spotting head 5 is moved in the main scanning direction indicated by an arrow X in FIG. 22.

Although not shown in FIG. 22, the spotting head 5 includes an injector 6 for ejecting a solution of specific binding substances toward the biochemical analysis unit 151 and a CCD camera 7.

In FIG. 22, the reference numeral 168 designates a linear encoder for detecting the position of the spotting head 5 in the main scanning direction and the reference numeral 169 designates slits of the linear encoder 168.

As shown in FIG. 22, two positioning pins 177, 178 are uprightly formed on the base plate 160 of the spotting device at positions corresponding to those of the two positioning through-holes 157, 158 formed in the perforated plate 154 of the biochemical analysis unit 151. Placement of the biochemical analysis unit 151 at a substantially constant position on the base plate 160 of the spotting device is ensured by placing the biochemical analysis unit 151 on the base plate 160 of the spotting device so that the two positioning pins 177, 178 formed on the base plate 160 of the spotting device are inserted into the corresponding positioning through-holes 157, 158.

Figure 23:
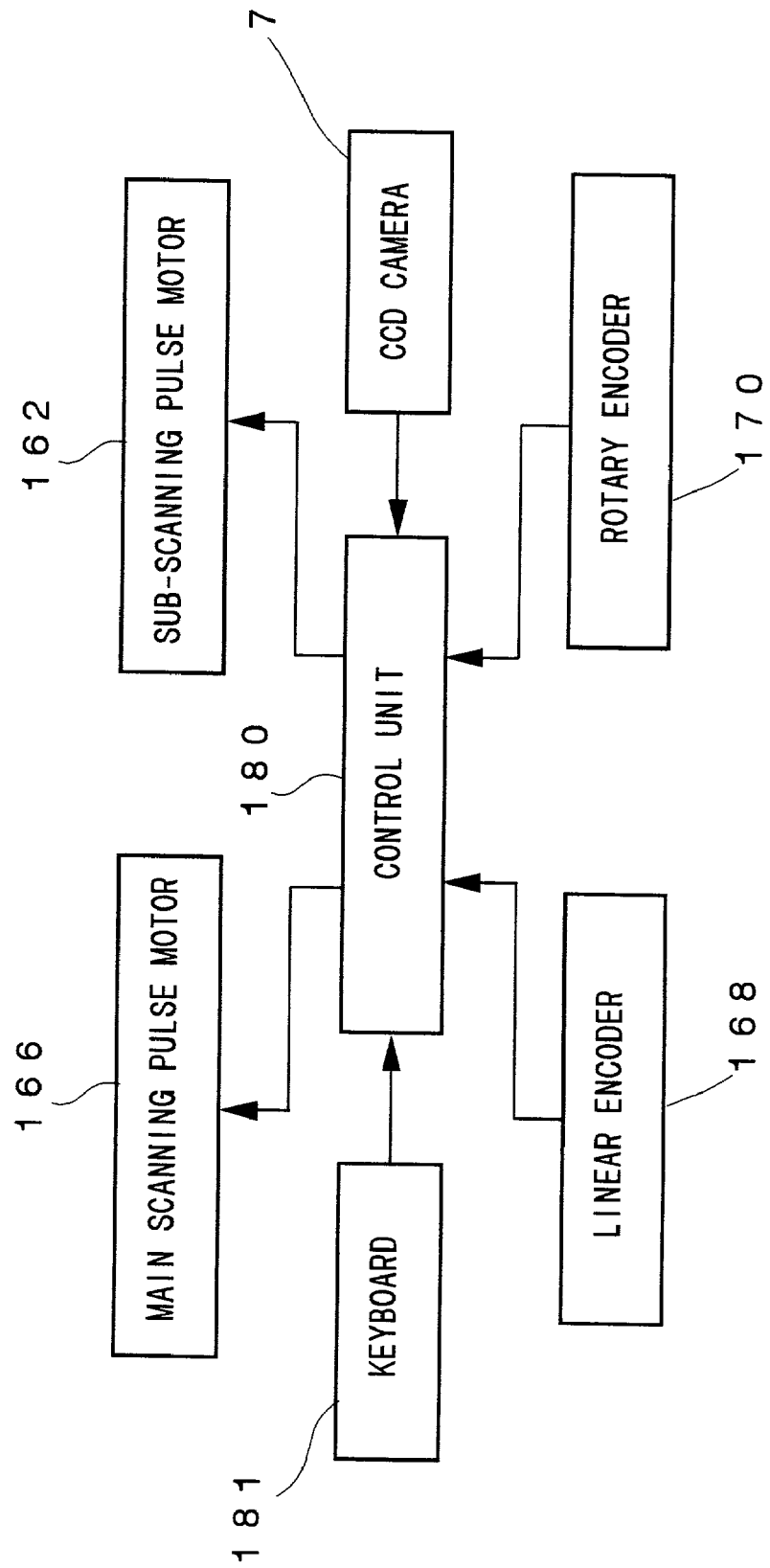
FIG. 23 is a block diagram showing a control system, an input system, a drive system and a detection system of a spotting device.

FIG. 23 is a block diagram showing a control system, an input system, a drive system and a detection system of the spotting device.

As shown in FIG. 23, the control system of the spotting device includes a control unit 180 for controlling the whole operation of the spotting device and the input system of the spotting device includes a keyboard 181.

The drive system of the spotting device includes a main scanning pulse motor 166 and a sub-scanning pulse motor 162, and the detection system of the spotting device includes a linear encoder 166 for detecting the position of the spotting head 5 in the main scanning direction, a rotary encoder 170 for detecting the amount of rotation of the rod 165 and a CCD camera 7.

Specific binding substances such as cDNA are spotted by the thus constituted spotting device onto a number of absorptive regions 155 formed in the biochemical analysis unit 151 according to this embodiment in the following manner.

The biochemical analysis unit 151 is first placed on the base plate 160 of the spotting device so that the two positioning pins 177, 178 formed on the base plate 160 of the spotting device enter the corresponding positioning through-holes 157, 158.

In this embodiment, it is ensured in this manner that the biochemical analysis unit 151 is placed at a substantially constant position on the base plate 160 of the spotting device. However, since each of the absorptive regions has a size of only about 0.01 mm$^2$ in this embodiment, it cannot be ensured that the centers of the absorptive regions 155 of the biochemical analysis unit 151 thus placed on the base plate 160 are exactly aligned with the main scanning direction and the sub-scanning direction of the spotting head 5.

Therefore, the spotting device according to this embodiment is constituted so as to detect in advance the relative positional relationship between the position of the biochemical analysis unit 151 placed on the base plate 160 and the positions of the spotting head 5 to be moved in main scanning direction and the sub-scanning direction, and to move the spotting head 5 by the main scanning pulse motor 166 and the sub-scanning pulse motor 162 so that the injector 6 can accurately spot specific binding substances onto the absorptive regions 155.

When a spotting operation start signal is input by a user through the keyboard 181 and the spotting operation start signal is input to the control unit 180, the control unit 180 outputs a drive signal to the main scanning pulse motor 166, thereby moving the spotting head 5 located at a reference position in the main scanning direction indicated by an arrow X in FIG. 22 and then outputs a drive signal to the sub-scanning pulse motor 162, thereby moving the spotting head 5 in the sub-scanning direction indicated by an arrow Y in FIG. 22.

While the spotting head 5 is being moved in the main scanning direction indicated by an arrow X and in the main scanning direction indicated by an arrow X, the control unit 180 monitors detection signals input from the CCD camera 7, thereby detecting four corner portions of the biochemical analysis unit 151, calculates coordinate values of the four corner portions of the biochemical analysis unit 151 in a coordinate system whose origin is the reference position of the spotting head 5, and stores them in a memory (not shown).

When the four corner portions of the biochemical analysis unit 151 are detected and the coordinate values thereof are stored in the memory, the control unit 180 calculates coordinate values of the respective absorptive regions 155 formed in the biochemical analysis unit 151 based on the coordinate values of the four corner portions of the biochemical analysis unit 151 in the coordinate system whose origin is the reference position of the spotting head 5 and stores them in the memory (not shown).

When the coordinate values of the respective absorptive regions 155 formed in the biochemical analysis unit 151 have been calculated in the coordinate system whose origin is the reference position of the spotting head 5 and stored in the memory, the control unit 180 outputs drive signals to the main scanning pulse motor 166 and the sub-scanning pulse motor 162, thereby returning the spotting head 5 to the original reference position.

In the case where specific binding substances ejected from the injector 6 of the spotting head 5 are accurately spotted at the position the tip end portion of the injector 6 faces, specific binding substances can be accurately spotted onto the respective absorptive regions 155 formed in the biochemical analysis unit 151 by ejecting specific binding substances from the injector 6 of the spotting head 5 in the above-described manner based on the coordinate values of the respective absorptive regions 155 of the biochemical analysis unit 151 in the coordinate system determined so that the reference position of the spotting head 5 is the origin thereof. However, in the case where specific binding substances ejected from the injector 6 of the spotting head 5 are spotted at a position deviating in the X direction and/or the Y direction from the position the tip end portion of the injector 6 faces, even if specific binding substances are ejected from the injector 6 of the spotting head 5 in the above-described manner based on the coordinate values of the respective absorptive regions 155 of the biochemical analysis unit 151 in the coordinate system determined so that the reference position of the spotting head 5 is the origin thereof, it is impossible to accurately spot specific binding substances onto the respective absorptive regions 155 formed in the biochemical analysis unit 151.

In view of the above, in this embodiment, specific binding substances are ejected from the injector 6 of the spotting head 5 returned to the reference position thereof toward the surface of the biochemical analysis unit 151, whereby the position of the thus spotted specific binding substances is detected by the CCD camera 7, and amounts of deviation from the position the tip end portion of the injector 6 faces in the X direction and the Y direction are calculated by the control unit 180 based on a detection signal of the CCD camera 7 and the calculated amounts of deviation are stored in the memory.

Figure 24:
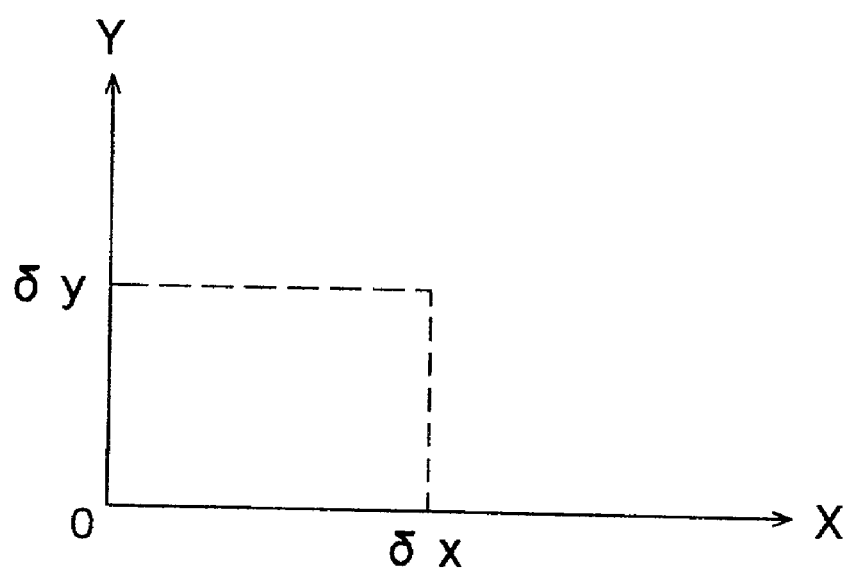
FIG. 24 is a schematic partial plan view showing a biochemical analysis unit in which specific binding substances are spotted from an injector located a reference position thereof.

More specifically, as shown in FIG. 24, specific binding substances are ejected from the injector 6 of the spotting head 5 located at the reference position thereof toward the surface of the biochemical analysis unit 151 and the position of the thus spotted specific binding substances is detected by the CCD camera 7. The control unit 180 then calculates an amount of deviation δ x in the X direction and an amount of deviation δ y in the Y direction from the position O the tip end portion of the injector 6 faces based on a detection signal from the CCD camera and stores them in the memory.

Since the amount of deviation δ x in the X direction and the amount of deviation δ y in the Y direction of the position of spotted specific binding substances from the position O the tip end portion of the injector 6 faces are inherent in the respective injector 6 of the spotting head 5, it follows that the position of spotted specific binding substances ejected from the injector 6 toward the surface of the biochemical analysis unit 151 when the spotting head 5 is located at a position other than the reference position thereof deviates from the position O the tip end portion of the injector 6 faces by δ x in the X direction and by δ y in the Y direction.

Then, based on the coordinate values of the four corner portions of the biochemical analysis unit 151 and the coordinate values of the respective absorptive regions 155 formed in the biochemical analysis unit 151 in the coordinate system whose origin is the reference position of the spotting head 5 and the amount of deviation δ x in the X direction and the amount of deviation δ y in the Y direction of the position of spotted specific binding substances, the control unit 180 calculates drive pulses to be sent to the main scanning pulse motor 166 and the sub-scanning pulse motor 162 in order to move the spotting head 5 to positions where the tip end portion of the injector 6 of the spotting head 5 faces the respective absorptive regions 155 and stores driving pulse data in the memory.

In this embodiment, a number of absorptive regions 155 of the biochemical analysis unit 151 are formed one in every through-hole 153 regularly formed in the perforated plate 154. Therefore, the drive pulses to be sent to the main scanning pulse motor 166 and the sub-scanning pulse motor 162 in order to move the spotting head 5 to a position where the tip end portion of the injector 6 of the spotting device faces the third absorptive region 155 to which specific binding substances are to be spotted and from there to each successive position where the tip end portion of the injector 6 of the spotting device faces an absorptive region 155 to which specific binding substances are to be spotted are equal to the drive pulses to be sent to the main scanning pulse motor 166 and the sub-scanning pulse motor 162 in order to move the spotting head 5 from the position where the tip end portion of the injector 6 of the spotting device faces the first absorptive region 155 to which specific binding substances are to be spotted to the position where the tip end portion of the injector 6 of the spotting device faces the second absorptive region 155 to which specific binding substances are to be spotted. Accordingly, it is sufficient to calculate drive pulses to be sent to the main scanning pulse motor 166 and the sub-scanning pulse motor 162 in order to move the spotting head 5 from the reference position of the spotting head 5 to the position where the tip end portion of the injector 6 of the spotting device faces the first absorptive region 155 to which specific binding substances are to be spotted, calculate drive pulses to be sent to the main scanning pulse motor 166 and the sub-scanning pulse motor 162 in order to move the spotting head 5 from the position where the tip end portion of the injector 6 of the spotting device faces the first absorptive region 155 to which specific binding substances are to be spotted to the position where the tip end portion of the injector 6 of the spotting device faces the second absorptive region 155 to which specific binding substances are to be spotted, and store the calculated drive pulse data in the memory.

When drive pulses to be sent to the main scanning pulse motor 166 and the sub-scanning pulse motor 162 in order to move the spotting head 5 to the position where the tip end portion of the injector 6 of the spotting device faces the respective absorptive regions 155 have been calculated and drive pulse data have been stored in the memory, the control unit 180 sends predetermined drive pulses to the main scanning pulse motor 166 and the sub-scanning pulse motor 162 based on the drive pulse data stored in the memory, thereby intermittently moving the spotting head 5. When the spotting head 5 has reached the positions where it faces the respective absorptive regions 155 formed in the biochemical analysis unit 151, the control unit 180 outputs drive stop signals to the main scanning pulse motor 166 and the sub-scanning pulse motor 162, thereby stopping the spotting head 5 and outputs a spot signal to the injector 6 of the spotting head 5, thereby causing it to spot specific binding substances.

In the case where the spotting head 5 is to be moved to the position where the tip end portion of the injector 6 of the spotting head 5 faces the second or a subsequent absorptive region 155 to which specific binding substances are to be spotted, the spotting head 5 is moved at predetermined pitches in the main scanning direction indicated by the arrow X and in the sub-scanning direction indicated by the arrow Y.

The spotting head 5 is intermittently moved by the main scanning pulse motor 166 and the sub-scanning pulse motor 162 in this manner and specific binding substances are successively spotted onto the absorptive regions 155 formed in the biochemical analysis unit 151.

According to this embodiment, the position of the biochemical analysis unit 151 with respect to the spotting head 5 is detected in advance by the CCD camera 7, the coordinate values of the respective absorptive regions 155 are calculated by the control unit 180 using the reference position of the spotting head 5 as the origin of the coordinate system, and the calculated coordinate values are stored in the memory. Specific binding substances are ejected toward the surface of the biochemical analysis unit 151 from the injector 6 of the spotting head 5 located at the reference position thereof and the position where the specific binding substances are spotted is detected by the CCD camera 7, whereby the amount of deviation δ x in the X direction and the amount of deviation δ y in the Y direction of the position of the spotted specific binding substances from the position O where the tip end portion of the injector 6 faces are calculated by the control unit 180 and stored in the memory. The control unit 180 calculates, based on these data, drive pulses to be sent to the main scanning pulse motor 166 and the sub-scanning pulse motor 162 in order to move the spotting head 5 to the position where the tip end portion of the injector 6 of the spotting device faces the respective absorptive regions 155 and stores the drive pulse data in the memory. When specific binding substances are to be spotted, the control unit 180 sends predetermined drive pulses to the main scanning pulse motor 166 and the sub-scanning pulse motor 162 based on the drive pulse data stored in the memory. When the spotting head 5 has reached the positions where it faces the respective absorptive regions 155 formed in the biochemical analysis unit 151, the control unit 180 outputs drive stop signals to the main scanning pulse motor 166 and the sub-scanning pulse motor 162, thereby stopping the spotting head 5 and outputs a spot signal to the injector 6 of the spotting head 5, thereby causing it to specific binding substances. Therefore, even when the biochemical analysis unit 151 is not accurately set on the base plate 160 so as to have a predetermined positional relationship with the spotting device, specific binding substances such as cDNA can be reliably spotted in the respective absorptive regions 155 formed in the biochemical analysis unit 151.

Further, according to this embodiment, since the biochemical analysis unit 151 includes the perforated plate 154 made of aluminum and the perforated plate 154 is formed with the gripping portion 156, the biochemical analysis unit 151 can be very easily handled when specific binding substances are spotted, during hybridization or during exposure operation.

Furthermore, according to this embodiment, the biochemical analysis unit 151 and the stimulable phosphor sheet 10 can be desirably positioned for exposure utilizing the two positioning through-holes 157, 158 formed in the vicinity of one side portion of the perforated plate 154.

Figure 25:
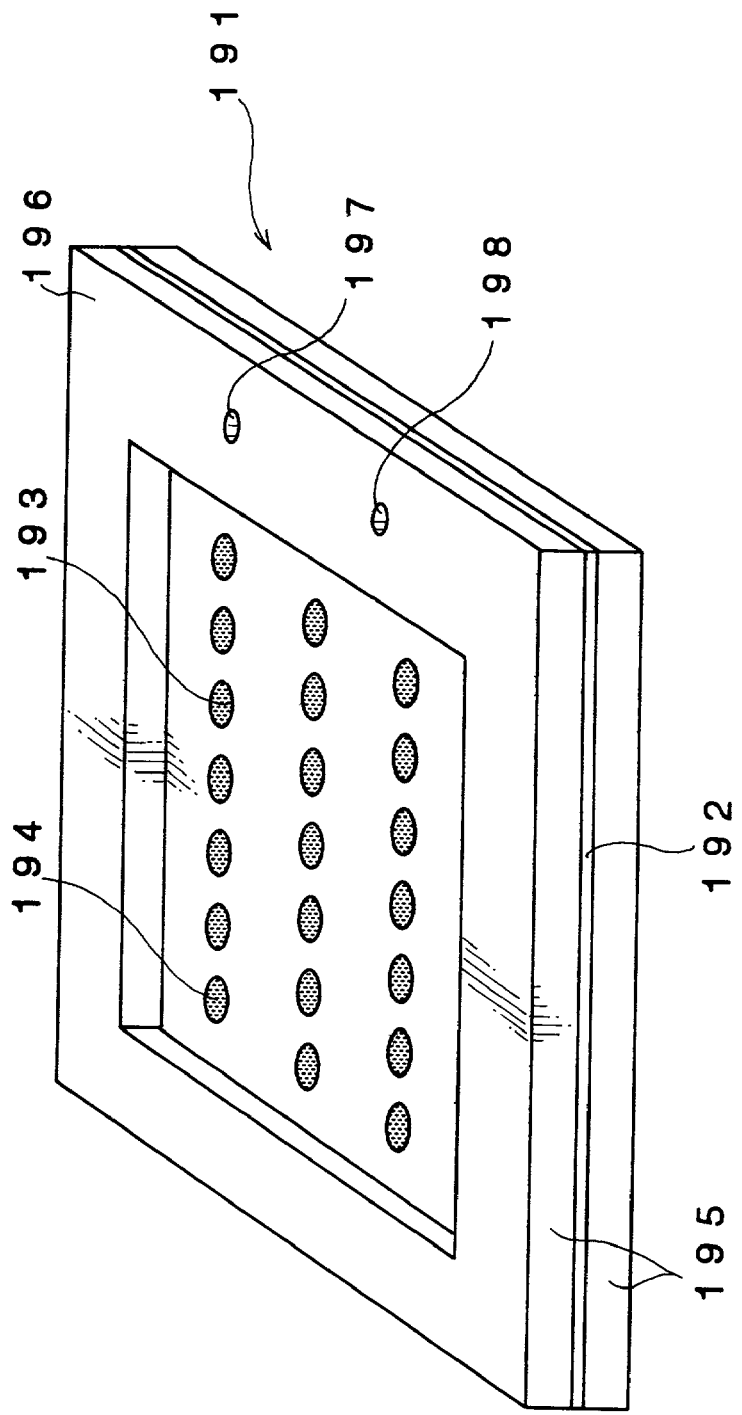
FIG. 25 is a schematic perspective view of a biochemical analysis unit which is a further preferred embodiment of the present invention.

FIG. 25 is a schematic perspective view of a biochemical analysis unit which is a further preferred embodiment of the present invention.

Similarly to the biochemical analysis unit 1 shown in FIG. 1, a biochemical analysis unit 191 includes a substrate 192 made of aluminum and formed with a number of substantially circular through-holes 193 regularly and at a high density, and a number of absorptive regions 194 are formed by charging absorptive material such as nylon-6 in every through-hole 193.

The biochemical analysis unit 191 further includes a frame member 196 including a pair of plate-like members 195, 195 and adapted for holding the peripheral portion of the substrate 192 therebetween and carrying the substrate 192. The plate-like members 195, 195 are formed of rigid material.

Similarly to the embodiment shown in FIG. 21, as shown in FIG. 25, the frame member 196 is formed with two positioning through-hole 197, 198.

According to this embodiment, since the substrate 192 of the biochemical analysis unit 191 is held between the frame member 196 formed of rigid material, the biochemical analysis unit 191 can be very easily handled when specific binding substances are spotted, during hybridization or during exposure operation.

Furthermore, according to this embodiment, since the frame member 196 of the biochemical analysis unit 191 is formed with the two positioning through-holes 197, 198, specific binding substances can be accurately spotted onto a number of the absorptive regions 194 utilizing the spotting device shown in FIG. 22.

Moreover, according to this embodiment, since the substrate 192 of the biochemical analysis unit 191 is held between the frame member 196 formed of rigid material, the biochemical analysis unit 191 and the stimulable phosphor sheet 10 can be desirably positioned for exposure utilizing the frame member 196 formed of rigid material.

The present invention has thus been shown and described with reference to specific embodiments. However, it should be noted that the present invention is in no way limited to the details of the described arrangements but changes and modifications may be made without departing from the scope of the appended claims.

For example, in the above-described embodiments, as specific binding substances, cDNAs each of which has a known base sequence and is different from the others are used. However, specific binding substances usable in the present invention are not limited to cDNAs but all specific binding substances capable of specifically binding with a substance derived from a living organism such as a hormone, tumor marker, enzyme, antibody, antigen, abzyme, other protein, a nuclear acid, cDNA, DNA, RNA or the like and whose sequence, base length, composition and the like are known, can be employed in the present invention as a specific binding substance.

Further, in the above-described embodiments, although the substrate 2 or the perforated plate 142 is made of a metal, it is sufficient to make the substrate 2 or the perforated plate 142 of a material capable of attenuating radiation energy and light energy. Therefore, the invention is not limited to forming the substrate 2 or the perforated plate 142 of a metal and the substrate 2 and the perforated plate 142 may instead be formed of a ceramic material or a plastic material.

Furthermore, in the above-described embodiments, although the substrate 2 or the perforated plate 142 has flexibility, it is not absolutely necessary to form the substrate 2 or the perforated plate 142 so as to be flexible.

Moreover, in the above-described embodiments, the substrate 2 or the perforated plate 142 of the biochemical analysis unit 1 is made of a material capable of attenuating radiation energy and light energy. However, in the case where biochemical analysis is performed only by detecting radiation data recorded in the dot-like stimulable phosphor layer regions 12 of the stimulable phosphor sheet 10, the substrate 2 or the perforated plate 142 may be made of a material capable of transmitting light but attenuating radiation energy. On the other hand, in the case where biochemical analysis is performed only by detecting chemiluminescence data or fluorescence data, the substrate 2 or the perforated plate 142 may be made of a material capable of transmitting radiation but attenuating light energy. Therefore, it is not absolutely necessary to form the substrate 2 or the perforated plate 142 of a material capable of attenuating radiation energy and light energy.

Further, a porous material is charged in a number of the through-holes 3 formed in the substrate 2 to form the absorptive regions 4 in the embodiment shown in FIGS. 1 to 18. However, it is possible to form a number of recesses in the substrate 2, instead of the through-holes 3, and to charge or embed a porous material to form the absorptive regions 4.

Furthermore, in the above-described embodiments, although about 10,000 of the through-holes 3 or through-holes 143 having a size of about 0.01 cm² are regularly formed in the substrate 2 or the perforated plate 142 at a density of about 10,000/cm², the number or size of the through-holes 3 or through-holes 143 may be arbitrarily selected in accordance with the purposes. Preferably, 10 or more of the through-holes 3 or through-holes 143 having a size of 5 cm² or less are formed in the substrate 2 or the perforated plate 142 at a density of 10/cm² or less.

Moreover, in the above-described embodiments, although about 10,000 of the through-holes 3 or through-holes 143 having a size of about 0.01 cm² are regularly formed in the substrate 2 or the perforated plate 142 at a density of about 10,000/cm², it is not absolutely necessary to regularly form the through-holes 3 or through-holes 143 in the substrate 2 or the perforated plate 142.

Further, in the above-described embodiments, a hybridization solution 9 containing a substance derived from a living organism labeled with a radioactive labeling substance, a substance derived from a living organism labeled with a labeling substance which generates chemiluminescent emission when it contacts a chemiluminescent substrate and a substance derived from a living organism labeled with a fluorescent substance such as a fluorescent dye is prepared and hybridized with specific binding substances spotted in the absorptive region 4. However, it is not absolutely necessary for substances derived from a living organism to be labeled with a radioactive labeling substance, a fluorescent substance and a labeling substance which generates chemiluminescent emission when it contacts a chemiluminescent substrate and it is sufficient for substances derived from a living organism to be labeled with at least one kind of a labeling substance selected from a group consisting of a radioactive labeling substance, a fluorescent substance and a labeling substance which generates chemiluminescent emission when it contacts a chemiluminescent substrate.

Furthermore, in the above-described embodiments, specific binding substances are hybridized with substances derived from a living organism labeled with a radioactive labeling substance, a fluorescent substance and a labeling substance which generates chemiluminescent emission when it contacts a chemiluminescent substrate. However, it is not absolutely necessary to hybridize substances derived from a living organism with specific binding substances and substances derived from a living organism may be specifically bound with specific binding substances by means of antigen-antibody reaction, receptor-ligand reaction or the like instead of hybridization.

Moreover, in the above-described embodiments, a number of the dot-like stimulable phosphor layer regions 12 are formed on one surface of the support 11 of the stimulable phosphor sheet 10 in the same pattern as that of a number of the through-holes 3 formed in the biochemical analysis unit 1 of the same pattern as that of a number of the through-holes 141 formed in the perforated plate 142. However, it is not absolutely necessary to form the dot-like stimulable phosphor layer regions 12 and a stimulable phosphor layer may be uniformly formed on one surface of the support 11 of the stimulable phosphor sheet 10.

Further, the dot-like stimulable phosphor layer regions 12 are exposed to a radioactive labeling substance by superposing the biochemical analysis unit 1 and the stimulable phosphor sheet 10 so that the absorption regions 4 formed in the through-holes 4 of the biochemical analysis unit 1 and the dot-like stimulable phosphor layer regions 12 of the stimulable phosphor sheet 10 are in close contact with each other in the embodiment shown in FIGS. 1 to 18 and the dot-like stimulable phosphor layer regions 12 are exposed to a radioactive labeling substance by superposing the biochemical analysis unit 1 and the stimulable phosphor sheet 10 so that the absorption regions 144 formed on the absorptive substrate 140 of the biochemical analysis unit 1 and the dot-like stimulable phosphor layer regions 12 of the stimulable phosphor sheet 10 are in close contact with each other in the embodiment shown in FIGS. 19 and 20. However, it is sufficient for the dot-like stimulable phosphor layer regions 12 to be exposed to a radioactive labeling substance by superposing the biochemical analysis unit 1 and the stimulable phosphor sheet 10 so that the dot-like stimulable phosphor layer regions 12 of the stimulable phosphor sheet 10 face the absorption regions 4 formed in the through-holes 4 of the biochemical analysis unit 1 or the absorptive substrate 140 of the biochemical analysis unit 1 and it is not absolutely necessary to expose the dot-like stimulable phosphor layer regions 12 to a radioactive labeling substance by keeping the dot-like stimulable phosphor layer regions 12 of the stimulable phosphor sheet 10 in close contact with the absorption regions 4 formed in the through-holes 4 of the biochemical analysis unit 1 or the absorptive regions 144 formed on the absorptive substrate 140 of the biochemical analysis unit 1.

Moreover, in the above-described embodiments, although a number of the dot-like stimulable phosphor layer regions 12 of the stimulable phosphor sheet 10 are formed on the surface of the support 11, it is not absolutely necessary to form a number of the dot-like stimulable phosphor layer regions 12 on the surface of the support 11. A number of dot-like stimulable phosphor layer regions 12 may be formed by forming a number of through-holes in the support 11 and charging or embedding stimulable phosphor into a number of the through-holes or forming a number of recesses in the support 11 and charging or embedding stimulable phosphor into a number of the recesses.

Furthermore, in the above-described embodiments, although a number of the dot-like stimulable phosphor layer regions 12 of the stimulable phosphor sheet 10 are formed so that the surface thereof is located above the surface of the support 11, a number of the dot-like stimulable phosphor layer regions 12 may be formed so that the surface thereof is flush with the surface of the support 11 or that the surface thereof is located below the surface of the support 11.

Moreover, in the above-described embodiments, although the support 11 of the stimulable phosphor sheet 10 is made of stainless, it is sufficient for the support 11 to be made of a material capable of attenuating radiation energy and light energy and the support 11 can be formed of either inorganic compound material or organic compound material and is preferably formed of metal material, ceramic material or plastic material. Illustrative examples of inorganic compound materials include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4, 10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials Further, the biochemical analysis unit 1 is constituted in the embodiment shown in FIGS. 19 and 20 by bringing the perforated plates 142, 142 formed with a number of the through-holes 141 into close contact with the both sides of the absorptive substrate 140 formed of an absorptive material such as nylon-6. However, it is not absolutely necessary to constitute the biochemical analysis unit 1 by abutting the perforated plates 142, 142 against both sides of the absorptive substrate 140 and the biochemical analysis unit 1 may be constituted by abutting the perforated plate 142 formed with a number of the through-holes 141 against only one surface of the absorptive substrate 140.

Furthermore, in the above-described embodiments, biochemical analysis data are produced by reading radiation data of a radioactive labeling substance recorded in a number of the dot-like stimulable phosphor layer regions 12 formed in the stimulable phosphor sheet 10 and fluorescence data of a fluorescent substance such as a fluorescent dye recorded in the absorptive regions 4 formed in the through-holes 3 of the biochemical analysis unit 1 using the scanner shown in FIGS. 6 to 13. However, it is not absolutely necessary to produce biochemical analysis data by reading radiation data of a radioactive labeling substance and fluorescence data of a fluorescent substance using a single scanner and biochemical analysis data may be produced by reading radiation data of a radioactive labeling substance and fluorescence data of a fluorescent substance using separate scanners.

Moreover, in the above-described embodiments, biochemical analysis data are produced by reading radiation data of a radioactive labeling substance recorded in a number of the dot-like stimulable phosphor layer regions 12 formed in the stimulable phosphor sheet 10 and fluorescence data of a fluorescent substance such as a fluorescent dye recorded in the absorptive regions 4 formed in the through-holes 3 of the biochemical analysis unit 1 using the scanner shown in FIGS. 6 to 13. However, it is not absolutely necessary to read radiation data of a radioactive labeling substance using the scanner shown in FIGS. 6 to 13 and any scanner constituted so as to scan and stimulate a number the dot-like stimulable phosphor layer regions 12 with a laser beam 24 may be used for reading radiation data of a radioactive labeling substance.

Further, although the scanner shown in FIGS. 6 to 13 includes the first laser stimulating ray source 1, the second laser stimulating ray source 2 and the third laser stimulating ray source 3, it is not absolutely necessary for the scanner to include three laser stimulating ray sources.

Furthermore, in the above-described embodiments, biochemical analysis data are produced by reading chemiluminescence data of a labeling substance which generates chemiluminescent emission when it contacts a chemiluminescent substrate recorded in the absorptive regions 4 formed in the through-holes 3 of the biochemical analysis unit 1 using the data producing system which can also read fluorescence data. However, it is not absolutely necessary to produce biochemical analysis data by reading chemiluminescence data using the data producing system which can also read fluorescence data and in the case where only chemiluminescence data of a labeling substance which generates chemiluminescent emission when it contacts a chemiluminescent substrate recorded in the absorptive regions 4 formed in the through-holes 3 of the biochemical analysis unit 1 are read, the light emitting diode stimulating ray source 100, the filter 101, the filter 102 and the diffusion plate 102 can be omitted from the data producing system.

Moreover, in the above-described embodiments, all of the dot-like stimulable phosphor layer regions 12 formed in the stimulable phosphor sheet 10 or the entire surface of the biochemical analysis unit 1 is scanned with a laser beam 24 to excite stimulable phosphor or a fluorescent substance such as a fluorescent dye by moving the optical head 35 using a scanning mechanism in the X direction and the Y direction in FIG. 12. However, all of the dot-like stimulable phosphor layer regions 12 formed in the stimulable phosphor sheet 10 or the entire surface of the biochemical analysis unit 1 can be scanned with a laser beam 24 to excite stimulable phosphor or a fluorescent substance such as a fluorescent dye by moving the stage 40 in the X direction and the Y direction in FIG. 12, while holding the stage 40 stationary. Further, the optical head 35 may be moved in one of the X direction and the Y direction in FIG. 12, while the stage 40 is moved in the other direction.

Furthermore, although the perforated mirror 34 formed with the hole 33 is used in the scanner shown in FIGS. 6 to 13, the mirror can be formed with a coating capable of transmitting the laser beam 24 instead of the hole 33.

Moreover, the photomultiplier 50 is employed as a light detector to photoelectrically detect fluorescent light or stimulated emission in the scanner shown in FIGS. 6 to 13. However, it is sufficient for the light detector used in the present invention to be able to photoelectrically detect fluorescent light or stimulated emission and it is possible to employ a light detector such as a line CCD or a two-dimensional CCD instead of the photomultiplier 50.

Further, in the above-described embodiments, specific binding substances such as cDNAs are spotted using the spotting device including an injector 6 and a CCD camera 7 so that when the tip end portion of the injector 6 and the center of the through-hole 3 or the through-hole 141 into which a specific binding substance is to be spotted are determined to coincide with each other as a result of viewing them using the CCD camera 7, the specific binding substance such as cDNA is spotted from the injector 6. However, specific binding substances such as cDNAs can be spotted by detecting the positional relationship between the through-holes 3 or the through-holes 141 formed in the biochemical analysis unit 1 and the tip end portion of the injector 6 in advance and two-dimensionally moving the biochemical analysis unit 1 or the tip end portion of the injector 6 so that the tip end portion of the injector 6 coincides with each of the through-holes 3 or the through-holes 141.

Furthermore, although the spotting head 5 of the spotting device includes the injector 6 for injecting a solution of specific binding substances toward the biochemical analysis unit 1, 151 and the CCD camera 7 in the above described embodiments, the spotting head 5 may include, instead of the injector 6, a spotting pin for spotting specific binding substances onto the biochemical analysis unit 1, 151.

Moreover, although the spotting head 5 of the spotting device includes the CCD camera 7, it is not absolutely necessary for the spotting head 5 to include the CCD camera 7 and other solid-state imaging devices such as a CID (charge injection device), a PDA (photodiode array), a MOS type imaging device and the like may be used.

Further, in the embodiment shown in FIGS. 21 to 24, although four corner portions of the biochemical analysis unit 151 are detected and the coordinate values thereof are calculated using the reference position of the spotting head 5 as the origin of the coordinate system, it is sufficient to determine the relative positional relationship between the biochemical analysis unit 151 and the spotting head 5 of the spotting device and it is not absolutely necessary to detect four corner portions of the biochemical analysis unit 151 and calculate the coordinate values thereof. It is possible to detect diagonally opposite corner portions of the biochemical analysis unit 151, calculate the coordinate values thereof using the reference position of the spotting head 5 as the origin of the coordinate system, calculate drive pulses to be sent to the main scanning pulse motor 166 and the sub-scanning pulse motor 162, and move the spotting head 5.

Furthermore, in the embodiment shown in FIGS. 21 to 24, setting of the biochemical analysis unit 151 at a substantially constant position on the base plate 160 is ensured by placing the biochemical analysis unit 151 on the base plate 160 so that two positioning pins 177, 178 formed on the base plate 160 of the spotting device are inserted into two positioning through-holes 157, 158 of the biochemical analysis unit 151. Alternatively, three or more positioning pins may be formed on the base plate 160 and corresponding through-holes be formed in the biochemical analysis unit 151. Further, exact positioning of the biochemical analysis unit 151 on the base plate 160 of the spotting device may be ensured, not by providing the two positioning pins 157, 158, but instead by forming, for instance, a pair of guides having side portions perpendicular to each other on the surface of the base plate 160 of the spotting device and abutting side surfaces adjacent to the corner portion of the biochemical analysis unit 151 against each of the guide.

Moreover, in the embodiment shown in FIGS. 21 to 24, the spotting head 5 is moved in the main scanning direction and the sub-scanning direction by moving the base plate 164 along the pair of rails 163, 163 in the sub-scanning direction indicated by the arrow Y in FIG. 22 by the sub-scanning pulse motor 162 fixed on the frame 161 and intermittently driving the endless belt 167 at a predetermined pitch by the main scanning pulse motor 166 provided on the movable base plate 164, thereby moving the spotting head 5 fixed on the endless belt 167 in the main scanning direction indicated by the arrow X in FIG. 22. However, the mechanism for driving the spotting head 5 is not limited to this arrangement but the spotting head 5 may be moved in the main scanning direction and the sub-scanning direction using any of various appropriate mechanisms.

Further, in the embodiment shown in FIGS. 21 to 24, although the biochemical analysis unit 151 is held stationary and the spotting head 5 is moved in the main scanning direction and the sub-scanning direction with respect to the biochemical analysis unit 151 placed on the base plate 160, it is possible to hold the spotting head 5 stationary and move the base plate 160 on which the biochemical analysis unit 151 is placed in the main scanning direction and the sub-scanning direction. Moreover, it is also possible to move the spotting head 5 in the main scanning direction or the sub-scanning direction and move the base plate 160 on which the biochemical analysis unit 151 is placed in the sub-scanning direction or the main scanning direction.

Furthermore, in the embodiment shown in FIGS. 21 to 24, since a number of the absorptive regions 155 are regularly formed in the biochemical analysis unit 151, the spotting head 5 is moved at constant pitches without using the CCD camera after the coordinate values of a number of the absorptive regions 155 are determined using the CCD camera 7 in the coordinate system in which the reference position of the spotting head 5 is used as the origin thereof. However, for instance, in the case where a number of the absorptive regions 155 are not regularly formed in the biochemical analysis unit 151, it is possible to spot specific binding substances by confirming the position to which specific binding substances are to be spotted using the CCD camera 7 while the spotting head 5 is being moved.

Moreover, in the above described embodiments, the scanner is provided with the first laser stimulating ray source 21 for emitting a laser beam having a wavelength of 640 nm, the second laser stimulating ray source 22 for emitting a laser beam having a wavelength of 532 nm and the third laser stimulating ray source 23 for emitting a laser beam having a wavelength of 473 nm. However, it is not absolutely necessary to use a laser stimulating ray source as a stimulating ray source and a light emitting diode stimulating ray source may be used as a stimulating ray source instead of any of the laser stimulating ray sources. Further, a halogen ramp may be used as any of the stimulating ray source provided that light components of a wavelength that does not contribute to stimulation are cut by a spectral filter.

According to the present invention, it is possible to provide a biochemical analysis unit which can prevent noise caused by the scattering of electron beams released from a radioactive labeling substance from being generated in biochemical analysis data even in the case of forming spots of specific binding substances on the surface of a carrier at high density, which can specifically bind with a substance derived from a living organism and whose sequence, base length, composition and the like are known, specifically binding the spot-like specific binding substances with a substance derived from a living organism labeled with a radioactive substance to selectively label the spot-like specific binding substances with a radioactive substance, thereby obtaining a biochemical analysis unit, superposing the thus obtained biochemical analysis unit and a stimulable phosphor layer together, exposing the stimulable phosphor layer to a radioactive labeling substance, irradiating the stimulable phosphor layer with a stimulating ray to excite the stimulable phosphor, photoelectrically detecting the stimulated emission released from the stimulable phosphor layer to produce biochemical analysis data, and analyzing the substance derived from a living organism.

Further, according to the present invention, it is possible to provide a biochemical analysis unit which can prevent noise caused by the scattering of chemiluminescent emission and/or fluorescence released from a labeling substance which generates chemiluminescent emission when it contacts a chemiluminescent substrate and/or a fluorescent substance from being generated in biochemical analysis data even in the case of forming spots of specific binding substances on the surface of a carrier at high density, which can specifically bind with a substance derived from a living organism and whose sequence, base length, composition and the like are known, specifically binding the spot-like specific binding substances with a substance derived from a living organism labeled with, in addition to a radioactive labeling substance or instead of a radioactive labeling substance, a labeling substance which generates chemiluminescent emission when it contacts a chemiluminescent substrate and/or a fluorescent substance to selectively label the spot-like specific binding substances therewith, thereby obtaining a biochemical analysis unit, photoelectrically detecting chemiluminescent emission and/or fluorescence released from the biochemical analysis unit to produce biochemical analysis data, and analyzing the substance derived from a living organism.

Furthermore, according to the present invention, it is possible to provide a biochemical analyzing method which can effect quantitative biochemical analysis with high accuracy by producing biochemical analysis data based on a biochemical analysis unit obtained by forming spots of a specific binding substance on the surface of a carrier at high density, which can specifically bind with a substance derived from a living organism and whose sequence, base length, composition and the like are known, specifically binding the spot-like specific binding substances with a substance derived from a living organism labeled with a radioactive labeling substance, a labeling substance which generates chemiluminescent emission when it contacts a chemiluminescent substrate and/or a fluorescent substance, thereby selectively labeling the spot-like specific binding substances therewith.

The invention claimed is:

1. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate, the plurality of absorptive regions being selectively labeled with at least one kind of labeling substance selected from a group consisting of a radioactive labeling substance, a labeling substance which generates chemiluminescent emission when it contacts a chemiluminescent substrate and a fluorescent substance by spotting specific binding substances whose sequence or composition are known therein and specifically binding a substance derived from a living organism and labeled with at least one kind of said labeling substance with the specific binding substances wherein the absorptive region is formed of a material selected from the group consisting of a fiber material and a porous material, including a carbon material or a material adapted for forming a membrane filter and wherein the substance derived from a living organism is specifically bound with specific binding substances by a reaction selected from a group consisting of hybridization antigen-antibody reaction and receptor-ligand reaction.

2. A biochemical analyzing method comprising the steps of preparing a biochemical analysis unit by spotting specific binding substances, which specifically binds with a substance derived from a living organism and whose sequence or composition are known, in a plurality of absorptive regions, each of which is formed in a plurality of holes formed in a substrate made of a material which attenuates radiation energy and specifically binding a substance derived from a living organism and labeled with a radioactive labeling substance with the specific binding substances, superposing the biochemical analysis unit on a stimulable phosphor sheet in which a stimulable phosphor layer is formed so that the stimulable phosphor layer faces the plurality of absorptive regions, thereby exposing the stimulable phosphor layer to the radioactive labeling substance contained in the plurality of absorptive regions, irradiating the stimulable phosphor layer exposed to the radioactive labeling substance with a stimulating ray, thereby exciting stimulable phosphor contained in the stimulable phosphor layer, photoelectrically detecting stimulated emission released from the stimulable phosphor contained in the stimulable phosphor layer, thereby producing biochemical analysis data, and effecting biochemical analysis based on the biochemical analysis data.

3. A biochemical analyzing method in accordance with claim 2 wherein a plurality of dot-like stimulable phosphor layer regions are formed spaced-apart from each other in the stimulable phosphor sheet in the same pattern as that of the plurality of holes formed in the substrate of the biochemical analysis unit and the biochemical analysis unit and the stimulable phosphor sheet are superposed on each other so that each of the plurality of dot-like stimulable phosphor layer regions faces one of the plurality of absorptive regions in the plurality of holes formed in the substrate of the biochemical analysis unit, thereby exposing the plurality of dot-like stimulable phosphor layer regions of the stimulable phosphor sheet to the radioactive labeling substance contained in the plurality of absorptive regions.

4. A biochemical analyzing method comprising the steps of preparing a biochemical analysis unit comprising an absorptive substrate formed of an absorptive material and a perforated plate made of a material which attenuates radiation energy and light energy and formed with a plurality of through-holes, the perforated plate being closely contacted with at least one surface of the absorptive substrate to form a plurality of absorptive regions of the absorptive substrate in the plurality of through-holes formed in the perforated plate, the plurality of absorptive regions being selectively labeled with a radioactive labeling substance by spotting specific binding substances, which specifically binds with a substance derived from a living organism and whose sequence, or composition are known, in the plurality of absorptive regions and specifically binding a substance derived from a living organism and labeled with a radioactive labeling substance, superposing the biochemical analysis unit and a stimulable phosphor sheet in which a stimulable phosphor layer is formed via the perforated plate so that the stimulable phosphor layer faces the plurality of absorptive regions, thereby exposing the stimulable phosphor layer to the radioactive labeling substance contained in the plurality of absorptive regions, irradiating the stimulable phosphor layer exposed to the radioactive labeling substance with a stimulating ray to excite stimulable phosphor contained in the stimulable phosphor layer, photoelectrically detecting stimulated emission released from the stimulable phosphor contained in the stimulable phosphor layer to produce biochemical analysis data, and effecting biochemical analysis based on the biochemical analysis data.

5. A biochemical analyzing method in accordance with claim 4 wherein a plurality of dot-like stimulable phosphor layer regions are formed spaced-apart in the stimulable phosphor sheet in the same pattern as that of the plurality of through-holes formed in the perforated plate, and the biochemical analysis unit and the stimulable phosphor sheet are superposed on each other so that each of the plurality of dot-like stimulable phosphor layer regions faces one of the plurality of absorptive regions via one of the through-holes formed in the perforated plate, thereby exposing the plurality of dot-like stimulable phosphor layer regions to a radioactive labeling substance contained in the plurality of absorptive regions.

6. A biochemical analyzing method comprising the steps of preparing a biochemical analysis unit by spotting specific binding substances, which specifically binds with a substance derived from a living organism and whose sequence, or composition are known, in a plurality of absorptive regions formed in a plurality of holes formed in a substrate made of a material which attenuates light energy and specifically binding a substance derived from a living organism and labeled with a fluorescent substance with the specific binding substances, thereby selectively labeling a plurality of absorptive regions, irradiating the biochemical analysis unit with a stimulating ray, thereby exciting the fluorescent substance, photoelectrically detecting fluorescence released from the fluorescent substance, thereby producing biochemical analysis data, and effecting biochemical analysis based on the biochemical analysis data.

7. A biochemical analyzing method comprising the steps of preparing a biochemical analysis unit by spotting specific binding substances, which specifically binds with a substance derived from a living organism and whose sequence, or composition are known, in a plurality of absorptive regions formed in a plurality of holes formed in a substrate made of a material which attenuates light energy and specifically binding a substance derived from a living organism and labeled with a labeling substance which generates a chemiluminescent emission when it contacts a chemiluminescent substrate with the specific binding substances, thereby selectively labeling the plurality of absorptive regions, bringing the biochemical analysis unit into close contact with a chemiluminescent substrate, photoelectrically detecting chemiluminescent emission released from the labeling substance, thereby producing biochemical analysis data, and effecting biochemical analysis based on the biochemical analysis data.

8. A biochemical analyzing method comprising the steps of preparing a biochemical analysis unit by spotting specific binding substances, which specifically binds with a substance derived from a living organism and whose sequence or and composition are known, in a plurality of absorptive regions formed in a plurality of holes formed in a substrate made of a material which attenuates light energy and specifically binding a substance derived from a living organism and labeled with a fluorescent substance and a labeling substance which generates chemiluminescent emission when it contacts a chemiluminescent substrate with the specific binding substances, thereby selectively labeling the plurality of absorptive regions, irradiating the biochemical analysis unit with a stimulating ray to excite the fluorescent substance, and photoelectrically detecting fluorescence released from the fluorescent substance, thereby producing biochemical analysis data, while bringing the biochemical analysis unit into close contact with a chemiluminescent substrate, photoelectrically detecting chemiluminescent emission released from the labeling substance, thereby producing biochemical analysis data, and effecting biochemical analysis based on the biochemical analysis data.

9. A biochemical analysis unit in accordance with claim 1 wherein each of the plurality of holes is formed as a through-hole.

10. A biochemical analysis unit in accordance with claim 1 wherein each of the plurality of holes is formed as a recess.

11. A biochemical analysis unit in accordance with claim 1 wherein the substrate is formed of a flexible material.

12. A biochemical analysis unit in accordance with claim 1 wherein the substrate is formed with a gripping portion by which the substrate can be gripped.

13. A biochemical analysis unit in accordance with claim 1 which is formed with 10 or more holes.

14. A biochemical analysis unit in accordance with claim 13 which is formed with 1,000 or more holes.

15. A biochemical analysis unit in accordance with claim 14 which is formed with 10,000 or more holes.

16. A biochemical analysis unit in accordance with claim 1 wherein each of the plurality of holes has a size of less than 5 $mm^2$.

17. A biochemical analysis unit in accordance with claim 16 wherein each of the plurality of holes has a size of less than 1 $mm^2$.

18. A biochemical analysis unit in accordance with claim 17 wherein each of the plurality of holes has a size of less than 0.1 $mm^2$.

19. A biochemical analysis unit in accordance with claim 1 wherein the plurality of holes are formed at a density of 10 or more per $cm^2$.

20. A biochemical analysis unit in accordance with claim 19 wherein the plurality of holes are formed at a density of 1,000 or more per $cm^2$.

21. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate
wherein the absorptive region is formed of a material selected from the group consisting of a fiber material and a porous material, including an activated carbon material or a material adapted for forming a membrane filter,
wherein the plurality of holes are formed at a density of 10,000 or more per $cm^2$.

22. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate, the plurality of absorptive regions being selectively labeled with at least one kind of labeling substance selected from a group consisting of a radioactive labeling substance, a labeling substance which generates chemiluminescent emission when it contacts a chemiluminescent substrate and a fluorescent substance by spotting specific binding substances whose sequence or composition are known therein and specifically binding a substance derived from a living organism and labeled with at least one kind of said labeling substance with the specific binding substances
wherein the absorptive region is formed of a material selected from the group consisting of a fiber material and a porous material, including an activated carbon material or a material adapted for forming a membrane filter,
wherein the plurality of holes are formed at a density of 10,000 or more per $cm^2$.

23. A biochemical analysis unit in accordance with claim 20 wherein the plurality of holes are formed at a density of 10,000 or more per $cm^2$.

24. A biochemical analysis unit in accordance with claim 1 wherein the material which attenuates radiation energy and/or light energy has a property of reducing the energy of radiation and/or light to $\frac{1}{5}$ or less when the radiation and/or light travels in the material by a distance equal to that between neighboring absorptive regions.

25. A biochemical analysis unit in accordance with claim 24 wherein the material which attenuates radiation energy and/or light energy has a property of reducing the energy of radiation and/or light to $\frac{1}{10}$ or less when the radiation and/or light travels in the material by a distance equal to that between neighboring absorptive regions.

26. A biochemical analysis unit in accordance with claim 25 wherein the material which attenuates radiation energy and/or light energy has a property of reducing the energy of radiation and/or light to $1/100$ or less when the radiation and/or light travels in the material by a distance equal to that between neighboring absorptive regions.

27. A biochemical analysis unit in accordance with claim 24 wherein the substrate is formed of a material selected from a group consisting of metal material, ceramic material and plastic material.

28. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate
wherein the absorptive region is formed of a material selected from the group consisting of a fiber material and porous material, including a carbon material or a material adapted for forming a membrane filter and
wherein the plurality of holes are formed at a density of 10,000 or more per $cm^2$.

29. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate, the plurality of absorptive regions being selectively labeled with at least one kind of labeling substance selected from a group consisting of a radioactive labeling substance, a labeling substance which generates chemiluminescent emission when it contacts a chemiluminescent substrate and a fluorescent substance by spotting specific binding substances whose sequence or composition are known therein and specifically binding a substance derived from a living organism and labeled with at least one kind of said labeling substance with the specific binding substances
wherein the absorptive region is formed of a material selected from the group consisting of a fiber material and a porous material, including a carbon material or a material adapted for forming a membrane filter and
wherein the plurality of holes are formed at a density of 10,000 or more per $cm^2$.

30. A biochemical analysis unit comprising an absorptive substrate formed of an absorptive material and a perforated plate formed with a plurality of through-holes and made of a metal material which attenuates radiation energy and light energy, the perforated plate being closely contacted with at least one surface of the absorptive substrate to form a plurality of absorptive regions of the absorptive substrate in the plurality of through-holes formed in the perforated plate
wherein the absorptive region is formed of a material selected form the group consisting of a fiber material and a porous material, including a carbon material or a material adapted for forming a membrane filter and
wherein the plurality of holes are formed at a density of 10,000 or more per $cm^2$.

31. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate
wherein the absorptive region is formed of a fiber material including a carbon material or a material adapted for forming a membrane filter.

32. A biochemical analysis unit comprising a substrate made of a metal material which attenuates radiation energy and/or light energy and formed with a plurality of holes, and a plurality of absorptive regions formed by charging an absorptive material in the plurality of holes formed in the substrate, the plurality of absorptive regions being selectively labeled with at least one kind of labeling substance selected from a group consisting of a radioactive labeling substance, a labeling substance which generates chemiluminescent emission when it contacts a chemiluminescent substrate and a fluorescent substance by spotting specific binding substances whose sequence or composition are known therein and specifically binding a substance derived from a living organism and labeled with at least one kind of said labeling substance with the specific binding substances
wherein the absorptive region is formed of a fiber material including a carbon material or a material adapted for forming a membrane filter.

33. A biochemical analysis unit in accordance with claim 1 wherein the fiber material is selected from the group consisting of nylons and cellulose derivatives.

34. A biochemical analysis unit in accordance with claim 28 wherein the fiber material is selected from the group consisting of nylons and cellulose derivatives.

35. A biochemical analysis unit in accordance with claim 29 wherein the fiber material is selected from the group consisting of nylons and cellulose derivatives.

36. A biochemical analysis unit in accordance with claim 30 wherein the fiber material is selected from the group consisting of nylons and cellulose derivatives.

37. A biochemical analysis unit in accordance with claim 31 wherein the fiber material is selected from the group consisting of nylons and cellulose derivatives.

38. A biochemical analysis unit in accordance with claim 32 wherein the fiber material is selected from the group consisting of nylons and cellulose derivatives.

\* \* \* \* \*